(12) United States Patent  
Hutchison et al.

(10) Patent No.: US 7,081,458 B2  
(45) Date of Patent: Jul. 25, 2006

(54) MELANIN CONCENTRATING HORMONE RECEPTOR LIGANDS: SUBSTITUTED 1-BENZYL-4-ARYL PIPERAZINE ANALOGUES

(75) Inventors: Alan J. Hutchison, Madison, CT (US); John M. Peterson, Durham, CT (US); Dario Doller, Wallingford, CT (US); Wallace C. Pringle, Guilford, CT (US); Helen Yin, Milford, CT (US)

(73) Assignee: Neurogen Corp., Branford, CT (US)

( * ) Notice: Subject to any disclaimer, the term of this patent is extended or adjusted under 35 U.S.C. 154(b) by 0 days.

(21) Appl. No.: 11/103,246

(22) Filed: Apr. 11, 2005

(65) Prior Publication Data

US 2005/0182068 A1 Aug. 18, 2005

Related U.S. Application Data

(62) Division of application No. 10/152,189, filed on May 21, 2002.

(60) Provisional application No. 60/292,719, filed on May 22, 2001.

(51) Int. Cl.  
*A61K 31/407* (2006.01)  
*A61K 31/4439* (2006.01)  
*C07D 487/04* (2006.01)

(52) U.S. Cl. .......... 514/252.06; 514/338; 514/412; 544/238; 546/276.7; 548/453

(58) Field of Classification Search ............ 548/453; 514/412, 338; 546/276.7  
See application file for complete search history.

(56) References Cited

U.S. PATENT DOCUMENTS

| | | |
|---|---|---|
| 3,845,058 A | 10/1974 | Lembo et al. |
| 3,865,828 A | 2/1975 | Korosi et al. |
| 4,139,621 A | 2/1979 | Gardner et al. |
| 4,370,329 A | 1/1983 | Scherm et al. |
| 4,370,330 A | 1/1983 | Scherm et al. |
| 4,374,990 A | 2/1983 | Weber et al. |
| 4,532,240 A | 7/1985 | Werbel et al. |
| 4,806,536 A | 2/1989 | Cross et al. |
| 4,868,194 A | 9/1989 | Carr et al. |
| 4,921,863 A | 5/1990 | Sugimoto et al. |
| 4,937,246 A | 6/1990 | Sugihara et al. |
| 5,179,095 A | 1/1993 | Oinuma et al. |
| 5,569,659 A | 10/1996 | Reitz et al. |
| 5,681,954 A | 10/1997 | Yamamoto et al. |
| 5,688,798 A | 11/1997 | Godel et al. |
| 5,753,659 A | 5/1998 | Mills et al. |
| 5,859,246 A | 1/1999 | Thurkauf et al. |
| 5,869,488 A | 2/1999 | Shue et al. |
| 6,048,876 A | 4/2000 | Annoura et al. |
| 6,057,371 A | 5/2000 | Glennon et al. |
| 6,127,381 A | 10/2000 | Basu et al. |
| 6,172,229 B1 | 1/2001 | Thurkauf et al. |
| 6,284,761 B1 | 9/2001 | Zhang et al. |
| 6,414,149 B1 | 7/2002 | Chu-Moyer et al. |
| 6,455,528 B1 | 9/2002 | Adachi et al. |
| 6,472,394 B1 | 10/2002 | McKittrick et al. ......... 514/544 |
| 6,541,477 B1 | 4/2003 | Goehring et al. |
| 6,638,925 B1 * | 10/2003 | Czollner et al. ....... 514/212.02 |
| 6,664,273 B1 | 12/2003 | Burnett et al. .............. 514/546 |
| 2001/0039286 A1 | 11/2001 | Dinnell et al. |
| 2001/0049367 A1 | 12/2001 | Bennani et al. |

FOREIGN PATENT DOCUMENTS

| | | |
|---|---|---|
| BE | 620234 | 1/1963 |
| EP | 177392 | 4/1986 |
| EP | 211346 | 2/1987 |
| EP | 390654 | 10/1990 |
| EP | 624584 | 11/1994 |
| EP | 675118 | 10/1995 |
| EP | 1029851 | 8/2000 |
| EP | 1123928 | 8/2001 |
| ES | 549465 | 3/1986 |
| GB | 1378964 | 1/1975 |
| JP | P2001-226269 A | 8/2001 |
| JP | 2002322163 | 11/2002 |
| WO | WO 93/16057 | 8/1993 |
| WO | WO 95/34540 | 12/1995 |
| WO | WO 96/22977 | 8/1996 |
| WO | WO 97/17961 | 5/1997 |
| WO | 97/40049 | * 10/1997 |
| WO | WO 97/41108 | 11/1997 |
| WO | WO 97/44334 | 11/1997 |
| WO | WO 98/04528 | 2/1998 |
| WO | WO 98/11068 | 3/1998 |

(Continued)

OTHER PUBLICATIONS

Carpenter et al. Expert Opinion in Therapeutic Patents, vol. 12(11), p. 1639-1646 (2002).*

(Continued)

*Primary Examiner*—Emily Bernhardt  
(74) *Attorney, Agent, or Firm*—Ann T. Kadlecek; Seth A. Fidel

(57) ABSTRACT

Melanin concentrating hormone receptor ligands (especially 1-benzyl-4-aryl-piperazines, 1-benzyl-4-aryl-piperidines and related compounds), capable of modulating MCH receptor activity, are provided. Such ligands may be used to modulate MCH binding to MCH receptors in vivo or in vitro, and are particularly useful in the treatment of a variety of metabolic, feeding and sexual disorders in humans, domesticated companion animals and livestock animals. Pharmaceutical compositions and methods for treating such disorders are provided, as are methods for using such ligands for detecting MCH receptors (e.g., receptor localization studies).

31 Claims, No Drawings

FOREIGN PATENT DOCUMENTS

| | | |
|---|---|---|
| WO | WO 99/19301 | 4/1999 |
| WO | WO 99/54305 | 10/1999 |
| WO | WO 99/54320 | 10/1999 |
| WO | WO 00/23428 | 4/2000 |
| WO | WO 00/32582 | 6/2000 |
| WO | WO 00/51984 | 9/2000 |
| WO | WO 00/55139 | 9/2000 |
| WO | WO 00/68202 | 11/2000 |
| WO | WO 01/017965 | 3/2001 |
| WO | WO 01/21169 | 3/2001 |
| WO | WO 01/21577 | 3/2001 |
| WO | WO 01/82925 | 3/2001 |
| WO | WO 01/64676 | 9/2001 |
| WO | WO 01/87834 | 11/2001 |
| WO | WO 02/02744 | 1/2002 |
| WO | WO 02/04433 | 1/2002 |
| WO | WO 02/06245 | 1/2002 |

OTHER PUBLICATIONS

Bednarek et al. Journal of Biological Chemistry, vol. 277, p. 13821-13826 (2002).*

Lauteslager et al. Eur. J. Org. Chem. p.3105-3118 Aug. 2001.*

Ziminayi et al. Medline Abstract for Curr.Pharm.Des. 9(8), p627-641 (2003).*

Hervieu, Expert Opin.Ther.Targets 7(4), p. 495-511 (2003).*

Hanano et al (2000) Bioorganic & Medicinal Chemistry Letters 10:881-84.

Boissier et al., J. Med. Chem. 6(5):541-544 (1963).

Petigara et al., (1968) J. Med. Chem. 11:332-336.

* cited by examiner

SEQUENCE LISTING

<160> NUMBER OF SEQ ID NOS: 4

<210> SEQ ID NO 1
<211> LENGTH: 1062
<212> TYPE: DNA
<213> ORGANISM: Macaca fascicularis

<400> SEQUENCE: 1

```
atggacctgg aagcctcgct gctgcccact ggtcccaaca ccagcaacac ctctgatggc      60
cccgataacc tcacctcggc aggatcacct cctcgctcag ggagcgtctc ctacatcaac     120
atcatcatgc cttcggtgtt cggcaccatc tgcctcctgg catcatcgg  gaactccatg     180
gtcatcttcg cggtcgtgaa gaagtccaag ctgcactggt gcaacaatgt ccccgacatc     240
ttcatcatca acctctcggt ggtggatctc ctctttctcc tgggcatgcc cttcatgatc     300
caccagctca tgggcaatgg ggtgtggcac tttggggaga ccatgtgcac cctcatcacg     360
gccatggatg ccaatagtca gttcaccagc acctacatcc tgaccgccat ggccattgac     420
cgctacctgg ccaccgtcca ccccatctct tccacaaagt tccggaagcc ctctgtggcc     480
accctggtga tctgcctcct gtgggccctc tccttcatca gcatcacccc cgtgtggttg     540
tatgccagac tcatcccctt ccaggaggt  gcagtgggct gcggcatccg cttgcccaac     600
ccggacactg accttactg  gttcaccctg taccagtttt tcctggcctt tgccctgccc     660
ttcgtggtca tcacggccgc atacgtgagg atcctgcagc gcatgacgtc ctcagtggcc     720
cccgcctccc agcgcagcat ccggctgcgg acaaagaggg tgacccgcac agccatcgcc     780
atctgcctgg tcttctttgt gtgctgggca ccctactatg tgctacagct gacccagttg     840
tccatcagcc gcccgaccct caccttt gtc tacctgtaca atgcggccat cagcttgggc     900
tacgccaaca gctgcctcaa ccccttt gtg tacattgtgc tctgcgagac gttccgcaaa     960
cgcttggtcc tttcggtgaa gcctgcagcc caggggcagc ttcgcgctgt cagcaacgct    1020
cagacggctg acgaggagag gacagaaagc aaaggtacct ga                       1062
```

<210> SEQ ID NO 2
<211> LENGTH: 353
<212> TYPE: PRT
<213> ORGANISM: Macaca fascicularis

<400> SEQUENCE: 2

```
Met Asp Leu Glu Ala Ser Leu Leu Pro Thr Gly Pro Asn Thr Ser Asn
1               5                   10                  15

Thr Ser Asp Gly Pro Asp Asn Leu Thr Ser Ala Gly Ser Pro Pro Arg
                20                  25                  30

Ser Gly Ser Val Ser Tyr Ile Asn Ile Ile Met Pro Ser Val Phe Gly
            35                  40                  45

Thr Ile Cys Leu Leu Gly Ile Ile Gly Asn Ser Met Val Ile Phe Ala
        50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
                100                 105                 110
```

```
Glu Thr Met Cys Thr Leu Ile Thr Ala Met Asp Ala Asn Ser Gln Phe
            115                 120                 125

Thr Ser Thr Tyr Ile Leu Thr Ala Met Ala Ile Asp Arg Tyr Leu Ala
    130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
        275                 280                 285

Phe Val Tyr Leu Tyr Asn Ala Ala Ile Ser Leu Gly Tyr Ala Asn Ser
    290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr
```

<210> SEQ ID NO 3
<211> LENGTH: 24
<212> TYPE: DNA
<213> ORGANISM: Artificial Sequence
<220> FEATURE:
<223> OTHER INFORMATION: 5' macaque MCH1R primer

<400> SEQUENCE: 3
gagcaggcga ccggcactgg ctgg                                    24

<210> SEQ ID NO 4
<211> LENGTH: 28
<212> TYPE: DNA
<213> ORGANISM: Artificial Sequence
<220> FEATURE:
<223> OTHER INFORMATION: 3' macaque MCH1R primer

<400> SEQUENCE: 4
ggaggtgtgc agggtggcag gggaagta                                28

MELANIN CONCENTRATING HORMONE RECEPTOR LIGANDS: SUBSTITUTED 1-BENZYL-4-ARYL PIPERAZINE ANALOGUES

CROSS-REFERENCE TO RELATED APPLICATIONS

This application is a divisional of U.S. patent application Ser. No. 10/152,189, filed May 21, 2002 now U.S. Pat. No. 6,953,801, which claims priority to U.S. Provisional Application 60/292,719, filed May 22, 2001.

FIELD OF THE INVENTION

This invention relates generally to 1-benzyl-4-aryl piperazine and piperidine analogues. Certain such analogues are modulators of melanin concentrating hormone receptor. The invention further relates to the use of such compounds for treating a variety of metabolic, eating and sexual disorders, and as probes for the detection and localization of MCH receptors.

BACKGROUND OF THE INVENTION

Melanin concentrating hormone, or MCH, is a cyclic 19 amino acid neuropeptide that functions as a regulator of food intake and energy balance. MCH is produced in the hypothalamus of many vertebrate species, including humans, and serves as a neurotransmitter in the lateral and posterior hypothalamus. Both of these regions have been associated with behaviors such as eating, drinking, aggression and sexual behavior. MCH is also produced at various peripheral sites, including the gastrointestinal tract and testis.

The postulated role of MCH in feeding behavior and body weight has been confirmed by the finding that I.C.V. injection of MCH into the lateral ventricle of the hypothalamus increases caloric consumption in rats over similarly treated control animals. Furthermore, rats having the ob/ob genotype exhibit a 50–80% increase in MCH mRNA expression as compared to leaner ob/+ genotype mice. MCH knockout mice are leaner than their MCH-producing siblings due to hypophagia and an increased metabolic rate.

MCH activity is mediated via binding to specific receptors. The MCH type 1 receptor (MCHR1) is a 353 amino acid, 7-transmembrane, alpha-helical, G-coupled protein receptor, first reported by Lakaye, et al. (BBA (1998) 1401:216–220). MCHR1 has also been known as SLC-1. Immunohistochemistry studies of rat brain sections indicate that the MCHR1 receptor is widely expressed in the brain. MCHR1 receptor expression has been found in the olfactory tubercle, cerebral cortex, substantia nigra, basal forebrain CA1, CA2, and CA3 field of the hippocampus, amygdala, and in nuclei in the hypothalamus, thalamus, midbrain and hindbrain. Strong signals have been observed in the ventromedial and dorsomedial nuclei of the hypothalamus, two areas of the brain known to be involved in feeding behavior. Upon binding MCH, MCHR1 receptors expressed in HEK 293 cell mediate a dose dependent release of intracellular calcium. Cells expressing MCH receptors have also been shown to exhibit a pertussis toxin sensitive dose-dependent inhibition of forskolin-elevated cyclic AMP, indicating that the receptor couples to a $G_{i/o}$ G-protein alpha subunit.

Recently, a second MCH receptor (MCHR2) has been identified (An et al., Proc. Natl. Acad. Sci. USA (2001) 98:7576–7581; Sailer et al., Proc. Natl. Acad. Sci. USA (2001) 98:7564–7569; Hill et al., J. Biol. Chem. (2001) 276:20125–20129; Mori et al., Biochem. Biophys. Res. Commun. (2001) 283:1013–1018). MCHR2 has an overall amino acid identity of more than 30% with MCHR1, and is detected specifically in most regions of the brain, with an expression pattern similar to that of MCHR1.

Because MCH is an important regulator of food intake and energy balance, agents capable of modulating MCH receptor activity, especially MCHR1, are highly desirable for the treatment of obesity, eating disorders (e.g., bulimia and anorexia), sexual disorders (e.g., anorgasmic or psychogenic impotence) and metabolic disorders, such as diabetes. Small molecule, non-peptide antagonists of MCH receptors would be of particular value for such therapies. The present invention fulfills this need, and provides further related advantages.

SUMMARY OF THE INVENTION

The present invention provides MCH receptor modulators that inhibit or enhance MCH binding to MCH receptor and/or MCH receptor activity. Such modulators comprise a substituted 1-benzyl-4-aryl piperazine or piperidine analogue that exhibits a $K_i$ of 1 micromolar or less in an MCH receptor ligand binding assay and/or an MCH receptor-mediated signal transduction assay (calcium mobilization assay), and is characterized by the formula:

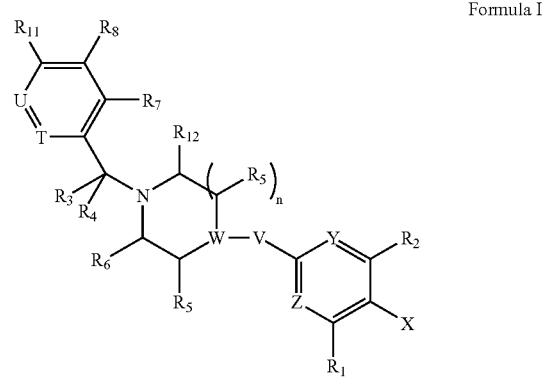

Formula I or a pharmaceutically acceptable salt thereof, wherein:

V is a bond or —(C=O)—;

W is nitrogen, CH, COH or CCN;

X is halogen, hydroxy, nitro, cyano, —COOH, oxo and groups of the formula L–M;

Y and Z are each independently: (i) CH, (ii) nitrogen, or (iii) joined with $R_5$ to form a carbocyclic or heterocyclic ring comprising W and V and having from 5 to 8 ring members, with the proviso that Y and Z are not both nitrogen;

n is 1 or 2;

$R_1$ and $R_2$ are each independently selected from: hydrogen, halogen, hydroxy, nitro, cyano, —COOH, oxo and groups of the formula L–M, with the proviso that if $R_1$ and $R_2$ are hydrogen, then V is —(C=O)—;

$R_3$ is: (i) selected from hydrogen, $(C_1$–$C_6)$alkyl, $(C_2$–$C_6)$ alkenyl and halo$(C_1$–$C_6)$alkyl; or (ii) joined with one or both of $R_6$ and $R_{10}$ to form a carbocyclic or heterocyclic group having one ring or two fused rings, wherein each ring contains from 5 to 8 ring members and 0, 1 or 2 heteroatoms independently chosen from oxygen, nitrogen and sulfur;

$R_4$ is hydrogen, $(C_1-C_6)$alkyl or halo$(C_1-C_6)$alkyl;

$R_5$ is (i) independently selected at each occurrence from hydrogen, halogen, hydroxy, nitro, cyano, amino, oxo, $(C_1-C_6)$alkyl, $(C_2-C_6)$alkenyl, $(C_2-C_6)$alkynyl, $(C_1-C_6)$alkoxy, halo$(C_1-C_6)$alkyl, halo$(C_1-C_6)$alkoxy, mono- and di$(C_1-C_6)$alkylamino, and amino$(C_1-C_6)$alkyl; or (ii) joined with $R_6$, Y or Z to form a carbocyclic or heterocyclic ring having from 5 to 8 ring members;

$R_6$ is: (i) selected from hydrogen, halogen, hydroxy, nitro, cyano, amino, oxo, $(C_1-C_6)$alkyl, $(C_2-C_6)$alkenyl, $(C_2-C_6)$alkynyl, $(C_1-C_6)$alkoxy, halo$(C_1-C_6)$alkyl, halo$(C_1-C_6)$alkoxy, mono- and di$(C_1-C_6)$alkylamino, and amino$(C_1-C_6)$alkyl), or (ii) joined with $R_3$ or $R_5$ to form a carbocyclic or heterocyclic group as described above;

$R_7$ is: (i) selected from hydrogen, halogen, hydroxy, nitro, cyano, —COOH, oxo; and groups of the formula L–M; or (ii) joined with $R_8$ or $R_{12}$ to form a fused 5- or 6-membered carbocyclic or heterocyclic group;

$R_8$ is: (i) selected from hydrogen, halogen, hydroxy, nitro, cyano, —COOH, oxo; and groups of the formula L–M; or (ii) joined with $R_7$ or $R_{11}$ to form a fused 5- to 10-member carbocyclic or heterocyclic group;

U is N, O or $CR_9$;

T is N, O or $CR_{10}$;

$R_9$ is: (i) selected from hydrogen, halogen, hydroxy, nitro, cyano, —COOH, oxo, and groups of the formula L–M; or (ii) joined with $R_{10}$ or $R_{11}$ to form a fused 5- to 10-member carbocyclic or heterocyclic group;

$R_{10}$ is: (i) selected from hydrogen, halogen, hydroxy, nitro, cyano, —COOH, oxo, and groups of the formula L–M; or (ii) joined with $R_3$, $R_8$ or $R_9$ to form a carbocyclic or heterocyclic group;

$R_{11}$ is: (i) selected from hydrogen, halogen, hydroxy, nitro, cyano, —COOH, oxo, and groups of the formula L–M; or (ii) joined with one or both of $R_8$ and $R_9$ to form a fused 5- to 10-member carbocyclic or heterocyclic group;

$R_{12}$ is: (i) independently selected at each occurrence from hydrogen, halogen, hydroxy, nitro, cyano, amino, oxo, $(C_1-C_6)$alkyl, $(C_2-C_6)$alkenyl, $(C_2-C_6)$alkynyl, $(C_1-C_6)$alkoxy, halo$(C_1-C_6)$alkyl, halo$(C_1-C_6)$alkoxy, mono- and di$(C_1-C_6)$alkylamino, and amino$(C_1-C_6)$alkyl; or (ii) joined with $R_7$ to form a fused carbocyclic or heterocyclic ring;

L is independently selected at each occurrence from a bond, —$NR_{14}$—, —O—, —$SO_2$—, —$SO_2NH$—, —C(=O)$NR_{14}$—, and —$NR_{14}C$(=O)—, wherein $R_{14}$ is independently selected at each occurrence from hydrogen, $(C_1-C_6)$alkyl, $(C_2-C_6)$alkenyl, $(C_2-C_6)$alkynyl, and halo$(C_1-C_6)$alkyl; and M is independently selected at each occurrence from hydrogen, $(C_1-C_6)$alkyl, $(C_2-C_6)$alkenyl, $(C_2-C_6)$alkynyl, halo$(C_1-C_6)$alkyl, amino$(C_1-C_6$alkyl) and 5 to 10-membered carbocycles;

with the proviso that if $R_{11}$ is halogen and V is a bond, then at least one of $R_{10}$, $R_3$ and $R_4$ is not hydrogen.

The present invention further provides MCH receptor modulators, comprising one or more compounds as described above associated with (i.e., linked to or combined with) at least one additional component, such as a drug, targeting moiety or carrier.

Within further aspects, the present invention provides pharmaceutical compositions comprising a compound or modulator as described above in combination with a physiologically acceptable carrier or excipient. Within certain embodiments, a pharmaceutical composition provided herein may further comprise one or more additional active agents (i.e., drugs). Pharmaceutical compositions provided herein may be formulated, for example, as an injectible fluid, an aerosol, a cream, a gel, a pill, a capsule, a syrup or a transdermal patch.

The present invention further provides, within other aspects, methods for treating a disease or disorder associated with MCH receptor activation, comprising administering to a patient in need of such treatment an effective amount of a compound or modulator as described above. Such diseases and disorders include, for example, eating disorders (e.g., obesity and bulimia nervosa), sexual disorders, diabetes, heart disease and stroke. The compound or modulator may be administered orally, or via another means such as intranasally, intravenously or topically. Within certain embodiments, the patient is a human, companion animal or livestock animal.

Within further aspects, the present invention provides compounds as described above, wherein the compounds are radiolabeled.

Methods are provided, within other aspects, for determining the presence or absence of MCH receptor in a sample, comprising the steps of: (a) contacting a sample with an agent comprising a compound as described above under conditions that permit binding of the agent to MCH receptor; and (b) detecting a level of agent bound to MCH receptor. Within certain embodiments, the agent is a radiolabeled compound, and the step of detection comprises the steps of: (i) separating unbound agent from bound agent; and (ii) determining an amount of bound agent in the sample. Detection may be achieved, for example, using autoradiography.

The present invention further provides, within other aspects, methods for modulating binding of ligand to MCH receptor. Certain such methods are performed in vitro, and comprise contacting MCH receptor with a compound or modulator as described above under conditions and in an amount sufficient to detectably modulate MCH binding to MCH receptor. Other such methods may be performed in vivo, and comprise contacting cells expressing MCH receptor with a compound or modulator as described above in an amount sufficient to detectably modulate MCH binding to cells expressing a cloned MCH receptor in vitro. Modulation of MCH binding may be determined, for example, using a ligand binding assay as provided herein.

Methods are further provided for modulating binding of MCH to MCH receptor in a patient, comprising administering to a patient (i.e., a human or non-human animal) a compound or modulator as described above. Patients may include, for example, companion animals such as dogs.

Within certain embodiments of the above methods, the modulation is inhibition and/or the MCH receptor is a human MCH receptor.

Within further aspects, the present invention provides methods for modulating the signal-transducing activity of MCH receptor, comprising contacting an MCH receptor, either in vivo or in vitro, with a sufficient amount of an MCH receptor modulator, under conditions suitable for binding of MCH to MCH receptor. Preferably, the MCH receptor is a MCH 1 receptor present in the hypothalamus.

Also provided by the present invention are packaged pharmaceutical preparations, comprising: (a) a pharmaceutical composition as described above in a container; and (b) instructions for using the composition to treat a patient suffering from a disease or disorder associated with MCH receptor activation. Such disorders include, for example eating disorders (e.g., obesity and bulimia nervosa), sexual disorders, diabetes, heart disease and stroke.

These and other aspects of the present invention will become apparent upon reference to the following detailed description.

DETAILED DESCRIPTION OF THE INVENTION

As noted above, the present invention provides MCH receptor modulators comprising small molecule MCH receptor ligands that are substituted 1-benzyl-4-aryl piperazine and piperidine analogues. Such modulators may be used in vitro or in vivo, to inhibit or enhance MCH binding to MCH receptors in a variety of contexts, as discussed in further detail below.

Terminology

Prior to setting forth the invention in detail, it may be helpful to provide definitions of certain terms to be used herein. Compounds of the present invention are generally described using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention. Where a compound exists in various tautomeric forms, the invention is not limited to any one of the specific tautomers, but rather includes all tautomeric forms. Certain compounds are described herein using a general formula that includes variables. Unless otherwise specified, each variable within such a formula is defined independently of other variable, and any variable that occurs more than one time in Formula I is defined independently at each occurrence. In addition, it will be apparent that combinations of substituents and/or variables are permissible only if such combinations result in a stable compound.

As used herein, "$(C_1-C_6)$alkyl" refers to optionally substituted, straight or branched chain alkyl groups or cycloalkyl groups having 1–6 carbon atoms such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, cyclopropyl, cyclopropylmethyl and cyclohexyl. A $(C_1-C_6)$alkyl group may be bonded to an atom within a molecule of interest via any chemically suitable portion of the $(C_1-C_6)$alkyl group. Preferred alkyl groups include methyl, ethyl, propyl, butyl, cyclopropyl, cyclopropylmethyl, cyclopentyl and cyclohexyl. Particularly preferred alkyl groups are $(C_1-C_4)$alkyl groups, especially methyl and ethyl.

Similarly, "$(C_2-C_6)$alkenyl" refers to optionally substituted, straight or branched chain alkene groups or cycloalkene groups having 2 to 6 carbon atoms, with $(C_2-C_4)$alkenyl groups preferred. Within an alkenyl group, one or more unsaturated carbon-carbon double bonds are present, and may occur at any stable point along the chain (e.g., ethenyl, allyl and isopropenyl). "$(C_2-C_6)$alkynyl" refers to straight or branched chain alkyne groups or cycloalkynyl groups having 2 to 6 carbon atoms, with $(C_2-C_4)$ alkynyl groups preferred. Within an alkynyl group, one or more unsaturated carbon-carbon triple bonds are present, and may occur at any stable point along the chain (e.g., ethynyl and propargyl). A "stable point" is bond that, when unsaturated, results in a chemically stable compound (i.e., a compound that can be isolated, characterized and tested for biological activity).

By "$(C_1-C_6)$alkoxy," in the present invention, is meant an optionally substituted alkyl group of 1 to 6 carbon atoms in a linear, branched or cycloalkyl arrangement attached via an oxygen bridge. $(C_1-C_6)$alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy. $(C_1-C_4)$alkoxy groups are generally preferred, especially ethoxy and methoxy. Similarly, "$(C_1-C_6)$alkylthio" refers to an alkyl group of 1 to 6 carbon atoms attached via a sulfur bridge.

"$(C_2-C_6)$alkanoyl" refers to an acyl group with 2 to 6 carbon atoms in a linear, branched or cycloalkyl arrangement. $(C_2-C_4)$alkanoyl groups are generally preferred.

"$(C_2-C_6)$alkanone" refers to a ketone substituent with 2 to 6 carbon atoms in a linear, branched or cyclic arrangement. $(C_2-C_4)$alkanone groups are generally preferred.

The term "$(C_1-C_6)$alkoxycarbonyl" refers to an alkoxy substituent linked via a carbonyl. In other words, an alkoxycarbonyl substituent has the general structure —C(=O)—O-alkyl.

"$(C_2-C_6)$alkylcarboxamido" refers to an alkyl substituent linked via a carboxamide group. In other words, an alkylcarboxamido substituent has the general structure —C(=O)—NH-alkyl.

"$(C_2-C_6)$alkylsulfonamido" refers to an alkyl substituent linked via a sulfonamide group. In other words, an alkylcarboxamido substituent has the general structure —SO$_2$—NH-alkyl.

"$(C_1-C_6)$alkanoyloxy," as used herein, refers to an alkanoyl group linked via an oxygen bridge. In other words, an alkanoyloxy group has the general structure —O—C(=O)-alkyl. $(C_1-C_4)$alkanoyloxy groups are generally preferred.

The term "$(C_1-C_6)$carbonate" refers to an alkoxycarbonyl group linked via an oxygen bridge. In other words, a carbonate group has the general structure —O—C(=O)—O-alkyl. $(C_1-C_4)$carbonate groups are generally preferred.

Similarly, "$(C_2-C_6)$alkyl ether" refers to an ether substituent with 2 to 6 carbon atoms, linked via a carbon-carbon bond. $(C_2-C_4)$alkylether groups are preferred.

The term "$(C_1-C_6)$carbamate," as used herein, refers to a group having the general structure —N—C(=O)—O-alkyl. $(C_1-C_4)$carbamate groups are generally preferred.

The term "oxo," as used herein, refers to a keto (C=O) group. An oxo group that is a substituent of a nonaromatic ring results in a conversion of —CH$_2$— to —C(=O)—. It will be apparent that the introduction of an oxo substituent on an aromatic ring destroys the aromaticity.

The term "oxime" refers to a group of the structure:

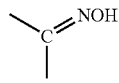

If an oxime is designated as a substituent, the carbon atom is generally part of the base structure, with only the =NOH added. The carbon atom of the oxime may, of course, be a member of a carbocyclic or heterocyclic ring. If a ring is aromatic, it will be apparent that the introduction of an oxime substituent destroys the aromaticity.

The term "halogen" includes fluorine, chlorine, bromine and iodine. A "haloalkyl" may be an optionally substituted, branched or straight-chain saturated aliphatic hydrocarbon group, substituted with 1 or more halogen atoms. "Halo "($C_1$–$C_6$)alkyl" groups have 1 to 6 carbon atoms; "halo ($C_1$–$C_4$)alkyl" groups have 1 to 4 carbon atoms. Examples of haloalkyl groups include, but are not limited to, mono-, di- or tri-fluoromethyl; mono-, di- or tri-chloromethyl; mono-, di-, tri-, tetra- or penta-fluoroethyl; and mono-, di-, tri-, tetra- or penta-chloroethyl. Typical haloalkyl groups are trifluoromethyl and difluoromethyl. Preferably not more than 5, and more preferably not more than 3, haloalkyl groups are present in compounds provided herein. The term "haloalkoxy" refers to a haloalkyl group as defined above attached via an oxygen bridge. "Halo($C_1$–$C_6$)alkoxy" groups have 1 to 6 carbon atoms.

A "substituent," as used herein, refers to a molecular moiety that is covalently bonded to an atom within a molecule of interest. For example, a "ring substituent" may be a moiety such as a halogen, alkyl group, alkoxy group, haloalkyl group or other group as discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3 or 4 positions, by one or more substituents independently selected from halogen, cyano, nitro, oxo, oxime, ($C_1$–$C_6$)alkyl, ($C_2$–$C_6$)alkenyl, ($C_2$–$C_6$)alkynyl, ($C_1$–$C_6$)alkoxy, ($C_1$–$C_6$)alkylthio, hydroxy, amino, mono or di($C_1$–$C_6$)alkyl amino, halo($C_1$–$C_6$)alkyl, halo($C_1$–$C_6$)alkoxy, ($C_1$–$C_6$)alkanoyl, ($C_1$–$C_6$)alkanone, ($C_1$–$C_6$)alkoxycarbonyl, ($C_1$–$C_6$)alkanoyloxy, ($C_1$–$C_6$)carbonate, ($C_1$–$C_6$)alkyl ether, ($C_1$–$C_6$)carbamate, —COOH, —$CONH_2$, mono- or di-($C_1$–$C_8$)alkylcarboxamido, —$SO_2NH_2$, mono and di($C_1$–$C_8$)alkylsulfonamido, and carbocyclic and heterocyclic groups as described below. Preferably, an optionally substituted group is substituted with 0 to 5 independently selected substituents; more preferably 0 to 3 independently selected substituents. Substituents may be located at any point(s) that result in a stable compound.

A dash ("-") that is not between two letters or symbols is used to indicate a point of attachment for a substituent. For example, —$CONH_2$ is attached through the carbon atom.

A "heteroatom," as used herein, is oxygen, sulfur or nitrogen.

A "carbocycle" or "carbocyclic group" comprises at least one ring formed entirely by carbon-carbon bonds (i.e., a carbocyclic ring). Unless otherwise specified, such ring(s) may be aromatic or non-aromatic (unsaturated, partially saturated or saturated), and are optionally substituted. The term "carbocyclic ring," as used herein encompasses rings in which ring carbon atoms are unsubstituted or substituted as described below. A carbocyclic group generally has from 1 to 3 fused or pendant carbocyclic rings, preferably one ring or two fused carbocyclic rings. Typically, each ring contains from 3 to 8 (preferably from 5 to 7) ring members; carbocyclic groups comprising fused or pendant ring systems typically contain from 9 to 14 members. A "ring member" is a carbon atom or heteroatom that is a part of a ring, and is directly bonded to two other such atoms. A phenyl or pyridyl group, for example, has 6 ring members, regardless of the number of atoms present within ring substituents. Representative examples of carbocyclic groups are optionally substituted cycloalkyl groups (e.g., cyclopentane and cyclohexane), as well as aromatic groups such as optionally substituted phenyl, benzyl, naphthyl, phenoxyl, benzoxyl and phenylethanonyl. Optional substitutions include those listed above. If a ring contains one or more substitutions, each substitution is selected independently of any other substitutions. ($C_5$–$C_{10}$)carbocyclic groups that contain 1 carbocyclic ring or 2 fused carbocyclic rings (for a total of 5 to 10 ring members), optionally substituted as described above, are preferred.

A "heterocycle" or "heterocyclic group" comprises at least one ring in which at least one ring atom is a heteroatom (i.e., N, O or S), and the remainder of the ring atoms are carbon (such a ring is referred to as a heterocyclic ring). Preferably, a heterocyclic group comprises 1–4 heteroatoms; within certain embodiments, groups comprising 1 or 2 heteroatoms are preferred. A heterocyclic group generally has from 1 to 3 fused or pendant rings, preferably one ring or two fused rings, each of which is optionally substituted. The term "heterocyclic ring," as used herein encompasses rings in which ring carbon atoms are substituted as described below. Each ring within a heterocyclic group is independently aromatic or non-aromatic (unsaturated, partially saturated or saturated). Typically, each ring contains from 3 to 8 ring members (preferably from 5 to 7 ring members); heterocyclic groups comprising fused or pendant ring systems typically contain from 9 to 14 ring members. Heterocyclic groups may be optionally substituted with from 1 to 5 substituents, each of which is independently selected from the optional substituents indicated above. Unless otherwise specified, a heterocyclic group may be aromatic or nonaromatic (e.g., a heterocycloalkyl such as piperazine or diazepane). 3- to 10-membered heterocyclic groups that contain 1 heterocyclic ring or 2 fused rings (at least one of which is heterocyclic; for a total of 3 to 10 ring members), optionally substituted as described above, are preferred, with 5- to 10-membered heterocyclic groups (i.e., groups with from 5 to 10 ring members and optional substitution(s)) particularly preferred.

Examples of heterocyclic groups include, but are not limited to, acridinyl, azocinyl, benzimidazolyl, benzofuranyl, benzothio-furanyl, benzothiophenyl, benzoxazolyl, benzothiazolyl, benzotriazolyl, benoztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, diazepanyl, dioxolanyl, dithiazinyl, dihydrofurotetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, quinuclidinyl, tetrahydrofuranyl, tetrahydroisoquinolinyl, tetrahydroquinolinyl, thiadiazinyl, thiadiazolyl, thianthrenyl, thiazolyl, thienyl, thienothiazolyl, thienooxazolyl, thienoimidazolyl, thiophenyl, triazinyl and xanthenyl. Within certain embodiments, pyridyl rings are preferred. It will be apparent that any such heterocyclic groups may be substituted with one or more substituents as described above.

The term "MCH receptor" refers to a protein comprising any MCH receptor sequence (i.e., a cellular protein that detectably binds MCH and mediates a dose dependent release of intracellular calcium). Naturally-occurring mammalian (especially human and monkey) MCH type 1 or type 2 receptor sequences are generally preferred. An MCH receptor may consist entirely of an endogenous sequence, or may comprise additional components (e.g., N-terminal leader sequence) that do not substantially inhibit the receptor's ability to bind MCH (i.e., at least 50% of the binding affinity of the receptor for MCH is retained). Similarly, truncated MCH receptor sequences, or sequences containing amino acid deletions, substitutes, additions or modifications may be used (e.g., chimeric receptors), provided that MCH receptor binding properties are not substantially diminished (i.e., at least 50% of the endogenous MCH-binding affinity is retained). The binding affinity of a candidate MCH receptor for MCH may be evaluated using a standard ligand binding assay as provided herein.

A "MCH receptor modulator," also referred to herein as a "modulator," is a compound that modulates (i.e., increases or decreases) MCH binding to one or more MCH receptors, as well as MCH receptor-mediated signal transduction. In other words, a modulator may be a MCH receptor agonist or antagonist. Modulators provided herein comprise a compound that is a substituted 1-benzyl-4-aryl piperazine or piperidine analogue having MCH receptor modulating activity. A modulator may consist entirely of such a compound, or may further comprise one or more additional moieties, provided that the modulating activity of the active compound is not substantially diminished,(i.e., the ability to increase or decrease MCH binding to MCH receptor, as determined using a binding assay provided herein, is not diminished by more than 50%). Such additional moieties include, for example, targeting moieties, other active agents and carriers, any of which may be linked to the active compound via a variety of standard techniques including direct condensation, or by way of bi- or multi-functional linkers. Alternatively, such additional moieties may be combined with the active compound, without covalent linking. A modulator binds "specifically" to MCH receptor if it binds to an MCH receptor (total binding minus nonspecific binding) with a Ki that is 10-fold, preferably 100-fold, and more preferably 1000-fold, less than the Ki measured for modulator binding to other G protein-coupled receptors. A modulator binds with "high affinity" if the $K_i$ at an MCH receptor is less than 1 micromolar, preferably less than 500 nanomolar, 100 nanomolar or 10 nanomolar. Assays to evaluate an effect on MCH binding to MCH receptor, as well as MCH receptor-mediated signal transduction, may be performed using the binding and calcium mobilization assays provided herein within Examples 2 and 3, respectively.

As used herein, a "substituted 1-benzyl-4-aryl piperazine or piperidine analogue" is any compound that satisfies the structure of Formula I.

A "targeting moiety" is a substance (e.g., a compound or a cell) that increases the local concentration of a modulator in the vicinity of a target site in a patient. There are a wide variety of targeting moieties known in the art, including antibodies and fragments thereof, receptors, ligands and other molecules that bind to cells of, or close to, a target tissue.

A "carrier," "carrier group" or "carrier molecule" is a substance that may be associated with an active compound prior to administration to a patient, generally for the purpose of controlling stability or bioavailability of the compound. Carriers for use within such formulations are generally biocompatible, and may also be biodegradable. Carriers include, for example, monovalent or multivalent molecules such as serum albumin (e.g., human or bovine), egg albumin, peptides, polylysine and polysaccharides such as aminodextran and polyamidoamines. Carriers also include solid support materials such as beads and microparticles comprising, for example, polylactate polyglycolate, poly(lactide-co-glycolide), polyacrylate, latex, starch, cellulose or dextran. A carrier may bear the compounds in a variety of ways, including covalent bonding (either directly or via a linker group), noncovalent interaction or admixture.

A "linker," as used herein, is any molecule that does not comprise a compound that detectably modulates MCH binding to an MCH receptor, and that can be covalently linked to at least two chemical moieties. Linkers may be used to link another moiety to a compound that modulates MCH binding to an MCH receptor. In general, a linker is bi-functional or multi-functional (e.g., a branched structure). Numerous linkers are known in the art, and may be incorporated into an MCH receptor modulator using any appropriate method known in the art.

A moiety is "associated with" an active compound if the moiety is linked to (covalently or noncovalently) or combined with the active compound.

A "prodrug" is a compound that may not fully satisfy the structural requirements of the compounds provided herein, but is modified in vivo, following administration to a patient, to produce an active compound as described herein. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino or sulfhydryl group, respectively. Examples of prodrugs include, but are not limited to, acetate, formate and benzoate derivatives of alcohol and amine functional groups within the compounds provided herein.

A "patient" is any individual treated with a MCH receptor modulator as provided herein. Patients include humans, as well as other animals such as companion animals and livestock. Patients may be afflicted with a condition associated with undesirable MCH receptor activation, or may be free of such a condition (i.e., treatment may be prophylactic).

Melanin Concentrating Hormone Receptor Modulators

As noted above, the present invention provides compounds of Formula I. Preferred such compounds are melanin concentrating hormone (MCH) receptor modulators (i.e., agents that detectably modulate both MCH binding to MCH receptor and MCH-mediated signal transduction). Such modulators may be specific for a particular MCH receptor (e.g., type 1 or type 2), or may inhibit or enhance ligand binding to multiple MCH receptors. MCH receptor modulators may be used to modulate MCH binding to MCH receptors in vivo, especially in the treatment of metabolic, feeding and sexual disorders in humans, domesticated companion animals and livestock animals. Modulators may also be used within a variety of in vitro assays, such as assays for receptor activity, as probes for detection and localization of MCH receptors and as standards in assays of MCH binding and MCH-mediated signal transduction.

The MCH receptor modulators provided herein comprise active compounds that are multi-aryl (i.e., have a plurality of unfused or fused aryl groups), non-peptide and amino acid free, and detectably modulate the binding of MCH to MCH receptor at nanomolar concentrations, preferably at subnanomolar concentrations. Active compounds provided herein are generally substituted 1-benzyl-4-aryl piperazine or piperidine analogues, as defined above. Preferred compounds bind specifically, and with high affinity, to an MCH receptor. In general, compounds provided herein have a $K_i$ at an MCH receptor of less than 1 micromolar. Without wishing to be bound to any particular theory, it is believed that the interaction of the compounds provided herein with an MCH receptor results in the MCH receptor modulating activity of these compounds. Active compounds include receptor agonists and antagonists.

The present invention is based, in part, on the discovery that small molecules having the general Formula I (as well as pharmaceutically acceptable salts and prodrugs thereof) modulate MCH binding to MCH receptor.

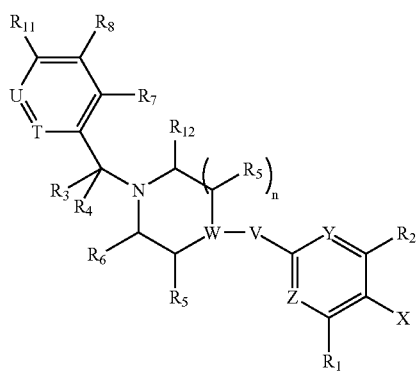

Formula I

Within Formula I, V is a bond or —(C=O)— and W is nitrogen, CH, COH or CCN. The variable "n" is 1 or 2; in other words, the heterocyclic ring comprising W may be a 6- or 7-membered ring, with 6-membered rings generally preferred.

X is selected from halogen, hydroxy, nitro, cyano, —COOH, oxo, and groups of the formula L–M, as defined below. As noted above, any carbocycle may be saturated, partially saturated or unsaturated, and may (but need not) be substituted with one or more (preferably from 1 to 3) substituents. Preferably, X is halogen, $(C_1–C_3)$alkyl, halo$(C_1–C_3)$alkyl, $(C_1–C_3)$alkoxy or halo$(C_1–C_3)$alkoxy, with halogen, methoxy and trifluoromethyl particularly preferred.

Y and Z are each independently: (i) CH, (ii) nitrogen, or (iii) carbon joined to $R_5$ to form a carbocyclic or heterocyclic ring comprising W and V having from 5 to 8 ring members. As noted above, any carbocyclic or heterocyclic ring so formed may be saturated, partially saturated or unsaturated, and is optionally substituted with one or more (preferably from 1 to 3) independently selected substituents as described above. It will be apparent that such a carbocyclic or heterocyclic ring includes, in addition to W and V, the carbon atom linked to V and a carbon atom adjacent to W. Within certain embodiments, Y and Z are both CH. Within certain embodiments, either Y or Z is nitrogen; preferably Y and Z are not both nitrogen. If one of Y or Z is joined to $R_5$, the other of Y and Z is either CH or nitrogen.

$R_1$ and $R_2$ are each independently selected from: (a) hydrogen, halogen, hydroxy, nitro, cyano, —COOH, and oxo; and (b) groups of the formula L–M, as defined below. Preferably, $R_1$ and $R_2$ are each independently selected from hydrogen, halogen, $(C_1–C_3)$alkyl, halo$(C_1–C_3)$alkyl, $(C_1–C_3)$alkoxy and halo$(C_1–C_3)$alkoxy, with hydrogen, halogen, methyl, methoxy and di- and tri-fluoromethyl particular preferred. Within certain preferred embodiments, one of $R_1$ and $R_2$ is hydrogen. If $R_1$ and $R_2$ are both hydrogen, then V is preferably —(C=O)—.

$R_3$ is: (i) selected from hydrogen, $(C_1–C_6)$alkyl, $(C_2–C_6)$alkenyl and halo$(C_1–C_6)$alkyl; or (ii) joined to one or both of $R_6$ and $R_{10}$ to form a carbocyclic or heterocyclic group having one ring or two fused rings, wherein each ring contains from 5 to 8 ring members and 0, 1 or 2 heteroatoms independently chosen from oxygen, nitrogen and sulfur, and wherein each ring is optionally substituted as described above. It will be apparent that any ring formed with $R_6$ includes the carbon atoms to which $R_3$ and $R_6$ are attached, as well as the nitrogen atom linked to these carbon atoms. Similarly, a ring formed with $R_{10}$ includes the carbon atoms to which $R_3$ and $R_{10}$ are attached, as well as the intervening carbon atom. Preferred $R_3$ groups are hydrogen, $(C_1–C_3)$alkyl (e.g., methyl or ethyl), halo$(C_1–C_3)$alkyl (e.g., trifluoromethyl) and groups that form a 5-membered, partially saturated ring with $R_{10}$ or a 5- or 6-membered saturated or partially saturated ring with $R_6$.

$R_4$ is hydrogen, $(C_1–C_6)$alkyl or halo$(C_1–C_6)$alkyl; preferably hydrogen, methyl or trifluoromethyl, with hydrogen particularly preferred.

$R_5$ is: (i) independently selected at each occurrence from hydrogen, halogen, hydroxy, nitro, cyano, amino, oxo, $(C_1–C_6)$alkyl, $(C_2–C_6)$alkenyl, $(C_2–C_6)$alkynyl, $(C_1–C_6)$alkoxy, halo$(C_1–C_6)$alkyl, halo$(C_1–C_6)$alkoxy, mono- and di$(C_1–C_6)$alkylamino, and amino$(C_1–C_6)$alkyl; or (ii) joined to $R_6$, Y or Z to form a carbocyclic or heterocyclic ring having from 5 to 8 ring members, optionally substituted as described above. For example, $R_5$ may be a direct bond to $R_6$, Y or Z, or may be any substituent that, when linked to $R_6$, Y or Z, results in a carbocyclic or heterocyclic ring of the appropriate size. As noted above, such a carbocyclic or heterocyclic ring includes W and V, as well as the carbon atom linked to V and a carbon atom adjacent to W. Preferably, each $R_5$ is independently hydrogen or methyl.

$R_6$ is: (i) selected from hydrogen, halogen, hydroxy, nitro, cyano, amino, oxo, $(C_1–C_6)$alkyl, $(C_2–C_6)$alkenyl, $(C_2–C_6)$alkynyl, $(C_1–C_6)$alkoxy, halo$(C_1–C_6)$alkyl, halo$(C_1–C_6)$alkoxy, mono- and di$(C_1–C_6)$alkylamino, and amino$(C_1–C_6)$alkyl; or (ii) joined with $R_3$ or $R_5$ to form a carbocyclic or heterocyclic group as described above. Preferably, $R_6$ is hydrogen or methyl, or is joined with $R_3$ to form a saturated or partially saturated 5- or 6-membered ring.

$R_7$ is: (a) selected from hydrogen, halogen, hydroxy, nitro, cyano, —COOH, oxo; and groups of the formula L–M, as defined below; or (b) joined with $R_8$ or $R_{12}$ to form a fused 5- or 6-membered carbocyclic or heterocyclic group (saturated, partially saturated or unsaturated, and optionally substituted). It will be apparent that any ring formed with $R_8$ includes the carbon atoms to which $R_7$ and $R_8$ are attached. Similarly, a ring formed with $R_{12}$ includes the carbon atoms to which $R_7$ and $R_{12}$ are attached. Within certain embodiments, $R_7$ is preferably hydrogen.

$R_8$ is: (a) selected from hydrogen, halogen, hydroxy, nitro, cyano, —COOH, oxo; and groups of the formula L–M, as defined below; or (b) joined with $R_7$ or $R_{11}$ to form a fused 5- to 10-member carbocyclic or heterocyclic group. Preferably, $R_8$ is hydrogen, halogen, $(C_1–C_3)$alkyl, halo$(C_1–C_3)$alkyl, $(C_1–C_3)$alkoxy or halo$(C_1–C_3)$alkoxy, or $R_8$ is joined with $R_7$ or $R_{11}$ to form a fused 5- or 6-membered ring, or a fused 9- or 10-membered bicyclic group.

U is N, O or $CR_9$; and $R_9$ is (a) selected from hydrogen, halogen, hydroxy, nitro, cyano, COOH, oxo, and groups of the formula L–M, as defined below; or (b) joined with $R_{10}$ or $R_{11}$ to form a fused 5- to 10-member carbocyclic or heterocyclic group. It will be apparent that any ring formed with $R_{10}$ includes the carbon atoms to which $R_9$ and $R_{10}$ are attached. Similarly, a ring formed with $R_{11}$ includes the carbon atoms to which $R_9$ and $R_{11}$ are attached. Preferably, $R_9$ is hydrogen, halogen, $(C_1–C_3)$alkyl (e.g., methyl) or $(C_1–C_3)$alkoxy (e.g., methoxy), or is fused with $R_{10}$ or $R_{11}$ to form a 6-membered aromatic ring.

T is N, O or CR$_{10}$; and R$_{10}$ is: (a) selected from hydrogen, halogen, hydroxy, nitro, cyano, —COOH, oxo, and groups of the formula L–M, as defined below; or (b) joined with R$_3$, R$_8$ or R$_9$ to form a carbocyclic or heterocyclic group as described above.

R$_{11}$ is: (a) selected from hydrogen, halogen, hydroxy, nitro, cyano, —COOH, oxo, and groups of the formula L–M, as defined below; or (b) joined with one or both of R$_8$ and R$_9$ to form a fused 5- to 10-member carbocyclic or heterocyclic group; Preferably, R$_{11}$ is hydrogen, hydroxy, halogen, (C$_1$–C$_3$)alkyl, halo(C$_1$–C$_3$)alkyl (e.g., trifluoromethyl) or (C$_1$–C$_3$)alkoxy (e.g., methoxy or ethoxy).

R$_{12}$ is: (i) independently selected at each occurrence from hydrogen, halogen, hydroxy, nitro, cyano, amino, oxo, (C$_1$–C$_6$)alkyl, (C$_2$–C$_6$)alkenyl, (C$_2$–C$_6$)alkynyl, (C$_1$–C$_6$)alkoxy, halo(C$_1$–C$_6$)alkyl, halo(C$_1$–C$_6$)alkoxy, mono- and di(C$_1$–C$_6$)alkylamino, and amino(C$_1$–C$_6$)alkyl; or (ii) joined to R$_7$ to form a fused carbocyclic or heterocyclic ring as described above. Preferably R$_{12}$ is hydrogen or methyl.

L is independently at each occurrence a bond, —NR$_{14}$—, —O—, —SO$_2$—, —SO$_2$NH—, —C(=O)NR$_{14}$—, and —NR$_{14}$C(=O)—, wherein R$_{14}$ is independently selected at each occurrence from hydrogen, (C$_1$–C$_6$)alkyl, (C$_2$–C$_6$)alkenyl, (C$_2$–C$_6$)alkynyl and halo(C$_1$–C$_6$)alkyl.

M is independently at each occurrence a hydrogen, (C$_1$–C$_6$)alkyl, (C$_2$–C$_6$)alkenyl, (C$_2$–C$_6$)alkynyl, halo(C$_1$–C$_6$)alkyl, amino(C$_1$–C$_6$ alkyl) or a 5- to 10-membered carbocycle.

Within certain preferred embodiments, at least one of R$_{10}$, R$_3$ and R$_4$ is not hydrogen. In particular, R$_{10}$, R$_3$ and R$_4$ are preferably not all hydrogen if R$_{11}$ is halogen and V is a bond.

Within certain embodiments, preferred compounds are chiral, and satisfy Formula Ia:

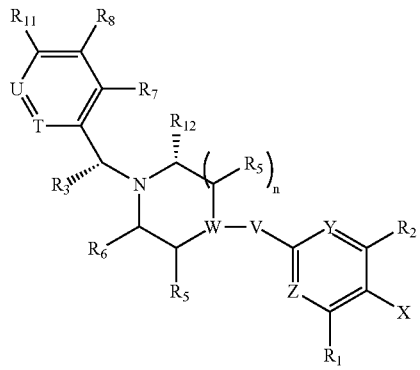

Formula Ia

Within Formula Ia, one or both of R$_3$ and R$_{12}$ is not hydrogen. Variables shown in Formula Ia are otherwise as defined for Formula I. If R$_3$ is not hydrogen, then the carbon to which R$_3$ is attached is in the R configuration (assuming that R$_3$ has a lower priority than the other groups attached to the carbon); in other words, for compounds having an alpha-methyl or -ethyl benzyl group (R$_3$ is methyl or ethyl, R$_4$ is hydrogen), the R enantiomer is generally preferred. Similarly if R$_{12}$ is not hydrogen, then the carbon to which R$_{12}$ is attached is in the S configuration (if R$_{12}$ has a lower priority than the other groups attached to the carbon). Compounds with chiral carbon atoms may be indicated as the R or S enantiomers; compounds in which neither R$_3$ nor R$_{12}$ is hydrogen may be indicated herein as the (R,S) enantiomer. In the absence of such designation, compounds specifically recited herein should be interpreted as encompassing both racemic and chiral forms. In addition, solid black lines of constant width are used within certain structures provided herein to indicate relative stereochemistry of one stereocenter with respect to another. Such lines do not indicate absolute stereochemistry (which is indicated herein using standard wedge lines).

Certain compounds provided herein satisfy one or more of Formulas II–IV, in which variable positions are defined as in Formula I:

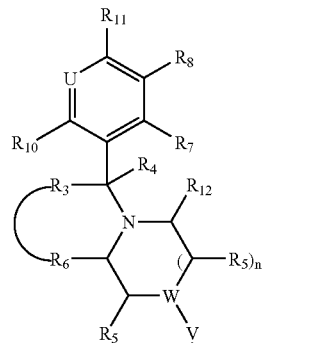

Formula II

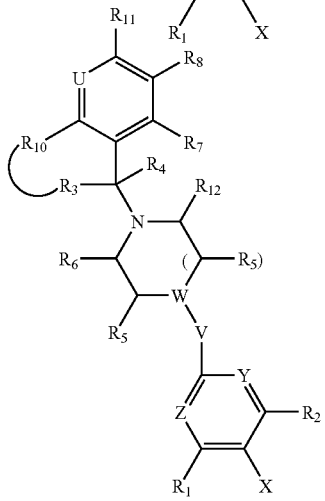

Formula III

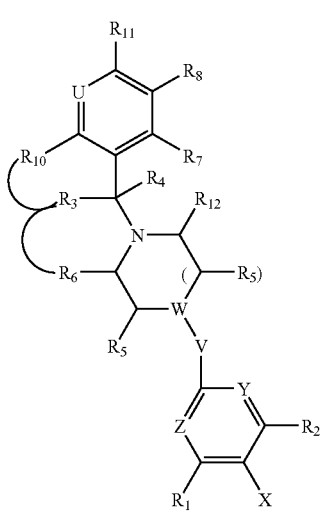

Formula IV

Within Formula II, $R_3$ and $R_6$ are joined to form an unsaturated, partially unsaturated or saturated ring, wherein the ring contains 5 to 8 ring members of which 0, 1 or 2 are heteroatoms (independently chosen from oxygen, nitrogen and sulfur). Similarly, within Formula III, $R_3$ and $R_{10}$ are joined to form an unsaturated, partially unsaturated or saturated ring that contains 5 to 8 ring members of which 0, 1 or 2 are heteroatoms. Within Formula IV, $R_3$, $R_6$ and $R_{10}$ are joined to form two fused rings, each of which is independently unsaturated, partially saturated or saturated, and each of which contains from 5 to 8 ring members of which 0, 1 or 2 are heteroatoms.

A representative example of Formula II is shown below:

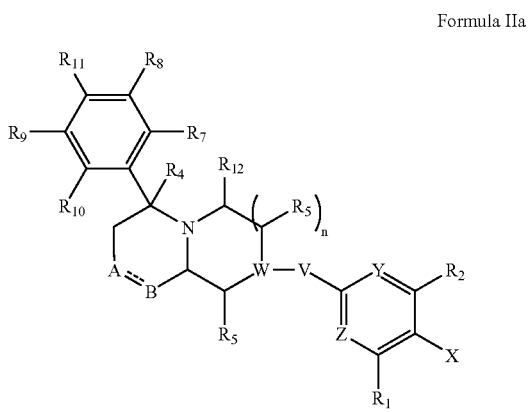

Formula IIa

Within Formula IIa, A and B are each independently selected from O, N, S, $CR_{13}$ and $CHR_{13}$, wherein $R_{13}$ is independently selected at each occurrence from hydrogen, halogen, cyano, hydroxy, oxo, oxime, $C_1-C_6$ alkyl, $C_1-C_6$ alkoxy, $C_1-C_6$ alkanoyl, $C_1-C_6$ alkanoyloxy, $C_1-C_6$ alkoxycarbonyl, halo($C_1-C_6$)alkyl and halo($C_1-C_6$)alkoxy. Preferably, $R_4$ is hydrogen or methyl, $R_5$ is independently selected at each occurrence from hydrogen and methyl, $R_{11}$ is hydrogen, halogen, methoxy or hydroxy and $R_7$, $R_8$ and $R_9$ are each independently selected from hydrogen, $C_1-C_6$ alkyl, $C_1-C_6$ alkoxy and halogen.

Representative compounds of Formula I include, but are not limited to those in which W is N and $R_3$ and $R_4$ are both H. Such compounds include, for example: 1-(4-bromo-3-methoxyphenyl)-4-(3,4-dimethoxybenzyl)piperazine; 1-(4-bromo-3-methoxy-phenyl)-4-(4-chlorobenzyl)piperazine; 1-[4-chloro-3-(trifluoromethyl)phenyl]-4-(3,4-dimethoxy-benzyl)piperazine; 1-(3,4-dichlorophenyl)-4-(3,4-dimethoxybenzyl)piperazine; 1-(4-bromo-3-methoxyphenyl)-4-(4-methoxy-2,5-dimethylbenzyl)piperazine; 1-(4-bromo-3-methoxyphenyl)-4-(4-methoxy-2,3-dimethylbenzyl)piperazine; 1-(3-bromo-4-methoxybenzyl)-4-(4-bromo-3-methoxyphenyl)piperazine; 4-{[4-(4-bromo-3-methoxy-phenyl)-piperazin-1-yl]methyl}-2-methoxyphenol; 4-({4-[4-chloro-3-(trifluoromethyl)phenyl]-piperazin-1-yl}methyl)-2-methoxyphenol; 1-[4-chloro-3-(trifluoromethyl)phenyl]-4-(4-methoxy-2,3-dimethylbenzyl)piperazine; 1-(3-bromo-4-methoxybenzyl)-4-[4-chloro-3-(trifluoromethyl)phenyl]piperazine; 1-(4-bromo-3-methoxyphenyl)-4-(4-methoxy-3-methylbenzyl)piperazine; 1-[4-chloro-3-(trifluoromethyl)phenyl]-4-(4-methoxy-3-methyl-benzyl)piperazine; 1-(4-chloro-3-trifluoromethoxyphenyl)-4-[1-(3,4-dimethoxy-benzyl)]-2-methyl-piperazine; 4-(4-chloro-3-trifluoromethyl-phenyl)-1-(3,4-dimethoxy-benzyl)-2-methyl-piperazine; 4-(4-chloro-3-methoxy-phenyl)-1-(3,4-dimethoxy-benzyl)-2-methyl-piperazine; 4-(4-chloro-3-methoxy-phenyl)-[1-(3,4-dimethoxy-benzyl)-ethyl]-2-methyl-piperazine; 3-{[4-(4-bromo-3-methoxyphenyl)piperazin-1-yl]methyl}-9-ethyl-9H-carbazole; 1-(5-bromo-6-methoxypyridin-2-yl)-4-(3,4-dimethoxybenzyl)piperazine; 1-(5-bromo-6-methoxypyridin-2-yl)-4-(4-chlorobenzyl)piperazine; 1-(5-bromo-6-methoxypyridin-2-yl)-4-(4-methoxy-2,5-dimethylbenzyl)piperazine; 1-(5-bromo-6-methoxypyridin-2-yl)-4-(4-methoxy-2,3-dimethylbenzyl)piperazine; 1-(3-bromo-4-methoxybenzyl)-4-(5-bromo-6-methoxypyridin-2-yl)piperazine; 4-(5-bromo-6-methoxypyridin-2-yl)-1-(3,4-dimethoxy-benzyl)-2-methylpiperazine; 4-(5-bromo-6-methoxypyridin-2-yl)-1-(3,4-dimethoxy-benzyl)-2-methylpiperazine; 1-(5-bromo-6-methoxypyridin-2-yl)-4-(4-methoxy-3-methylbenzyl)piperazine; 3-{[4-(5-bromo-6-methoxypyridin-2-yl)piperazin-1-yl]methyl}-9-ethyl-9H-carbazole; 4-{[4-(5-bromo-6-methoxypyridin-2-yl)piperazin-1-yl]methyl}-2-methoxyphenol; and 1-(4-bromo-3-methoxyphenyl)-4-(3,4-dimethoxybenzyl)-1,4-diazepane.

Within other embodiments, W is N and $R_3$ is not hydrogen. Such compounds include, for example: 1-(4-bromo-3-methoxyphenyl)-4-[1-(3,4-dimethoxyphenyl)-ethyl]piperazine; 1-[4-chloro-3-(trifluoromethyl)phenyl]-4-[1-(3,4-dimethoxyphenyl)ethyl]-piperazine; 1-(4-bromo-3-methoxyphenyl)-4-[1-(4-methoxyphenyl)ethyl]piperazine; 1-(4-chloro-3-methoxyphenyl)-4-[1-(3,4-dimethoxyphenyl)ethyl]piperazine; 1-(4-bromo-3-methoxyphenyl)-4-[1-(3,4-difluorophenyl)ethyl]piperazine; 4-{1-[4-(4-bromo-3-methoxyphenyl)piperazin-1-yl]ethyl}-2-methylphenol; 1-(4-bromo-3-methoxyphenyl)-4-[1-(4-fluoro-3-methoxyphenyl)-ethyl]piperazine; 1-(4-chloro-3-methoxyphenyl)-4-[1-(3,4-dimethoxyphenyl)ethyl]piperazine; 1-(4-chloro-3-methoxyphenyl)-4-[1-(3,4-dimethoxyphenyl)ethyl]piperazine; 1-(4-bromo-3-trifluoromethoxyphenyl)-4-[1-(3-fluoro-4-methoxyphenyl)ethyl]piperazine; 1-(4-bromo-3-trifluoromethoxyphenyl)-4-[1-(3-fluoro-4-methoxyphenyl)ethyl]piperazine; 1-(4-bromo-3-trifluoromethylphenyl)-4-[1-(3-fluoro-4-methoxyphenyl)ethyl]piperazine; 1-(4-methoxy-phenyl)-4-[1-(3,4-dimethoxyphenyl)ethyl]piperazine; 1-(4-methoxylphenyl)-4-[1-(3,4-dimethoxyphenyl)ethyl]piperazine; 1-(4-bromo-3-methoxy-phenyl)-4-[1-(4-chloro-phenyl)-ethyl]-piperazine; 1-(4-chloro-3-methoxy-phenyl)-4-[1-(4-methoxy-2,3-dimethyl-phenyl)-ethyl]-piperazine; 1-(4-chloro-3-methoxy-phenyl)-4-[1-(4-chloro-3-methoxy-phenyl)-ethyl]-piperazine; 1-(4-bromo-3-methoxy-phenyl)-4-[1-(4-methoxy-2,5-dimethyl-phenyl)-ethyl]-piperazine; 1-(4-fluoro-3-trifluoromethyl-phenyl)-4-[1-(3,4-dimethoxy-phenyl)-ethyl]-piperazine; 1-(4-bromo-3-methoxy-phenyl)-4-[1-(3,4-dimethoxy-phenyl)-ethyl]-piperazine; 1-(4-chloro-3-trifluoromethyl-phenyl)-4-[1-(3,4-dimethoxy-phenyl)-ethyl]-piperazine; 1-(4-bromo-3-methoxy-phenyl)-4-[1-(4-ethoxy-3-methoxy-phenyl)-ethyl]-piperazine; 1-(4-chloro-3-methoxy-phenyl)-4-[1-(4-fluoro-3-methoxy-phenyl)-ethyl]-piperazine; 1-(4-bromo-3-methoxy-phenyl)-4-[1-(2,4,5-trimethyl-phenyl)-ethyl]-piperazine; 1-(4-bromo-3-methoxy-phenyl)-4-[1-(3-fluoro-4-methoxy-phenyl)-ethyl]-piperazine; 1-(4-chloro-3-trifluoromethyl-phenyl)-4-[1-(4-methoxy-2,3-dimethyl-phenyl)-ethyl]-piperazine; 1-(4-fluoro-3-methoxy-phenyl)-4-[1-(3,4-dimethoxy-phenyl)-ethyl]-piperazine; 1-(4-chloro-3-trifluoromethyl-phenyl)-4-[1-(4-chloro-3-methoxy-phenyl)-ethyl]-piperazine; 1-(4-chloro-3-trifluoromethyl-phenyl)-4-[1-(4-methoxy-3-methyl-phenyl)-ethyl]-piperazine; 1-(4-bromo-3-methoxy-phenyl)-4-[1-(3-methoxy-phenyl)-ethyl]-piperazine; 1-(4-bromo-3-methoxy-phenyl)-4-[1-(4- trifluormethyl-phenyl)-ethyl]-piperazine; 4-(4-fluoro-3-trifluoromethyl-phenyl)-1-[1-(3,4-dimethoxy-phenyl)-ethyl]-piperazine; 1-(4-chloro-3-methoxy-phenyl)-4-[1-(3-fluoro-4-methoxy-phenyl)-ethyl]-piperazine; 1-(4-bromo-3-methoxy-phenyl)-4-[1-(3-ethoxy-phenyl)-ethyl]-piperazine; 1-(5-{1-[4-(4-bromo-3-methoxy-phenyl)-piperazin-1-yl]-ethyl}-2-fluoro-phenyl)-ethanone; 1-(4-chloro-3-methyl-phenyl)-4-[1-(4-methoxy-3-methyl-phenyl)-ethyl]-piperazine; 1-(4-bromo-3-methoxy-phenyl)-4-[1-(3,5-dimethoxy-phenyl)-ethyl]-piperazine; 1-(4-methoxy-3-methyl-phenyl)-4-[1-(4-methoxy-2,3-dimethyl-phenyl)-ethyl]-piperazine; 1-(4-chloro-3-methyl-phenyl)-4-[1-(3,4-dimethoxy-phenyl)-ethyl]-piperazine; 1-(4-bromo-3-methoxy-phenyl)-4-[1-(3,4-diethoxy-phenyl)-ethyl]-piperazine; 1-(4-chloro-3-fluoro-phenyl)-4-[1-(4-methoxy-2,3-dimethyl-phenyl)-ethyl]-piperazine; 1-(4-chloro-3-methyl-phenyl)-4-[1-(4-methoxy-2,3-dimethyl-phenyl)-ethyl]-piperazine; 1-(4-chloro-3-fluoro-phenyl)-4-[1-(3,4-dimethoxy-phenyl)-ethyl]-piperazine; 1-(4-methoxy-3-methyl-phenyl)-4-[1-(3-methyl-4-methoxy-phenyl)-ethyl]-piperazine; 1-(4-methoxy-3-methyl-phenyl)-4-[1-(3,4-dimethoxy-phenyl)-ethyl]-piperazine; 1-(3,4-dimethoxy-phenyl)-4-[1-(4-methoxy-2,3-dimethyl-phenyl)-ethyl]-piperazine; 1-(4-fluoro-3-trifluoromethyl-phenyl)-4-[1-(3,4-dimethoxy-phenyl)-ethyl]-piperazine; 1-(4-bromo-3-methoxy-phenyl)-4-{1-[4-(4-bromo-phenyl)-phenyl]-ethyl}-piperazine; 4-(4-chloro-3-trifluoromethyl-phenyl)-[1-(3,4-dimethoxy-benzyl)-ethyl]-piperazine; 1-(1-benzo[1,3]dioxol-5-yl-ethyl)-4-(4-bromo-3-methoxy-phenyl)-piperazine; 1-(4-bromo-3-methoxy-phenyl)-4-[1-(3,4-dimethoxy-phenyl)-ethyl]-[1,4]diazepane; 1-(4-bromo-3-methoxy-phenyl)-4-[1-(3-fluoro-4-methoxy-phenyl)-ethyl]-[1,4]diazepane; 1-[1-(3,4-dimethoxy-phenyl)-ethyl]-4-(3-methoxy-phenyl)-piperazine-2,5-dione; 1-(4-bromo-3-methoxy-phenyl)-4-[1-(3,4-dimethoxy-phenyl)-propyl]-piperazine; 1-(4-chloro-3-trifluoromethyl-phenyl)-4-[1-(3,4-dimethoxy-phenyl)-propyl]-piperazine; 1-(5-bromo-6-methoxypyridin-2-yl)-4-[1-(3,4-dimethoxyphenyl)ethyl]piperazine; 1-(5-bromo-6-methoxy-pyridin-2-yl)-4-[1-(4-trifluoromethyl-phenyl)-ethyl]-piperazine; 1-(4-bromo-3-methoxy-phenyl)-4-[1-(6-methoxy-naphthalen-2-yl)-ethyl]-piperazine; 1-(4-chloro-3-methoxy-phenyl)-4-[1-(3,4-dimethoxy-phenyl)-ethyl]-piperazine; 1-(4-bromo-3-methoxy-phenyl)-4-[1-(4-fluoro-3-methoxy-phenyl)-ethyl]-piperazine; and 1-(4-bromo-3-methoxy-phenyl)-4-[1-(6-methoxy-pyridin-2-yl)-ethyl]-piperazine.

Representative compounds in which W is C, COH or CCN include, for example: 4-(4-chloro-3-trifluoromethyl-phenyl)-1-[1-(3,4-dimethoxy-phenyl)-ethyl]-piperidine; and 4-[4-chloro-3-(trifluoromethyl)phenyl]-1-(3,4-dimethoxy-benzyl)piperidin-4-ol.

Representative compounds of Formula II include, for example: 2-(4-chloro-3-methoxy-phenyl)-6-(3,4-dimethoxy-phenyl)-octahydro-pyrido[1,2-a]pyrazine; 2-(4-chloro-3-trifluoromethyl-phenyl)-6-(3,4-dimethoxy-phenyl)-octahydro-pyrido[1,2-a]pyrazine; 2-(4-chloro-3-methoxy-phenyl)-6-(3-fluoro, 4-methoxy-phenyl)-octahydro-pyrido[1,2-a]pyrazine; 2-(4-fluoro-3-methoxy-phenyl)-6-(3,4-dimethoxy-phenyl)-octahydro-pyrido[1,2-a]pyrazine; 2-(4-fluoro-3-trifluoromethyl-phenyl)-6-(3,4-dimethoxy-phenyl)-octahydro-pyrido[1,2-a]pyrazine; 2-(4-chloro-3-methoxy-phenyl)-6-methoxy-naphthalen-2-yl)-octahydro-pyrido[1,2-a]pyrazine; 2-(4-chloro-3-methyl-phenyl)-6-(3,4-dimethoxy-phenyl)-octahydro-pyrido[1,2-a]pyrazine; 2-(4-methoxy-3-methyl-phenyl)-6-(3,4-dimethoxy-phenyl)-octahydro-pyrido[1,2-a]pyrazine; 2-(4-chloro-3-methoxy-phenyl)-6-(3-methoxy-phenyl)-octahydro-pyrido[1,2-a]pyrazine; 2-(2,4-dibromo-5-methoxy-phenyl)-6-(3,4-dimethoxy-phenyl)-octahydro-pyrido[1,2-a]pyrazine; 2-(3,4-dimethoxy-phenyl)-6-(3,4-dimethoxy-phenyl)-octahydro-pyrido[1,2-a]pyrazine; 2-(4-chloro-3-fluoro-phenyl)-6-(3,4-dimethoxy-phenyl)-octahydro-pyrido[1,2-a]pyrazine; 1-(4-fluoro-3-methoxy-phenyl)-6-(3,4-dimethoxy-phenyl)-octahydro-pyrido[1,2-a]pyrazine; 2-(4-chloro-3-methoxy-phenyl)-6-(3,4-dimethoxy-phenyl)-octahydro-pyrido[1,2-a]pyrazin-8-ol; 2-(4-chloro-3-methoxy-phenyl)-6-(3,4-dimethoxy-phenyl)-octahydro-pyrido[1,2-a]pyrazin-8-one; 2-(4-chloro-3-methoxy-phenyl)-6-(3-fluoro-4-methoxy-phenyl)-octahydro-pyrido[1,2-a]pyrazin-8-one; 2-(4-chloro-3-methoxy-phenyl)-6-(6-methoxy-naphthalen-2-yl)-octahydro-pyrido[1,2-a]pyrazin-8-one; 8-(4-chloro-3-methoxy-phenyl)-4-(3,4-dimethoxy-phenyl)-octahydro-pyrazino[2,1-c][1,4]thiazine; 2-(4-chloro-3-methoxy-phenyl)-6-(3,4-dimethoxy-phenyl)-octahydro-pyrrolo[1,2-a]pyrazine; 2-(4-chloro-3-methoxy-phenyl)-6-(3,4-dimethoxy-phenyl)-1,3,4,6,9,9a-hexahydro-2H-pyrido[1,2-a]pyrazine; 8-bromo-3-(3,4-dimethoxy-benzyl)-9-methoxy-2,3,4,4a-tetrahydro-1H,6H-pyrazino[1,2-a]quinoxalin-5-one; 7-(4-chloro-3-methoxy-phenyl)-4-(3,4-dimethoxy-phenyl)-decahydro-naphthalen-2-ol; and 2-(4-chloro-3-methoxy-phenyl)-6-(3,4-dimethoxy-phenyl)-8-fluoro-octahydro-pyrido[1,2-a]pyrazine.

Representative compounds of Formula III include, for example: 1-(4-bromo-3-methoxyphenyl)-4-(5,6-dimethoxy-2,3-dihydro-1H-indan-1-yl)piperazine; 1-(5-bromo-6-methoxypyridin-2-yl)-4-(5,6-dimethoxy-2,3-dihydro-1H-indan-1-yl)piperazine; 1-(4-chloro-3-trifluoromethyl-phenyl)-4-(4,5-dimethoxy-indan-1-yl)-piperazine; and 1-(4-bromo-3-methoxy-phenyl)-4-(4,5-dimethoxy-indan-1-yl)-piperazine.

Representative compounds in which V is —C(═O)— include, for example: (4-chloro-phenyl)-{4-[1-(2,3-dimethyl-phenyl)-ethyl]-piperazin-1-yl}-methanone; (4-chloro-phenyl)-{4-[1-(4-methoxy-2,3-dimethyl-phenyl)-ethyl]-piperazin-1-yl}-methanone; (4-trifluoro-methyl-phenyl)-{4-[1-(4-methoxy-2,3-dimethyl-phenyl)-ethyl]-piperazin-1-yl}-methanone; (3,4-dichloro-phenyl)-{4-[1-(4-methoxy-2,3-dimethyl-phenyl)-ethyl]-piperazin-1-yl}-methanone; (4-chloro-phenyl)-{4-[1-(4-methyl-naphthalen-1-yl)-ethyl]-piperazin-1-yl}-methanone; (4-trifluoro-methyl-phenyl)-{4-[1-(4-methoxy-2-methyl-phenyl)-ethyl]-piperazin-1-yl}-methanone; (4-trifluoromethyl-phenyl)-{4-[1-(4-methoxy-2,3-dimethyl-phenyl)-ethyl]-piperazin-1-yl}-methanone; 4-trifluoromethyl-phenyl)-{4-[1-(4-methoxy-3-methyl-phenyl)-ethyl]-piperazin-1-yl}-methanone; (4-chloro-phenyl)-{4-[1-(4-methoxy-naphthalen-1-yl)-ethyl]-piperazin-1-yl}-methanone; 4-trifluoromethyl-phenyl)-{4-[1-(4-methoxy-2,3-dimethyl-phenyl)-propyl]-piperazin-1-yl}-methanone; (4-chloro-phenyl)-{4-[1-(4-methoxy-2,3-dimethyl-phenyl)-allyl]-piperazin-1-yl}-methanone; 4-fluoro-phenyl)-{4-[1-(4-methoxy-2,3-dimethyl-phenyl)-ethyl]-piperazin-1-yl}-methanone; 4-bromo-3-methyl-phenyl)-{4-[1-(4-methoxy-2,3-dimethyl-phenyl)-ethyl]-piperazin-1-yl}-methanone; (3,4-dichloro-phenyl)-{4-[1-(4-methyl-naphthalen-1-yl)-ethyl]-piperazin-1-yl}-methanone; [6-(3,4-dimethoxy-phenyl)-octahydro-pyrido[1,2-a]pyrazin-2-yl]-(4-trifluoromethyl-phenyl)-methanone; 4-chloro-phenyl)-{4-[1-(4-methoxy-2,3-dimethyl-phenyl)-propyl]-piperazin-1-yl}-methanone; {4-[1-(4-methoxy-2,3-dimethyl-phenyl)-ethyl]-[1,4]diazepan-1-yl}-(4-trifluoromethyl-phenyl-methanone; and {5-[1-4-methoxy-2,3-dimethyl-phenyl)-ethyl]-2,5-diaza-bicyclo[2.2.1]hept-2-yl}-(4-trifluoromethyl-phenyl)-methanone.

Representative compounds in which U is nitrogen or oxygen include, for example: 3-{1-[4-(4-bromo-3-methoxyphenyl)-piperazin-1-yl]-ethyl}-6-methoxy-quinoline; 3-{1-[4-(4-bromo-3-methoxy-phenyl)-piperazin-1-yl]-ethyl}-2-chloro-6-methoxy-quinoline; 3-{1-[4-(4-bromo-3-methoxy-phenyl)-piperazin-1-yl]-ethyl}-quinoline; 1-(4-bromo-3-methoxy-phenyl)-4-[1-(6-methoxy-pyridin-3-yl)-ethyl]-piperazine; and 3-{1-[4-(4-Bromo-3-methoxy-phenyl)-piperazin-1-yl]-ethyl}-6-fluoro-4-methyl-2H-chromen-2-ol.

Representative chiral compounds provided herein include, for example, (3S)-1-(4-chloro-3-trifluoromethoxyphenyl)-4-[1-(3,4-dimethoxy-benzyl)]-2-methyl-piperazine; (2S)-4-(5-bromo-6-methoxypyridin-2-yl)-1-(3,4-dimethoxy-benzyl)-2-methylpiperazine; R-1-(4-chloro3-methoxyphenyl)-4-[1-(3,4-dimethoxyphenyl)ethyl]piperazine; S-1-(4-chloro-3-methoxyphenyl)-4-[1-(3,4-dimethoxyphenyl)ethyl]piperazine; R-1-(4-bromo-3-trifluoromethoxyphenyl)-4-[1-(3-fluoro-4-methoxyphenyl)ethyl]piperazine; S-1-(4-bromo-3-trifluoromethylphenyl)-4-[1-(3-fluoro-4-methoxyphenyl)ethyl]piperazine; S-1-(4-methoxy-phenyl)-4-[1-(3,4-dimethoxyphenyl)ethyl]piperazine; R-1-(4-methoxylphenyl)-4-[1-(3,4-dimethoxyphenyl)ethyl]piperazine; R-1-(4-chloro-3-methoxy-phenyl)-4-[1-(3,4-dimethoxy-phenyl)-ethyl]-piperazine; {5-[1-4-methoxy-2,3-dimethyl-phenyl)-ethyl]-(1S,4S)-2,5-diaza-bicyclo[2.2.1]hept-2-yl}-(4-trifluoromethyl-phenyl)-methanone; (6R,10S)-2-(4-chloro-3-methoxy-phenyl)-6-(3,4-dimethoxy-phenyl)-octahydro-pyrido[1,2-a]pyrazin-8-one; R-1-(4-bromo-3-methoxyphenyl)-4-[1-(3,4-dimethoxyphenyl)-ethyl]piperazine; (2S)-4-(4-chloro-3-methoxyphenyl)-1-(3,4-dimethoxybenzyl)-2-methyl-piperazine; (2R)-4-(4-chloro-3-methoxyphenyl)-1-(3,4-dimethoxybenzyl)-2-methyl-piperazine; (3R)-1-(4-fluoro-3-trifluoromethyl-phenyl)-4-[1-(3,4-dimethoxyphenyl)-ethyl]-piperazine; (3S)-1-(4-fluoro-3-trifluoromethyl-phenyl)-4-[1-(3,4-dimethoxyphenyl)-ethyl]-piperazine; (3R)-1-(4-chloro-3-trifluoromethyl-phenyl)-4-[1-(3,4-dimethoxyphenyl)-ethyl]-piperazine; (3S)-1-(4-chloro-3-trifluoromethyl-phenyl)-4-[1-(3,4-dimethoxyphenyl)-ethyl]-piperazine; (6R,10S)-2-(4-chloro-3-methoxy-phenyl)-6-(3,4-dimethoxy-phenyl)-octahydro-pyrido[1,2-a]pyrazine; (3R)-1-(4-fluoro-3-methoxy-phenyl)-4-[1-(3,4-dimethoxyphenyl)-ethyl]-piperazine; (2R)-4-(4-chloro-3-trifluoromethylphenyl)-[1-(3,4-dimethoxybenzyl)-ethyl]-piperazine; (6R,9S)-2-(4-chloro-3-methoxy-phenyl)-6-(3,4-dimethoxy-phenyl)-octahydro-pyrrolo[1,2-a]pyrazine; (6R,10S)-2-(4-chloro-3-methoxy-phenyl)-6-(3,4-dimethoxy-phenyl)-octahydro-pyrido[1,2-a]pyrazin-8-ol; (6R,10S)-[6-(3,4-dimethoxy-phenyl)-octahydro-pyrido[1,2-a]pyrazin-2-yl]-(4-trifluoromethyl-phenyl)-methanone; (6R,10S)-2-(4-chloro-3-methoxy-phenyl)-6-(3-fluoro, 4-methoxy-phenyl)-octahydro-pyrido[1,2-a]pyrazine; and {5-[1-4-methoxy-2,3-dimethyl-phenyl)-ethyl]-(1S,4S)-2,5-diaza-bicyclo[2.2.1]hept-2-yl}-(4-trifluoromethyl-phenyl)-methanone.

It will be apparent that the specific compounds recited above are illustrative examples of compounds provided herein, and are not intended to limit the scope of the present invention. As noted above, all compounds of the present invention may be present as a free base or as a pharmaceutically acceptable acid addition salt. In addition, where chirality is not specified, both chiral compounds and racemic mixtures are encompassed by the present invention, although chiral forms as described above may be preferred.

Substituted 1-benzyl-4-aryl piperazine and piperidine analogues provided herein detectably alter (modulate) MCH binding to MCHR1 and/or MCHR2 receptor, as determined using a standard in vitro MCH receptor binding assay and/or calcium mobilization assay. References herein to a "MCH receptor ligand binding assay" are intended to refer to the standard in vitro receptor binding assay provided in Example 2. Briefly, a competition assay may be performed in which an MCH receptor preparation is incubated with labeled (e.g., $^{125}$I) MCH and unlabeled test compound. Within the assays provided herein, the MCH receptor used is preferably a mammalian MCHR1 or MCHR2 receptor, more preferably a human or monkey MCHR1 or MCHR2 receptor. The receptor may be recombinantly expressed or naturally expressed, and may comprise a native sequence or a modified sequence (e.g., truncated and/or fused to a non-native N-terminal sequence). The MCH receptor preparation may be, for example, a membrane preparation from HEK293 cells that recombinantly express a human MCH receptor (e.g., Genbank Accession No. Z86090), monkey MCHR1 receptor (such as the MCHR1 sequence provided in SEQ ID NO:1), or human MCHR1/human beta-2-adrenergic chimeric receptor.

Incubation with a compound that detectably modulates MCH binding to MCH receptor will result in a decrease or increase in the amount of label bound to the MCH receptor preparation, relative to the amount of label bound in the absence of the compound. Preferably, such a compound will exhibit a $K_i$ at an MCH receptor of less than 1 micromolar, more preferably less than 500 nM, 100 nM, 20 nM or 10 nM, within a MCH receptor ligand binding assay performed as described in Example 2. Generally preferred compounds are MCH receptor antagonists, and exhibit $EC_{50}$ values of about 4 micromolar or less, more preferably 1 micromolar or less, still more preferably about 100 nanomolar or less, 10 nanomolar or less or 1 nanomolar or less within a standard in vitro MCH receptor mediated calcium mobilization assay, as provided in Example 3.

If desired, compounds of the present invention may be evaluated for certain pharmacological properties including, but not limited to, oral bioavailability, toxicity, serum protein binding and in vitro and in vivo half-life. In addition, penetration of the blood brain barrier may be desirable for compounds used to treat CNS disorders, while low brain levels of compounds used to treat peripheral disorders may be preferred. Routine assays that are well known in the art may be used to assess these properties, and identify superior compounds for a particular use. For example, assays used to predict bioavailability include transport across human intestinal cell monolayers, including Caco-2 cell monolayers. Toxicity may be assessed using any standard method, such as the assay detecting an effect on cellular ATP production provided in Example 5. Penetration of the blood brain barrier of a compound in humans may be predicted from the brain levels of the compound in laboratory animals given the compound intravenously. Serum protein binding may be predicted from albumin binding assays. Such assays are described in a review by Oravcová, et al. (Journal of Chromatography B (1996) volume 677, pages 1–27). Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

In general, preferred compounds of the present invention do not substantially interact with dopamine receptors, particularly human dopamine D2 and D4 receptors. Dopamine receptor binding assays may be preformed using standard methods, such as the assay described in Example 4. Preferably, compounds exhibit $K_i$ values greater than 1 micromolar within such an assay.

As noted above, MCH receptor modulators provided herein may comprise, in addition to an active compound of Formula I, one or more additional associated moieties. Such moieties may be linked directly (i.e., via a bond) or by way of a linker, may be noncovalently linked or may be combined with the compound. Such additional moieties may be used, for example, to facilitate delivery, targeting or detection of the compound. Such moieties may be linked directly (i.e., via a bond) or by way of a linker. For example, while compounds described above may sufficiently target a desired site in vivo, it may be beneficial for certain applications to include an additional targeting moiety to facilitate targeting to one or more specific tissues. Preferred targeting moieties include, for example, those that target specifically to brain regions associated with MCH activity.

For certain embodiments, it may be beneficial to also, or alternatively, associate a drug with a modulator. As used herein, the term "drug" refers to any bioactive agent intended for administration to a mammal to prevent or treat a disease or other undesirable condition. Drugs include hormones, growth factors, proteins, peptides and other compounds. For example, modulators for treatment of obesity may comprise leptin, a leptin receptor agonist, a melanocortin receptor 4 (MC4) agonist, sibutramine, dexenfluramine, a growth hormone secretagogue, a beta-3 agonist, a 5HT-2 agonist, an orexin antagonist, a neuropeptide $Y_1$ or $Y_5$ antagonist, a galanin antagonist, a CCK agonist, a GLP-1 agonist and/or a corticotropin-releasing hormone agonist. Moieties that facilitate detection include radionuclides, luminescent groups, fluorescent groups and enzymes, any of which may be linked to a compound via standard methods.

For detection purposes, as discussed in more detail below, compounds provided herein may be isotopically-labeled or radiolabeled. Such compounds are identical to those recited in Formulas I, but for the fact that one or more atoms are replaced by an atom having an atomic mass or mass number different from the atomic mass or mass number most commonly found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Other moieties that may be associated with an active compound include carriers. Such substances may modulate bioavailability or stability of the compound. Representative carriers include, for example, molecules such as albumin, polylysine, polyamidoamines, peptides, proteins, polystyrene, polyacrylamide, lipids, ceramide and biotin, solid support materials such as beads and microparticles comprising, for example, polylactate, polyglycolate, poly(lactide-co-glycolide), polyacrylate, latex, starch, cellulose or dextran.

Preparation of MCH Receptor Modulators

Compounds provided herein may generally be prepared using standard synthetic methods. Starting materials are generally readily available from commercial sources, such as Sigma-Aldrich Corp. (St. Louis, Mo.). For example, a synthetic route similar to that shown in any one of Schemes A to K may be used. It will be apparent that the final product, and any intermediate(s) shown in the following schemes may be extracted, dried, filtered and/or concentrated, and may be further purified (e.g., by chromatography). Further experimental details for synthesis of representative compounds via these schemes are provided in Example 1, herein.

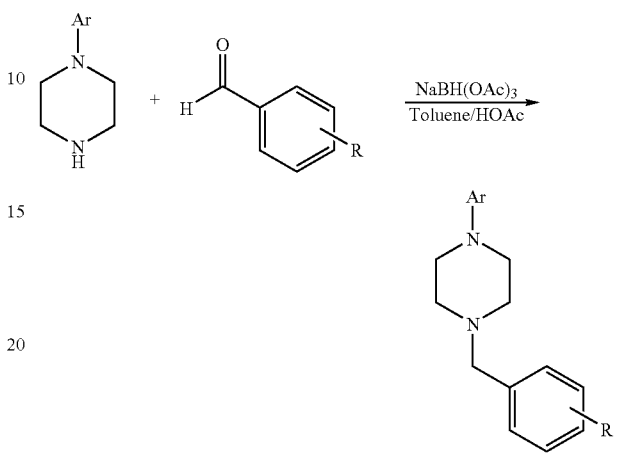

Briefly, one equivalent each of substituted piperazine and benzaldehyde are reacted with an excess of NaBH(OAc)$_3$ under a nitrogen atmosphere until no starting material is detectable by TLC. At that time, the reaction is quenched with saturated aqueous NaHCO$_3$ and extracted with ethyl acetate to yield the 1-benzyl-4-aryl piperazine analogue. Extracts may be dried over anhydrous MgSO$_4$, concentrated in vacuo and chromatographed.

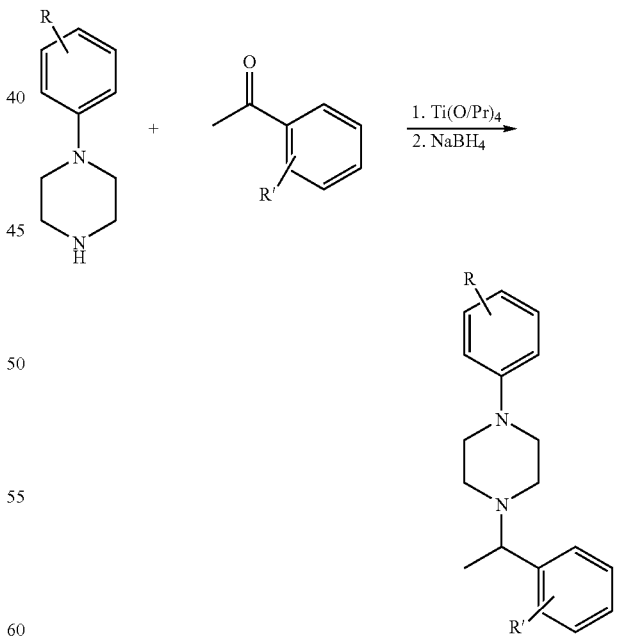

Briefly, one equivalent each of substituted piperazine and acetophenone are heated with Ti(OiPr)$_4$ (e.g., 70° C. for 2 hours). The reaction solution is cooled and reacted with NaBH$_4$ to yield the 1-benzyl-4-aryl piperazine analogue. The reaction is quenched by the addition of 1 N NaOH and may be extracted with CH$_2$Cl$_2$. CH$_2$Cl$_2$ extracts may be dried over anhydrous MgSO$_4$, concentrated in vacuo, and subjected to chromatography.

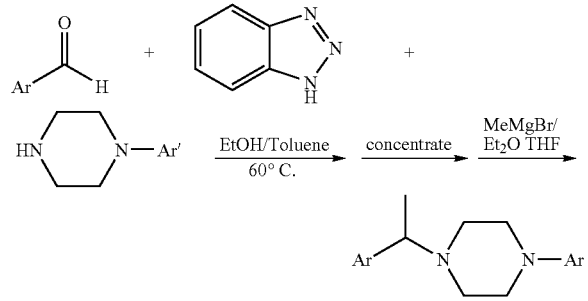

Briefly, a solution containing an aromatic carboxaldehyde, benzotriazole and an aromatic piperazine in ethanol/toluene is heated and the solution is concentrated. Residue is coevaporated with toluene, then dissolved in THF and treated with methyl magnesium bromide in diethyl ether to yield the 1-benzyl-4-aryl piperazine analogue.

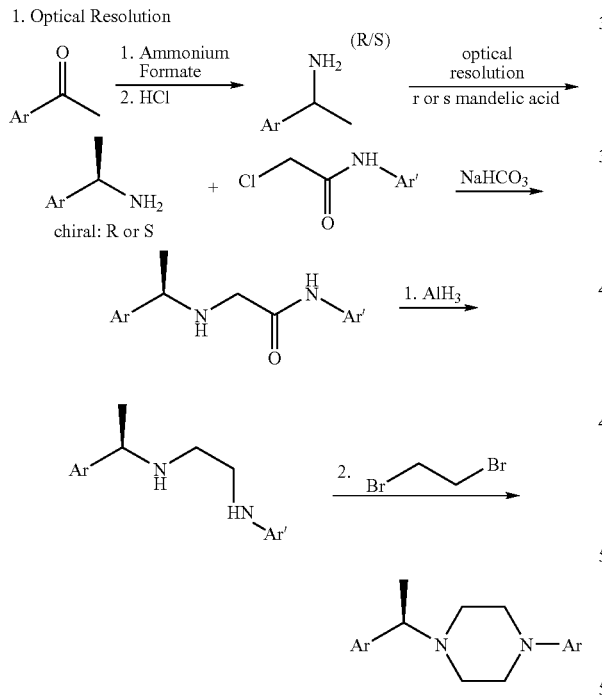

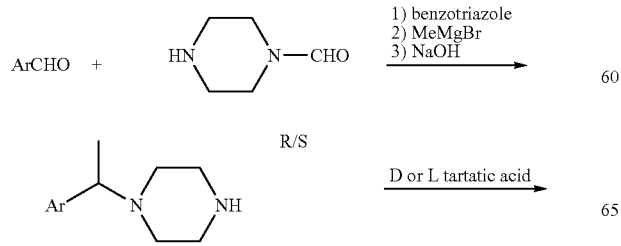

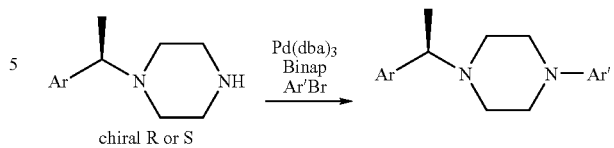

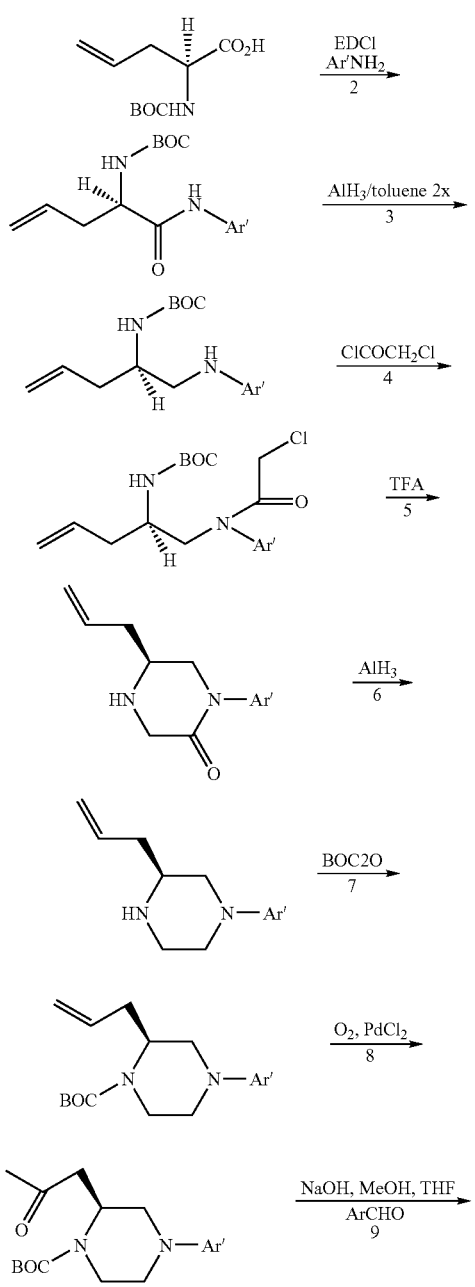

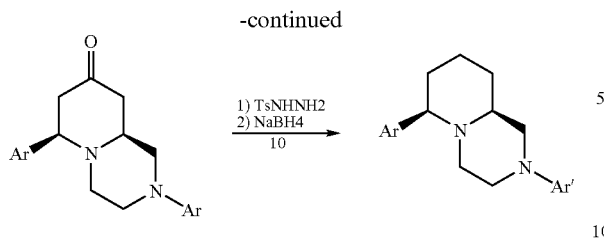

Briefly, di-t-butyl dicarbonate is reacted with L-2-aminopent-4-enoic acid in 1N NaOH and dioxane, and then concentrated (step 1). The aqueous residue is chilled on ice, layered with EtOAc and acidified. In step 2, the reaction product, 1-(3-dimethylaminopropyl)-3-ethylcarbodiimide hydrochloride (EDCI), and an aniline are combined in pyridine. In step 3, alane-N,N-dimethylethylamine complex in toluene is added. Chloroacetylchloride is added in step 4, and the layers are separated. In step 5, trifluoroacetic acid is added, and alane-N,N-dimethylethylamine complex in toluene is added in step 6. In step 7, the reaction product is reacted with di-t-butyldicarbonate. Palladium (II) chloride and copper (I) chloride are added in step 8, and oxygen gas is bubbled into the solution. In step 9, trifluoroacetic acid is added, and the reaction stirred on ice and then concentrated. To this solution is added a benzaldehyde derivative and NaOH. p-toluenesulfonylhydrazide, followed by sodium borohydride (step 10) is then added. It will be apparent that extraction, drying, filtration, concentration, and purification steps may be needed at various points in this scheme, as illustrated in Example 1, subpart V.

Scheme F (Alternate Synthesis of Octahydro-pyrido[1,2-a]pyrazine Derivatives)

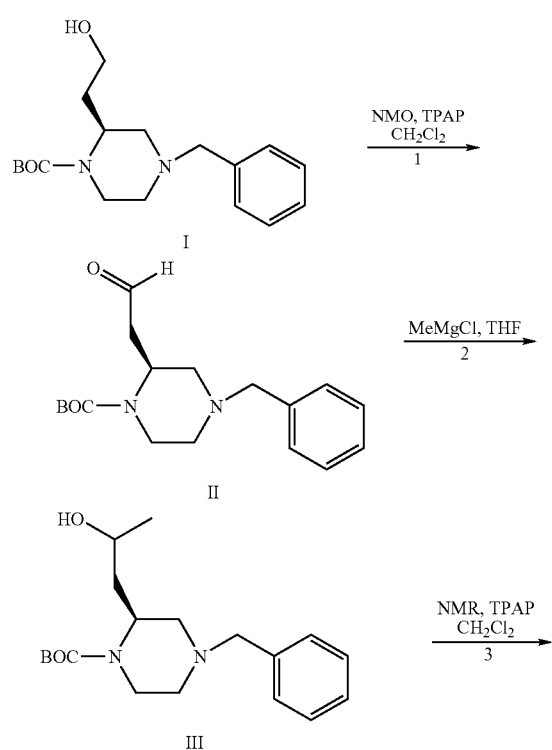

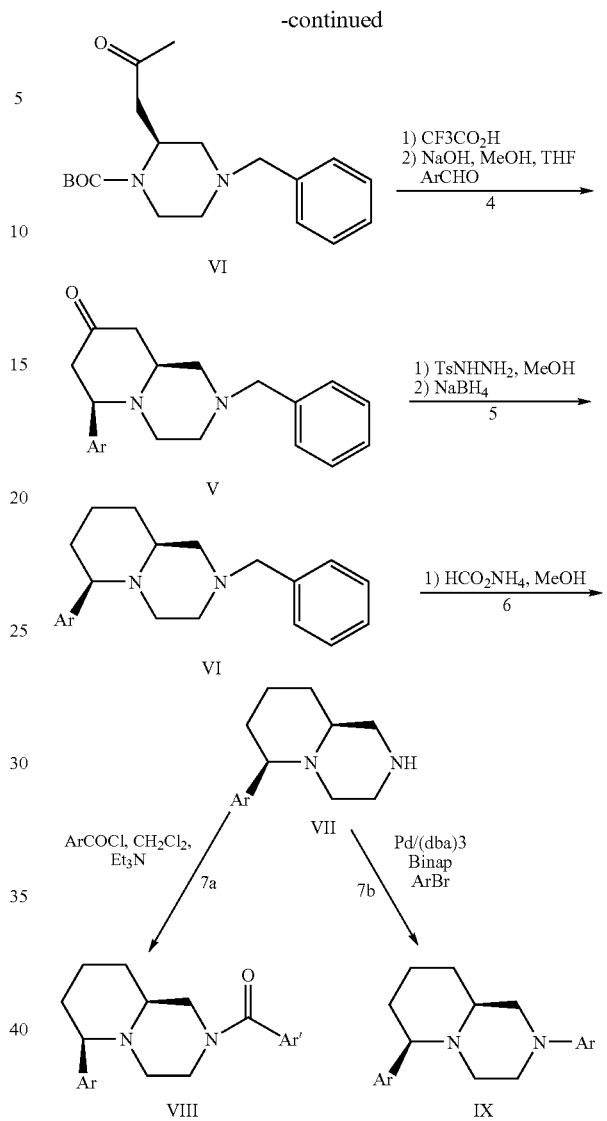

Briefly, 2-(4-benzyl-piperazin-2-yl)-ethanol is initially reacted with di-tert-butyl dicarbonate (BOC anhydride) to yield 4-benzyl-2-(2-hydroxy-ethyl)-piperazine-1-carboxylic acid tert-butyl ester (I). In step 1, I is dissolved in anhydrous dichloromethane containing previously activated 4 Å molecular sieves and 4-methylmorpholine N-oxide. The reaction is started by addition of tetrapropylammonium perruthenate and allowed to proceed until LC/MS analysis shows no detectable remaining starting material (typically about 1 hour). The suspension is filtered and 4-benzyl-2-(2-oxo-ethyl)-piperazine-1-carboxylic acid tert-butyl ester (II) is eluted with 5% methanol in chloroform. In step 2, II is dissolved in anhydrous tetrahydrofuran under nitrogen, and methyl magnesium bromide is added to yield 4-benzyl-2-(2-hydroxy-propyl)-piperazine-1-carboxylic acid tert-butyl ester (III). In step 3, III is treated as described above for I, yielding 4-benzyl-2-(2-oxo-propyl)-piperazine-1-carboxylic acid tert-butyl ester (IV). In step 4, trifluoroacetic acid is added to IV in dichloromethane. Subsequent reaction with a benzaldehyde derivative (ArCHO) and NaOH yields compound V. In step 5, compound V is reacted with p-toluene-sulfonylhydrazide in methanol. Sodium borohydride is added and the reaction incubated until completion, as determined by TLC analysis (e.g., about 18 hours) to yield compound VI. In step 6, compound VI is heated with 10% Pd/C and ammonium formate (e.g., under reflux for 6 hours). Additional ammonium formate may be added, and the reaction stirred under reflux (e.g., for a further 15 hours) to afford compound VII. Compound VII may then be dissolved in dichloromethane and stirred with triethylamine and trifluoromethylbenzoylchloride at room temperature (step 7a).

Extraction with ethyl acetate affords compound VIII, which may be purified on 250 micron analytical TLC. Alternatively (step 7b), compound VII may be used to generate compound IX.

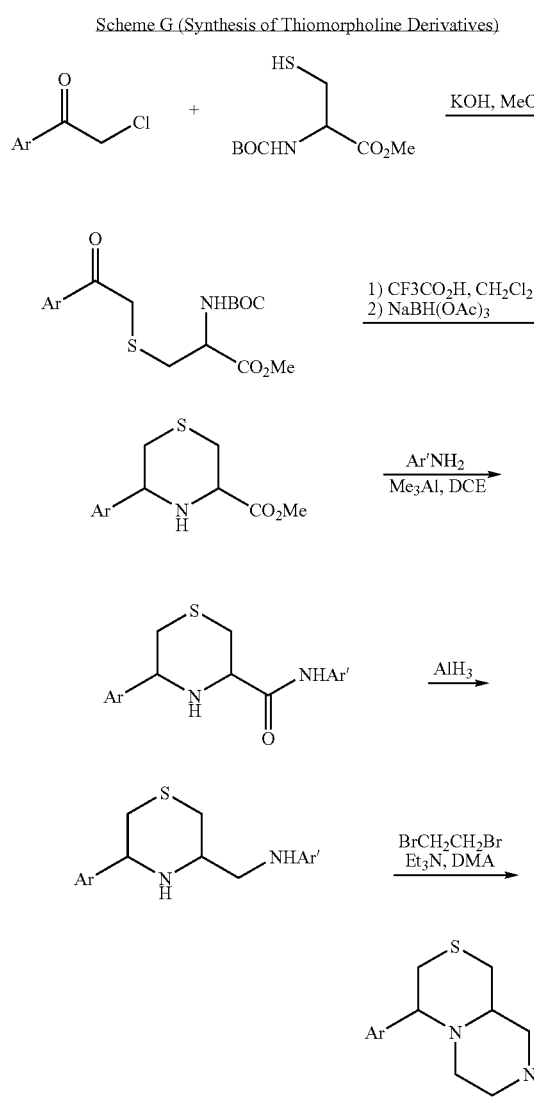

Briefly, 2-tert-butoxycarbonylamino-3-mercapto-propionic acid methyl ester is treated with potassium hydroxide in methanol. To the reaction, a solution of 2-chloro-aryl-etha-none is added. Trifluoroacetic acid is then added, followed by sodium triacetoxyborohydride, to yield the thiomorpholine. Reaction with trimethylaluminum and an aniline produces the amide, which is reduced using alane. Treatment with dibromoethane and triethylamine yields the octahydropyrazino thiazine derivative.

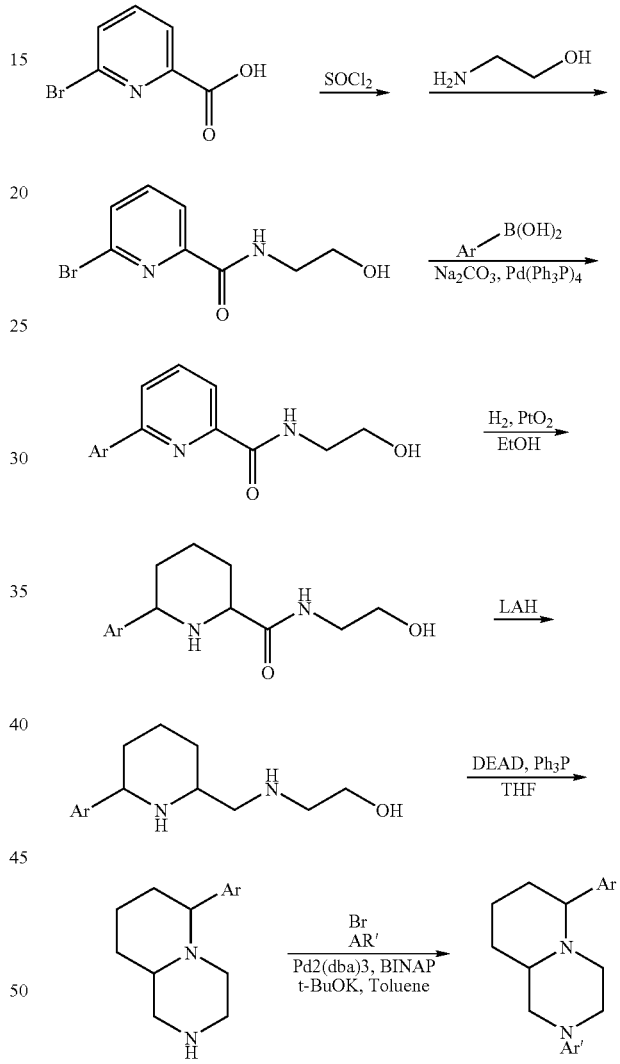

Briefly, 5-Bromo-picolinic acid is reacted with thionyl chloride, followed by hydroxyl ethylamine to yield the amide. The amide is then reacted with an aryl boronic acid and tris(dibenzylideneacetone)-dipalladium(0) until TLC shows no detectable starting material. Treatment with platinum dioxide results in the piperidine compound, which is reduced using $LiAlH_4$. Ring formation is achieved using triphenyl phosphine and diethyl azodicarboxylate until there is no detectable starting material shown on TLC. Finally, an aryl substituent is added by reaction with a bromo-aryl compound.

Scheme I - Analogs from Ketones
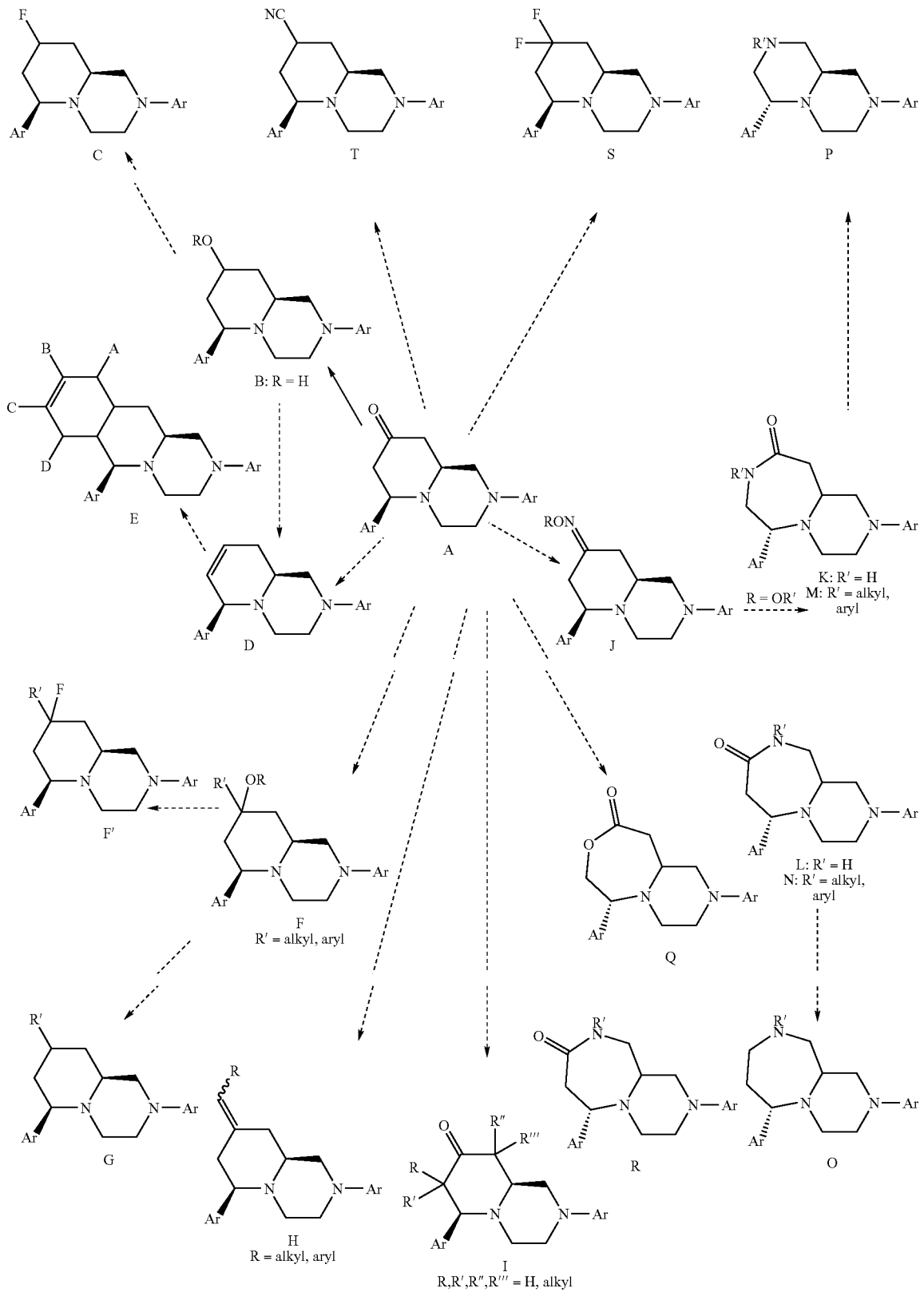

Briefly, reduction of ketone A to secondary alcohol B can be accomplished by a variety of methods known to those skilled in the art, which include (but are not limited to) reaction with sodium borohydride in methanol, as described in Example 1. Fluorination of secondary alcohols B to the secondary alkyl fluorides C can be accomplished by a variety of methods known to those skilled in the art, such as reaction with diethylaminosulfurtrifluoride (DAST, Hudlicky, Org. React. 1988, 35, 513) in solvents such as dichloromethane or chloroform, at temperatures between −78° C. and 120° C. Dehydration of a secondary alcohol B to the corresponding olefin D can be carried out by a variety of well-known methods, including (but not limited to) reaction with reagents such as $OPCl_3$ or $PCl_5$ in solvents such as pyridine, at temperatures between 0° C. and 200° C. Transformation of olefins D into carbo-and heterocycles such as E can be realized by the Diels-Alder reaction, well known to those of ordinary skill in the art (e.g., L. W. Butz and A. W. Rytina, Org. React 1949, 5, 136; M. C. Kloetzel, Org. React. 1948, 4, 1). These reactions can be carried out by reacting D with a diene such as, but not limited to, 1,3-butadiene, 2,3-dimethylbutadiene, 1,3-cyclohexadiene, 1-methoxy-3-trimethylsiloxy-1,3-butadiene ("Danishefsky's diene", S. Danishefsky and T. Kitahara, J. Am. Chem. Soc. 1974, 96, 7807), o-quinodimethane, diphenylbenzo[c] furan, or antracene.

Transformation of the ketone A into tertiary alcohols of generic structure F can be accomplished by reaction with the appropriate organometallic reagents such as, but not limited to, alkyl or aryllithium, alkyl or arylmagnesium halides, alkyl or arylsodium, alkyl or aryl potassium, etc, in solvents such as, but not limited to, tetrahydrofuran, ethyl ether, methyl-tert-butyl ether, diisopropyl ether, benzene, toluene, or hexanes, at temperatures between −78° C. and the corresponding boiling point of the reaction mixture. Direct conversion of the tertiary alcohols F to the corresponding tertiary fluorides F' can be accomplished by a variety of methods known to those skilled in the art, which include but are not limited to, reaction with diethylaminosulfurtrifluoride in solvents such as dichloromethane or chloroform, at temperatures between −78° C. and 120° C. Deoxygenation of tertiary alcohols F to the corresponding alkanes G can be carried out in a number of ways, which include treatment with triethylsilane (or equivalent hydrogen donor) in the presence of a Broensted acid (e.g., trifluoroacetic acid) or a Lewis acid (e.g., boron trifluoride) in solvents such as dichloromethane, hexanes or ethyl ether, at reaction temperatures in the range −78° C. to the boiling point of the corresponding reaction mixtures. Transformation of ketone A into a variety of substituted oximes of generic structure J can be carried out by a number of methods known to those skilled in the art. These include but are not limited to, reaction of A with hydroxylamine hydrochloride, O-methyl hydroxylamine hydrochloride, O-benzyl hydroxylamine hydrochloride, etc., in a solvent such as, but not limited to, methanol, ethanol, pyridine, N,N-dimethylformamide, dimethylsulfoxide or acetonitrile, in the presence of a base such as triethylamine, sodium carbonate, or sodium hydroxide, at reaction temperatures between −5° C. and the boiling point of the reaction mixture. The corresponding oxime J (R=H) can be rearranged to the lactam K or L by a variety of methods known to those skilled in the art (e.g., Beckmann rearrangement; Donaruma, L. G. and Heldt, W. Z. Org. React. 1960, 11, 1). These include, but are not limited to, treatment with a dehydrating agent such as $PCl_5$, TsCl, sulfuric acid and the like. Lactams K and L can be subsequently reduced to the corresponding homopiperazines O and P, respectively, as those skilled in the art will recognize. Methods used for these transformations include, but are not limited to, treatment with a reducing agent such as lithium aluminum hydride, alane, borane, sodium bis(2-methoxyethoxy)aluminum hydride (Vitride, Red-Al®), in an appropriate solvent such as tetrahydrofuran, ethyl ether, toluene, etc., at reaction temperatures between −78° C. and the boiling point of the reaction mixture (e.g., M. Hudlicky; Reductions in Organic Chemistry; Ellis Horwood Ltd.; Great Britain, 1984, pp 168.) In addition, lactams K and L can be N-alkylated or N-arylated to the corresponding N-substituted lactams M and N, respectively. This transformation can be carried out by treatment with a strong base such as, but not limited to, sodium hydride, potassium hydride, lithium tetramethylpiperidide, or potassium tert-butoxide, followed by treatment with an appropriate alkyl, aryl or heteroaryl halide, such as but not limited to, methyl iodide, ethyl iodide, benzyl bromide, 2-fluoronitrobenzene, 2-chloro-5-trifluoromethylpyridine, in the presence of a catalyst such as, but not limited to, sodium iodide, potassium iodide or tetramethylammonium iodide, in an appropriate solvent such as, but not limited to, tetrahydrofuran, acetonitrile, dimethylsulfoxide, N,N-dimethylformamide, tert-butanol, at reaction temperatures between −78° C. and the boiling point of the corresponding reaction mixture.

Olefination of ketone A to substituted olefins H can be realized by a variety of chemical reactions known to those skilled in the art. Among these are phosphorus ylides (Wittig reagents) which can be prepared by deprotonation of phosphonium salts, which are themselves prepared by the reaction of triphenylphosphine and alkyl halides (e.g., F. A. Carey and R. J. Sundberg; Advanced Organic Chemistry, Part B, Plenum Press, New York, 1983, pp 71). Alkyl halides include, but are not limited to, methyl iodide, ethyl iodide, benzyl bromide, ethyl bromoacetate, methyl 2-bromopropionate, etc. The bases needed for the deprotonation reaction include, but are not limited to, sodium hydroxide, sodium hydride, lithium diisopropylamide, potassium tert-butoxide, n-butyllithium and tert-butyllithium. Appropriate solvents for these reactions include, but are not limited to, water, methanol, ethanol, tetrahydrofuran, dimethylsulfoxide, benzene or ethyl ether. Reactions can be carried out at reaction temperatures between −78° C. and the boiling point of the corresponding reaction mixture.

α-Alkylation of ketone A to mono-or polyalkylated ketone I can be accomplished by treatment of A with a base and an alkylating agent in an appropriate solvent. Suitable bases include, but are not limited to, lithium diisopropylamide, lithium hexamethyldisilazide, potassium tert-butoxide, sodium methoxide and lithium 2,2,6,6-tetramethylpiperidide. Alkylating reagents include, but are not limited to, methyl iodide, ethyl iodide, 2-iodopropane, methyl orthoformate, benzyl bromide, and phenethyl bromide. Suitable solvents include, but are not limited to, tetrahydrofuran, dimethylsulfoxide, N,N-dimethylformamide, tert-butanol and methanol. Reaction temperatures range from −78° C. to the boiling point of the reaction mixture.

Conversion of ketone A to lactones Q and R can be accomplished by those skilled in the art by means of the Baeyer-Villiger reaction. This reaction involves the treatment of A with an oxidant such as, but not limited to, hydrogen peroxide, peroxybenzoic acid, peroxyacetic acid or m-chloroperoxybenzoic acid in a solvent such as, but not limited to, dichloromethane, chloroform, benzene, at temperatures ranging from −30° C. to the boiling point of the reaction mixture.

Transformation of ketone A to gem-difluoride S can be accomplished, for example, by treatment with diethylaminosulfurtrifluoride in solvents such as dichloromethane or chloroform, at temperatures between −78° C. and 120° C.

Transformation of ketone A into nitrile T can be accomplished by a variety of methods known to those skilled in the art. One example of such conditions is reaction with tosylmethylisocyanide in the presence of a base such as, but not limited to, potassium tert-butoxide, in solvents such as 1,2-dimethoxyethane at temperatures between 10° C. and the boiling point of the solvent (see, e.g., O. H. Oldenziel et al., *J. Org. Chem.* 1977, 42, 3114).

Scheme I
(Synthesis of Octahydro-pyrrolo[1,2-a]pyrazine Derivatives via 6,5 Bicycle Synthesis)

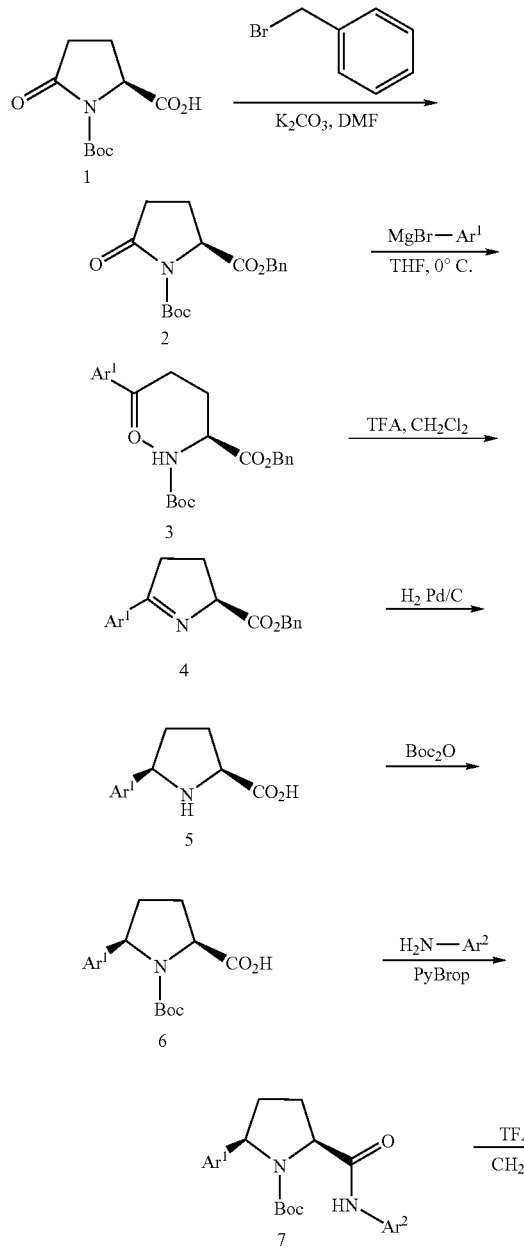

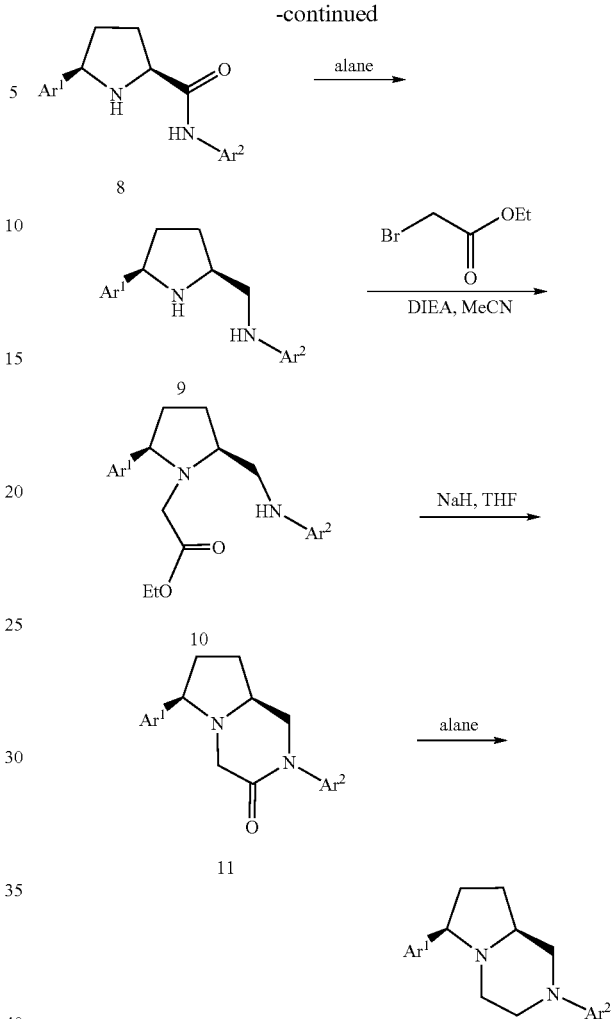

Briefly, the BOC protected 5-oxo-pyrroldine-1,2-dicarboxylatic acid (1) is converted to the benzyl ester (2) with one equivalent of benzyl bromide and 2.5 equivalents of potassium carbonate. Grignard addition of aryl magnesium bromide in THF (e.g., at 0° C. for 2 hours) followed by aqueous work-up provides the ketone, 2-tert-butoxycarbonylamino-5-aryl-5-oxo-pentanoic acid benzyl ester (3). Deprotection and cyclization is conducted by treatment with trifluoroacetic acid in dichloromethane at (e.g., at 0° C. followed by slow warming to room temperature over 2 hours). Basification with 1N NaOH to pH 7 and organic extraction provides 5-aryl-3,4-dihydro-2H-pyrrole-2-carboxylic acid benzyl ester TFA salt (4). Hydrogenation at 50 psi in methanol with Pd/C catalyst (e.g., for 15 hours) provides 5-aryl-pyrrolidine-2-carboxylic acid TFA salt (5). Amine protection with di-t-butyldicarbonate in dichloromethane and diisopropylethylamaine and coupling to an aromatic amine with pyBrop and diisopropylethylamine provides the amide, tert-butyl ester (7). Boc cleavage with trifluoroacetic acid followed by alane reduction provides the diamine (9). Alkylation with ethylbromoacetate provides the aminoester which is cyclized with sodium hydride in THF to give the lactam (11). Reduction of the lactam provides the final product (12).

Scheme K
(piperazine benzamide synthesis)

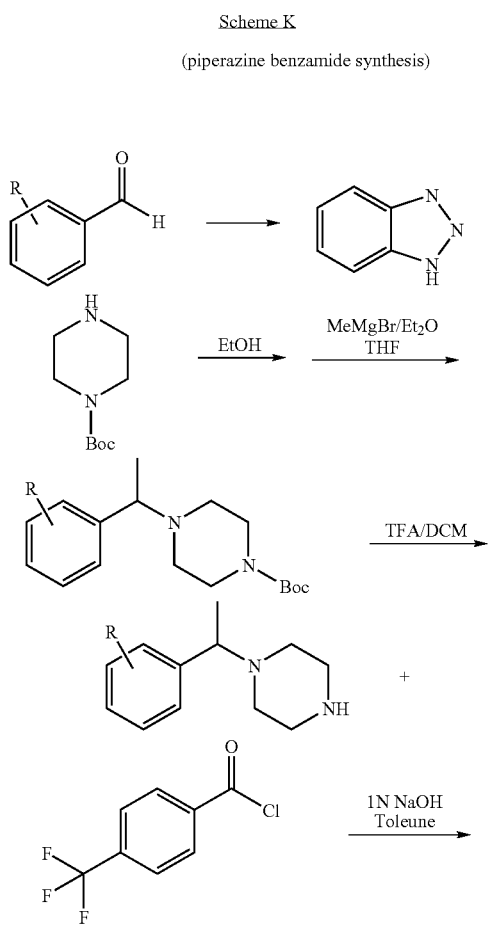

Briefly, 1 equivalent each of optionally substituted benzaldehyde, piperazine-1-carboxylic acid tert-butyl ester and benzotriazole are reacted to yield the optionally substituted phenyl-ethyl-piperazine-1-carboxylic acid tert-butyl ester. Reaction with trifluoroacetic acid and dichloromethane results in optionally substituted phenyl-ethyl-piperazine. Subsequent reaction with an optionally substituted benzoyl chloride yields the benzamide.

Scheme L
(olefin metathesis)

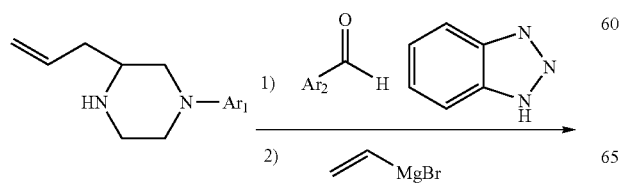

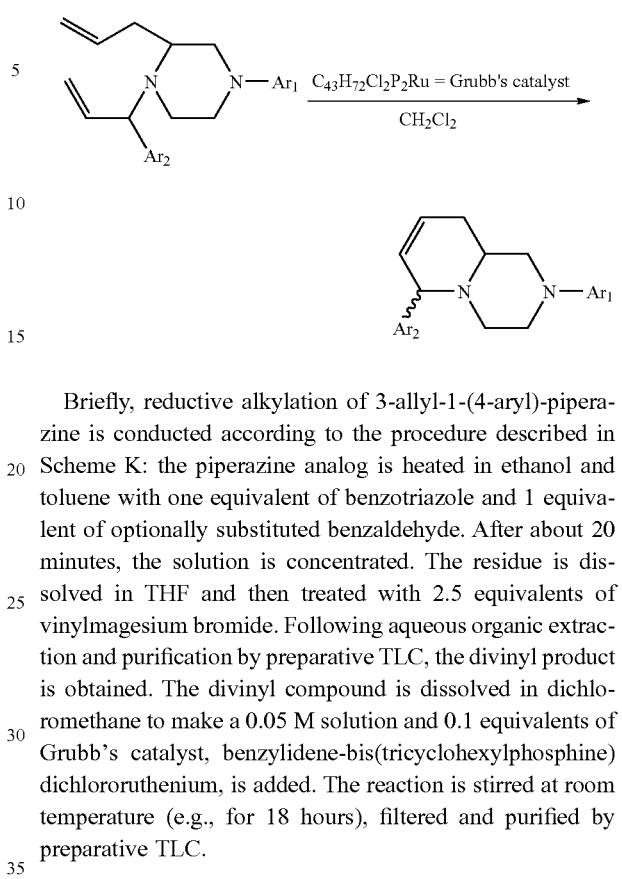

Briefly, reductive alkylation of 3-allyl-1-(4-aryl)-piperazine is conducted according to the procedure described in Scheme K: the piperazine analog is heated in ethanol and toluene with one equivalent of benzotriazole and 1 equivalent of optionally substituted benzaldehyde. After about 20 minutes, the solution is concentrated. The residue is dissolved in THF and then treated with 2.5 equivalents of vinylmagesium bromide. Following aqueous organic extraction and purification by preparative TLC, the divinyl product is obtained. The divinyl compound is dissolved in dichloromethane to make a 0.05 M solution and 0.1 equivalents of Grubb's catalyst, benzylidene-bis(tricyclohexylphosphine) dichlororuthenium, is added. The reaction is stirred at room temperature (e.g., for 18 hours), filtered and purified by preparative TLC.

Scheme M
(Pyrazinol[1,2-a]quinoxalin-5-one Derivatives)

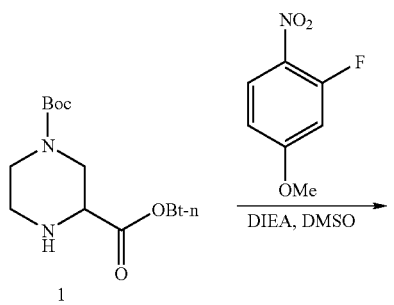

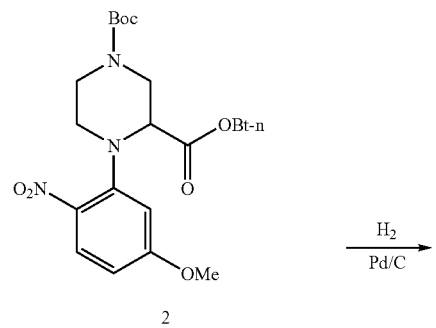

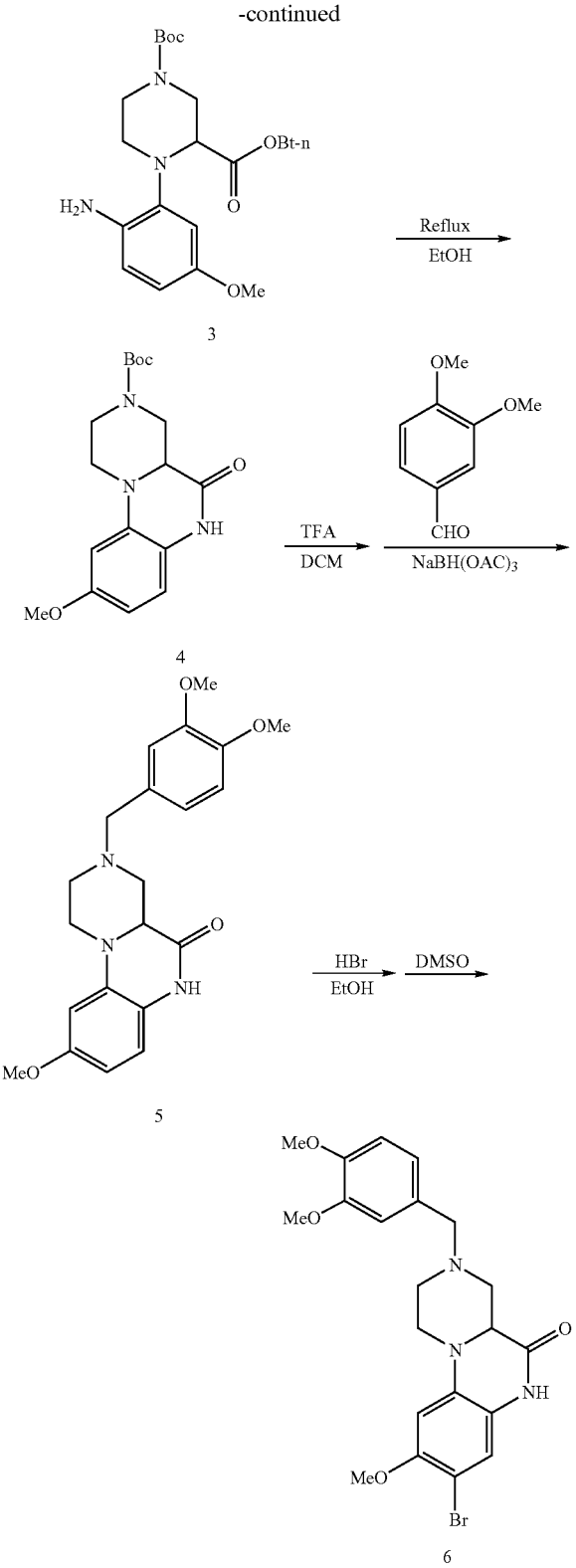

Briefly, a nitro-substituted aromatic ring linked to the piperazine ester (1) to generate compound 2. Reduction of the nitro substituent yields the amine (3), which is cyclized. Addition of a second aromatic group results in compound 5. Optionally, additional ring substituents may be added (e.g., to generate compound 6). It will be apparent that the specific aromatic groups shown above are representative only, and are not intended to limit the scope of such groups that may be used within compounds of the present invention.

In certain situations, compounds of the present invention may contain one or more asymmetric carbon atoms, so that the compounds can exist in different stereoisomeric forms. These compounds can be, for example, racemates or optically active forms. As noted above, all stereoisomers are encompassed by the present invention. Nonetheless, it may be desirable to obtain single enantiomers (i.e., optically active forms). Standard methods for preparing single enantiomers include asymmetric synthesis and resolution of the racemates. Resolution of the racemates can be accomplished, for example, by conventional methods such as crystallization in the presence of a resolving agent, or chromatography using, for example a chiral HPLC column. As noted above, for compounds having an alpha-methyl benzyl group ($R_3$ is methyl, $R_4$ is hydrogen) the R enantiomer is generally preferred. Asymmetric synthesis of such compounds may be performed using the methods illustrated in Scheme D and Example 1, herein.

As noted above, the present invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art recognize further pharmaceutically acceptable salts for the compounds provided herein, including those listed by *Remington's Pharmaceutical Sciences,* 17th ed., Mack Publishing Company, Easton, Pa., p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Prodrugs of the compounds provided herein may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhiydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Additional moieties may be associated with a compound using any suitable procedure. Covalent attachment may generally be achieved using suitable functional groups (e.g., hydroxyl, carboxyl, sulfhydryl or amino groups) on the compound and additional moiety. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. The use of bifunctional, multifunctional and/or cleavable linkers may also be desirable for certain applications. Such linkers are well known in the art. Compounds associated with carriers may be covalently linked or, preferably, such association does not involve covalent interaction and is achieved by mixing.

Compounds may be radiolabeled by carrying out their synthesis using precursors comprising at least one atom that is a radioisotope, such as carbon (preferably $^{14}C$), hydrogen (preferably $^{3}H$), sulfur (preferably $^{35}S$) or iodine (preferably $^{125}I$). Synthesis of such radiolabeled compounds may be conveniently performed by a radioisotope supplier specializing in custom synthesis of radiolabeled probe compounds, such as Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif. Tritium-labeled compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed above using the compound as substrate. In addition, certain precursors may be subjected to tritium-halogen exchange with tritium gas, tritium gas reduction of unsaturated bonds, or reduction using sodium borotritide.

Pharmaceutical Compositions

The present invention also provides pharmaceutical compositions comprising a MCH receptor modulator as described herein, together with at least one physiologically acceptable carrier or excipient. Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs).

If desired, other active ingredients may also be included. For example, compositions intended for the treatment of eating disorders, particularly obesity and bulimia nervosa, may further comprise leptin, a leptin receptor agonist, a melanocortin receptor 4 (MC4) agonist, sibutramine, dexenfluramine, a growth hormone secretagogue, a beta-3 agonist, a 5HT-2 agonist, an orexin antagonist, a neuropeptide $Y_1$ or $Y_5$ antagonist, a galanin antagonist, a CCK agonist, a GLP-1 agonist and/or a corticotropin-releasing hormone agonist.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the present invention may be formulated as a lyophilizate.

Compositions intended for oral use may further comprise one or more components such as sweetening agents, flavoring agents, coloring agents and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active materials in admixture with excipients suitable for the manufacture of aqueous suspensions. Such excipients are suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspension may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil (e.g., olive oil or arachis oil) or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monoleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectable aqueous or oleaginous suspension. The modulator, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Modulators may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of modulator following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of modulator release. The amount of modulator contained within a sustained release formulation depends upon the site of implantation, the rate and expected duration of release and the nature of the condition to be treated or prevented.

Modulators are generally present within a pharmaceutical composition in a therapeutically effective amount. A therapeutically effective amount is an amount that results in a discernible patient benefit, such as increased healing of a disease or disorder associated with pathogenic MCH receptor, as described herein. A preferred concentration is one sufficient to inhibit the binding of MCH to MCHR1 receptor in vitro. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing, and procedures that are well known in the art.

Pharmaceutical compositions may be packaged for treating disorders responsive to melanin concentrating hormone receptor modulation (e.g., treatment of metabolic disorders such as diabetes, heart disease, stroke, eating disorders such as obesity or bulimia, or sexual disorders such as anorgasmic or psychogenic impotence). Packaged pharmaceutical compositions include a container holding a therapeutically effective amount of at least one MCH receptor modulator as described herein and instructions (e.g., labeling) indicating that the contained composition is to be used for treating a disorder responsive to MCH receptor modulation in the patient.

Methods of Use

Within certain aspects, the present invention provides methods for inhibiting the development of a disease or disorder associated with pathogenic MCH receptor. In other words, therapeutic methods provided herein may be used to treat a disease, or may be used to prevent or delay the onset of such a disease in a patient who is free of detectable disease that is associated with pathogenic MCH receptor. As used herein, a disease or disorder is "associated with pathogenic MCH receptor" if it is characterized by inappropriate stimulation of MCH receptor, regardless of the amount of MCH present locally. Such conditions include, for example, metabolic disorders (such as diabetes), heart disease, stroke, eating disorders (such as obesity and bulimia nervosa), or sexual disorders such as anorgasmic or psychogenic impotence. These conditions may be diagnosed and monitored using criteria that have been established in the art. Patients may include humans, domesticated companion animals (pets, such as dogs) and livestock animals, with dosages and treatment regimes as described above.

Frequency of dosage may vary depending on the compound used and the particular disease to be treated or prevented. In general, for treatment of most disorders, a dosage regimen of 4 times daily or less is preferred. For the treatment of eating disorders, including obesity, a dosage regimen of 1 or 2 times daily is particularly preferred. For the treatment of impotence a single dose that rapidly reaches effective concentrations is desirable. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Within separate aspects, the present invention provides a variety of in vitro uses for the compounds provided herein. For example, such compounds may be used as probes for the detection and localization of MCH receptors, in samples such as tissue sections, as positive controls in assays for receptor activity, as standards and reagents for determining the ability of a candidate agent to bind to MCH receptor, or as radiotracers for positron emission tomography (PET) imaging or for single photon emission computerized tomography (SPECT). Such assays can be used to characterize MCH receptors in living subjects. Such compounds are also useful as standards and reagents in determining the ability of a potential pharmaceutical to bind to melanin concentrating hormone receptor.

Within methods for determining the presence or absence of MCH receptor in a sample, a sample may be incubated with a compound as provided herein under conditions that permit binding of the compound to MCH receptor. The amount of compound bound to MCH receptor in the sample is then detected. For example, a compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect luminescent groups and fluorescent groups). As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of capsaicin receptor in the sample. Detection assays, including receptor autoradiography (receptor mapping) of MCH receptors in cultured cells or tissue samples may be performed as described by Kuhar in sections 8.1.1 to 8.1.9 of Current Protocols in Pharmacology (1998) John Wiley & Sons, New York.

Modulators provided herein may also be used within a variety of well known cell culture and cell separation methods. For example, modulators may be linked to the interior surface of a tissue culture plate or other cell culture support, for use in immobilizing MCH receptor-expressing cells for screens, assays and growth in culture. Such linkage may be performed by any suitable technique, such as the methods described above, as well as other standard techniques. Modulators may also be used to facilitate cell identification and sorting in vitro, permitting the selection of cells expressing a MCH receptor. Preferably, the modulator(s) for use in such methods are labeled as described herein. Within one preferred embodiment, a modulator linked to a fluorescent marker, such as fluorescein, is contacted with the cells, which are then analyzed by fluorescence activated cell sorting (FACS).

Within other aspects, methods are provided for modulating binding of MCH to an MCH receptor in vitro or in vivo, comprising contacting a MCH receptor with a sufficient amount of a modulator provided herein, under conditions suitable for binding of MCH to the receptor. Preferably, within such methods, MCH binding to receptor is inhibited by the modulator. The MCH receptor may be present in solution, in a cultured or isolated cell preparation or within a patient. Preferably, the MCH receptor is a MCHR1 receptor present in the hypothalamus. In general, the amount of compound contacted with the receptor should be sufficient to modulate MCH binding to MCH receptor in vitro within, for example, a binding assay as described in Example 2. MCH receptor preparations used to determine in vitro binding may be obtained from a variety of sources, such as from HEK 293 cells or Chinese Hamster Ovary (CHO) cells transfected with a MCH receptor expression vector, as described herein.

Also provided herein are methods for modulating the signal-transducing activity of cellular MCH receptors, by contacting MCH receptor, either in vitro or in vivo, with a sufficient amount of a modulator as described above, under conditions suitable for binding of MCH to the receptor. Preferably, within such methods, signal-transducing activity is inhibited by the modulator. The MCH receptor may be present in solution, in a cultured or isolated cell preparation or within a patient. In general, the amount of modulator contacted with the receptor should be sufficient to modulate MCH receptor signal transducing activity in vitro within, for example, a calcium mobilization assay as described in Example 3. An effect on signal-transducing activity may be assessed as an alteration in the electrophysiology of the cells, using standard techniques, such as intracellular patch clamp recording or patch clamp recording. If the receptor is present in an animal, an alteration in the electrophysiology of the cell may be detected as a change in the animal's feeding behavior.

The following Examples are offered by way of illustration and not by way of limitation. Unless otherwise specified all reagents and solvent are of standard commercial grade and are used without further purification.

EXAMPLES

Example 1

Preparation of Representative 1-Benzyl-4-Aryl Piperazines

This Example illustrates the synthesis of representative 1-benzyl-4-aryl piperazines. It will be apparent that, through variation of starting compounds, these methods may be used to prepare a wide variety of such compounds. References to schemes within this Example refer to Schemes A–K, discussed above.

I. 1-(5-bromo-6-methoxypyridin-2-yl)-4-(3,4-dimethoxy-benzyl)piperazine via Scheme A

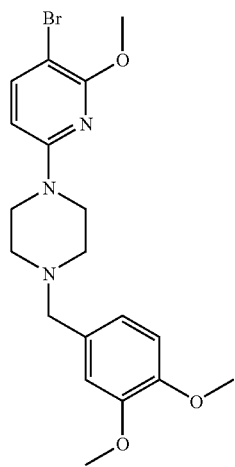

A quantity of 0.1 g (0.4 mmole, 1 eq) of 1-(5-Bromo-6-methoxy-pyridin-2-yl)-piperazine and 0.061 g (0.4 mmole, 1 eq) of 3,4-dimethoxybenzaldehyde is dissolved in 5 mL of anhydrous toluene, and 3 drops of glacial acetic acid is added. An excess of $NaBH(OAc)_3$ is added to the solution and stirred at room temperature under a nitrogen atmosphere until no starting material is detectable by TLC. At that time the reaction is quenched with saturated aqueous $NaHCO_3$ and extracted with ethyl acetate. The ethyl acetate extracts are dried over anhydrous $MgSO_4$ and concentrated in vacuo. The residue is chromatographed on $SiO_2$ with 10% $CH_3OH$ (2M $NH_3$)/$CH_2Cl_2$ to afford 1-(5-bromo-6-methoxypyridin-2-yl)-4-(3,4-dimethoxybenzyl)piperazine (compound 1). Analysis: $^1H$ NMR (400 MHz, DMSO): 7.71 (1H, d), 7.36 (1H, s), 7.05 (2H, m), 6.39 (1H, d), 4.38 (4H, m), 3.80 (9H, m), 3.39 (4H, m), 3.02 (2H, m). MS (LC-MS): Calculated for $C_{19}H_{24}BrN_3O_3$ 422.32, found 436.3424.31 (M+2).

II. 1-(4-Chloro-3-trifluoromethyl-phenyl)-4-[1-(3,4-dimethoxy-phenyl)-ethyl]-piperazine via Scheme B

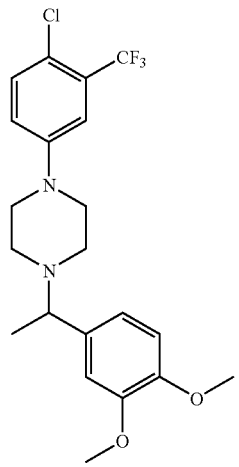

A quantity of 0.17 g (0.6 mmole, 1 eq) of 1-(4-chloro-3-trifluoromethyl-phenyl)-piperazine and 0.1 g (0.6 mmole, 1 eq) of 3,4-dimethoxyacetophenone and 2 mL of $Ti(OiPr)_4$ are warmed to 70° C. for 2 hours. The reaction solution is cooled to room temperature and 20 mL of anhydrous methanol is added followed by 1.0 g of $NaBH_4$ and the resulting solution is stirred at room temperature for 2 hours. The reaction is quenched by the addition of 1 N NaOH and extracted with $CH_2Cl_2$. The $CH_2Cl_2$ extracts are dried over anhydrous $MgSO_4$ and concentrated in vacuo. The residue is chromatographed on $SiO_2$ with ethyl to afford 1-[4-chloro-3-(trifluoromethyl)phenyl]-4-[1-(3,4-dimethoxyphenyl) ethyl]piperazine (compound 2). Analysis $^1H$ NMR (400 MHz, $CDCl_3$): 7.31 (1H, d), 7.19 (1H, m), 6.90 (4H, m), 3.89 (6H, d), 3.38 (1H, m), 3.20 (4H, m), 2.61 (4H, m). MS (LC-MS): Calculated for $C_{21}H_{24}ClF_3N_2O_2$ 428.88, found 429.30 (M+).

III. 3-{1-[4-(4-Bromo-3-methoxy-phenyl)-piperazin-1-yl]-ethyl}-quinoline via Scheme C

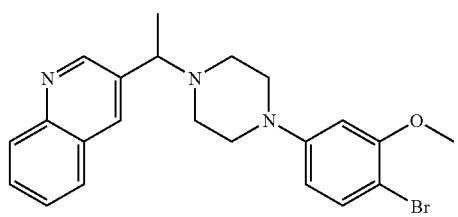

A solution containing 3-quinolinecarboxaldehyde (25 mg, 0.16 mmol, 1.0 equivalents), benzotriazole (19 mg, 0.16 mmol, 1.0 equivalents) and 1-(4-bromo-3-methoxy-phenyl)-piperazine (39 mg, 0.17 mmol, 1.1 equivalents) in ethanol (1 ml) and toluene (2 ml) was heated 20 minutes at 60° C. Solution was concentrated. Residue was coevaporated with toluene, then dissolved in THF and treated with 3.0 M solution of methyl magnesium bromide in diethyl ether (0.13 ml, 0.4 mmol, 2.5 equivalents). The reaction was stirred 18 hours at room temperature. The reaction was diluted with ethyl acetate and washed twice with 1N NaOH, brine, dried (MgSO4), filtered and concentrated. The residue was purified by preparative TLC to afford 3-{1-[4-(4-Bromo-3-methoxy-phenyl)-piperazin-1-yl]-ethyl}-quinoline (compound 3). Yield: 41 mg, 81%. Analysis $H^1$ NMR (400 MHz, CDCl$_3$): 8.96 (1H, s), 8.08 (2H, m), 7.82 (1H, d), 7.70 (1H, t), 7.56 (1H, t), 7.34 (1H, d), 6.45 (1H, m), 6.36 (1H, dd), 3.85 (3H, s), 3.68 (1H, q), 3.18 (4H, m), 2.73 (2H, m), 2.60 (2H, m), 1.54 (3H, d). MS (LC-MS): Calculated for C22H24BrN3O 426.11, found, 426.14 and 428.14, M+2.

IV.   (R)-1-(4-Chloro-3-Methoxy-Phenyl)-4-[1-(3,4-Dimethoxy-Phenyl)-Ethyl]-Piperazine

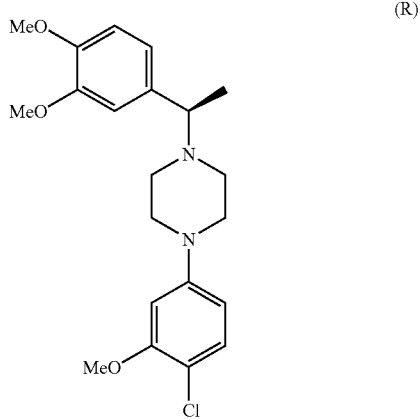

A quantity of 40 g (0.22 moles, 1 eq) of 1-(3,4-dimethoxy-phenyl)-ethanone, 35 g (0.22 moles, 1.0 eq) of piperazine-1 carboxylic acid ethyl ester and 125 mL (0.44 moles, 2.0 eq) of Titanium (IV) isopropoxide were stirred at 70° C. under N$_2$ overnight. The reaction mixture was cooled to 0° C., 200 mL of MeOH was added, and then 9.1 g of NaBH$_4$ was added carefully. Then the reaction mixture was stirred at room temperature overnight. The reaction was quenched with 250 mL of 1N NaOH and extracted with dichloromethane. The extract was washed with brine, dried over Na$_2$SO$_4$ and concentrated to give 70 g of yellowish oil.

The crude oil was dissolved in 250 mL of ethanol and 125 mL of water with 100 g of KOH. The mixture was heated under reflux over night. The solvent was removed and the residue was dissolved in 1 N HCl and washed with ethyl acetate. The aqueous layer was basified with 1 N NaOH and extracted with ethyl acetate. The extract was washed with brine, dried over Na$_2$SO$_4$ and concentrated to yield yellowish oil (38 g, 65%). Analysis: MS (LC-MS): Calculated for C$_{14}$H$_{22}$N$_2$O$_2$ 250.17, found 251.27 (M+).

A quantity of 39 g (0.15 mole, 1 eq) of 1-[1-(3,4-dimethoxy-phenyl)-ethyl]-piperazine was dissolved in 150 mL of tert-butyl methyl ether and 150 mL of methanol, and warmed at 45° C. To this solution, a solution of 11.7 g (0.076 mole, 0.5 eq) of L-tartaric Acid in 50 mL of tert-Butyl methyl ether and 30 mL of methanol that was warmed at 40° C. was added slowly. After cooling down slowly and standing at room temperature overnight, the white precipitate was collected by filtration, giving 26 g solid product. The solid was recrystallized from 300 mL of 90% methanol-water twice to afford 12 g of white solid, which was converted to 7.4 g of free base (38% recovery). Analysis: $^1$H NMR (300 MHz, CDCl$_3$): 6.86 (1H, s), 6.79 (2H, d), 3.85 (6H, d), 3.24 (1H, q), 2.84 (4H, t), 2.35 (4H, m) and 1.32 (3H, d). MS (LC-MS): Calculated for C$_{14}$H$_{22}$N$_{22}$O$_2$ 250.17, found 251.27 (M+). The chiral purity of the product was identified 100% with its Mosher's amide derivative and detected with chiral HPLC.

A quantity of 4.2 g (17 mmoles, 1 eq) of (R)-1-[1-(3,4-dimethoxy-phenyl)-ethyl]-piperazine and 4.4 g (20 mmoles, 1.2 eq) of 5-Bromo-2-chloro-anisole was dissolved in 110 mL of anhydrous toluene, and the solution is purged with N$_2$ for 20 minutes. To the solution was added 0.33 g (0.5 mmoles, 0.03 eq) of rac-2, 2'-Bis(diphenyl-phosphino)-1,1'-binapphtyl, 0.031 g (0.34 mmole, 0.02 eq) of tris(dibenzylideneacetone)-dipalladium(0) and 2.4 g (22 mmoles, 1.3 eq) of potassium tert-butoxide in order. The mixture was heated at 80° C. under N$_2$ overnight. After cooled down, the reaction was filtered through Celite. The organic solution is washed with 1N NaOH and brine, dried over Na$_2$SO$_4$ and concentrated. The residue was purified by flash chromatography on silica gel eluted with 1:1 ethyl acetate: hexanes to afford brownish oil. The product (compound 4) was converted to its HCl salt, giving yellowish solid (4.1 g, 53%). Mp: 172–6° C. Analysis: $^1$H NMR (300 MHz, DMSO): 11.8 (1H, s), 9.2 (1H, s), 7.48 (1H, s), 7.21(1H, d), 7.12 (1H, dd), 6.99 (1H, d), 6.68 (1h, d), 6.59 (1H, dd), 4.42 (1H, t), 3.80 (12H, m), 3.39 (1H, t), 3.19 (1H, t), 2.99 (3H, m), 1.73 (3H, d). MS (LC-MS): Calculated for C$_{21}$H$_{27}$ClN$_2$O$_3$ 390.90, found 391.38 (M+).

V.   (6R,10S)-2-(4-Chloro-3-methoxy-phenyl)-6-(3,4-dimethoxy-phenyl)-octahydro-pyrido[1,2-a]pyrazine via Scheme E

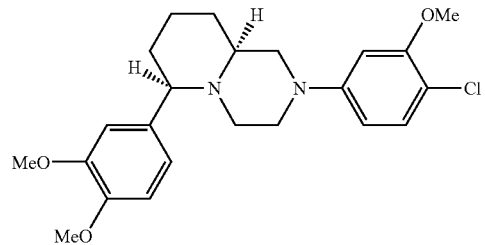

Solid di-t-butyl dicarbonate (16.68 g, 76.43 mmol, 1.10 equivalents) was added in aliquots over 30 minutes to an ice chilled solution of L-2-amino-pent-4-enoic acid (8.0 g, 69.48 g, 1.0 equivalents) in 1N NaOH (140 ml) and dioxane (140 ml). The ice bath was removed and the reaction was stirred at room temperature for 4 hours. The reaction solution was concentrated. The aqueous residue was chilled on ice, layered with EtOAc and acidified with ice cold 1N HCl to pH 2. The aqueous residue was extracted with EtOAc twice. The combined EtOAc extracts were washed with brine, dried with MgSO4, filtered and concentrated to a clear liquid (14.9 g, 100% yield). Analysis $H^1$ NMR (400 MHz, CDCl$_3$): 5.72 (1H, m), 5.18 (2H, m), 5.06 (1H, broad d), 4.38 (1H, m), 2.54 (2H, m), 1.38 (9H, s). LC-MS: base peak 116, M+1 —CO$_2$C(CH3)$_3$.

A solution of L-2-tert-butoxycarbonylamino-pent-4-enoic acid (1.55 g, 7.23 mmol., 1.0 equivalents), 1-(3-dimethylaminopropyl)-3-ethylcarbodiimide hydrochloride (EDCI, 1.525 g, 7.95 mmol, 1.1 equivalents), 4-chloro-3-methoxyaniline (1.135 g, 7.23 mmol, 1.0 equivalents) in pyridine (20 ml) was stirred for 18 hours at room temperature. The reaction was concentrated. The residue was diluted with EtOAc and washed with water. The aqueous was extracted with EtOAc. The combined EtOAc extracts were washed with brine, dried with MgSO4, filtered and concentrated. The residue was triturated with diethyl ether. The beige solid (1.85 g, 5.21 mmol, 72% yield) was collected by filtration. Analysis $H^1$ NMR (400 MHz, $CDCl_3$): 8.5 (1H, broad s), 7.49 (1H, d), 7.22 (1H, m), 6.79 (1H, dd), 5.83 (1H, m), 5.23 (2H, m), 5.00 (1H, broad s), 4.28 (1H, m), 3.89 (3H, s), 2.57 (2H, m), 1.25 (9H, s). MS (LC-MS): Calculated for C17H23ClN2O4 354.1, found 355.25 (M+).

To ice chilled (S)[1-(4-chloro-3-methoxy-phenylcarbamoyl)-but-3-enyl]-carbamic acid tert-butyl ester (7.75 g, 22.40 mmol, 1.0 equivalents) in toluene (112 ml) was added a 0.5M solution of alane-N,N-dimethylethylamine complex in toluene (141 ml, 70.56 mmol, 3.13 mmol). Following addition, the reaction was stirred at room temperature for 18 hours. The reaction was quenched at 0° C. by the addition of 1N NaOH. The mixture was filtered through Celite and extracted 3 times with EtOAc. The EtOAc extracts were washed with brine, dried with MgSO4, filtered, concentrated and coevaporated with toluene. The alane reduction was repeated on the residue by the same procedure using the crude reaction product, toluene (112 ml) and 0.5M solution of alane-N,N-dimethylethylamine complex in toluene (70 ml, 35.o mmol, 1.56 equivalents). Work-up the same way to obtain product as an oil (7.62 g, 22.35 mmol, 100% yield). Analysis $H^1$ NMR (400 MHz, $CDCl_3$): 7.09 (1H, d), 6.21 (1H, broad s), 6.14 (1H, dd), 5.78 (1H, m), 5.18 (2H, m), 4.50 (1H, broad s), 4.23 (1H, broad s), 3.88 (3H, s), 3.18 (2H, m), 2.32 (2H, m), 1.39 (9H, s). MS (LC-MS): Calculated for C17H25ClN2O3 340.16, found 341.25 (M+).

To an ice chilled biphasic solution containing (S){1-[(4-chloro-3-methoxy-phenylamino)-methyl]-but-3-enyl}-carbamic acid tert-butyl ester (7.00 g, 20.53 mmol, 1.0 equivalents) in EtOAc (95 ml) and saturated sodium bicarbonate (122 ml) was added a solution of chloroacetylchloride (1.96 ml, 24.64 mmol, 1.2 equivalents). Following the addition, the reaction was stirred for 30 minutes at room temperature. The layers were separated. The aqueous was extracted with EtOAc. The combined EtOAc extracts were washed with brine, dried with MgSO4, filtered and concentrated to give an oil (7.58 g, 18.22 mmol, 89% yield). Analysis $H^1$ NMR (400 MHz, $CDCl_3$): 7.42 (1H, d), 7.02 (1H, broad s), 6.82 (1H, m), 5.70 (1H, m), 5.09 (2H, m), 4.80 (1H, d), 4.30 (1H, m), 3.94 (4H, m), 3.80 (2H, s), 3.11 (1H, m), 2.20 (2H, m), 1.42 (9H, s). MS (LC-MS): Calculated for C19H26Cl2N2O4 416.13, found 417.19 (M+).

To an ice chilled solution containing (S)1-{[(2-chloro-acetyl)-(4-chloro-3-methoxy-phenyl)-amino]-methyl}-but-3-enyl)-carbamic acid tert-butyl ester (7.58 g, 18.22 mmol, 1.0 equivalents) was added trifluoroacetic acid dropwise. The reaction was stirred on ice for 30 minutes. The reaction was concentrated. The residue was dissolved in DMF (455 ml) and triethylamine (12.75 ml, 90.91 mmol, 5.0 equivalents) and stirred at 50° C. for 5 hours. The reaction was concentrated. The residue was subjected to acid base extraction to remove neutral byproducts. The residue was partitioned between 1N HCl and EtOAc. The aqueous was extracted with EtOAc. The EtOAc extracts were discarded. The aqueous was basified and extracted with dichloromethane. The dichloromethane extracts were dried with MgSO4, filtered and concentrated to an oil (4.0 g, 14.28 mmol, 78% yield). Analysis $H^1$ NMR (400 MHz, $CDCl_3$): 7.36 (1H, d), 6.85 (1H, m), 6.77 (1H, dd), 5.78 (1H, m), 5.19 (2H, m), 3.90 (3H, s), 3.73 (2H, dd), 3.50 (2H, m), 3.22 (1H, m), 2.29 (2H, m). MS (LC-MS): Calculated for C14H17ClN2O2 280.10, found 281.15 (M+).

To an ice chilled solution containing (S)5-allyl-1-(4-chloro-3-methoxy-phenyl)-piperazin-2-one (4.00 g, 14.28 mmol, 1.0 equivalents) in toluene (50 ml) was added dropwise a 0.5M solution of alane-N,N-dimethylethylamine complex in toluene (86 ml, 42.86 mmol, 3.0 equivalents). Following addition, the reaction was stirred at room temperature over night for 18 hours. The reaction was quenched at 0° C. with 1N NaOH, extracted with EtOAc twice and dichloromethane twice. Organic extracts were dried with MgSO4, filtered and concentrated to an oil (3.80 g, 14.28 mmol, 100% yield). Analysis $H^1$ NMR (400 MHz, $CDCl_3$): 7.20 (1H, d), 6.48 (1H, m), 6.43 (1H, dd), 5.82 (1H, m), 5.14 (2H, m), 3.88 (3H, s), 3.47 (2H, d), 3.12 (1H, m), 2.96 (1H, dt), 2.90 (1H, m), 2.89 (1H, dt), 2.45 (1H, t), 2.26 (1H, m), 2.22 (1H, m). MS (LC-MS): Calculated for C14H19ClN2O266.12, found 267.19 (M+).

A solution containing (S)3-allyl-1-(4-chloro-3-methoxy-phenyl)-piperazine (3.81 g, 14.28 mmol, 1.0 equivalents) and di-t-butyldicarbonate (3.428 g, 15.71 mmol, 1.1 equivalents) in THF (71 ml) was stirred at room temperature for 18 hours. The solution was concentrated to an oil (5.23 g, 14.28 mmol, 100% yield.) Analysis $H^1$ NMR (400 MHz, $CDCl_3$): 7.19 (1H, d), 6.45 (1H, m), 6.38 (1H, dd), 5.82 (1H, m), 5.11 (2H, m), 4.23 (1H, broad s), 4.00 (1H, m), 3.87 (3H, s), 3.42 (2H, m), 3.19 (1H, m), 2.84 (1H, dd), 2.74 (1H, dt), 2.50 (2H, m), 1.48 (9H, s). MS (LC-MS): Calculated for C19H27ClN2O3 366.17, found 367.18 (M+).

To a solution of (S)2-allyl-4-(4-chloro-3-methoxy-phenyl)-piperazine-1-carboxylic acid tert-butyl ester (5.23 g, 14.28 mmol, 1.0 equivalents) in DMF (39 ml) and water (5.5 ml) were added palladium (II) chloride (2.616 g, 14.75 mmol, 1.03 equivalents), copper (I) chloride (1.460 g, 14.75 mmol, 1.03 equivalents). Oxygen gas was bubbled into the solution. The reaction was stirred under oxygen balloon for 18 hours at room temperature. The mixture was filtered through Celite. The filtrated was partitioned between EtOAc and water. The aqueous was extracted with EtOAc. The combined EtOAc extracts were washed with brine, dried with MgSO4, filtered and concentrated. The residue was purified by flash chromatography on silica gel eluted with 50% EtOAc: Hexanes. The product was a yellow oil (3.45 g, 9.07 mmol, 63% yield). Analysis $H^1$ NMR (400 MHz, $CDCl_3$): 7.19 (1H, d), 6.44 (1H, m), 6.36 (1H, dd), 4.61 (1H, broad s), 3.99 (1H, m), 3.87 (3H, s), 3.48 (2H, m), 3.16 (2H, m), 2.93 (1H, dd), 2.88 (1H, dt), 2.68 (1H, m), 2.19 (3H, s), 1.60 (9H, s). MS (LC-MS): Calculated for C19H27ClN2O4 382.17, found 383.17 (M+). The chiral purity was assessed by chiral HPLC. A racemic standard showed a 1:1 mixture of 2 peaks with retention times 10.64 and 12.13 minutes. Analysis of the ketone synthesized from L-allylglycine showed only 1 peak at 10.64 minutes and none of the enantiomer.

To an ice chilled solution of (S)4-(4-chloro-3-methoxy-phenyl)-2-(2-oxo-propyl)-piperazine-1-carboxylic acid tert-butyl ester (363 mg g, 0.955 mmol, 1.0 equivalents) in dichloromethane (4 ml) was added trifluoroacetic acid (4 ml). The reaction was stirred on ice for 30 minutes and then concentrated. The residue was dissolved in methanol (8 ml) and chilled on ice. To this solution was added 3,4-dimethoxybenzaldehyde (206 mg, 1.24 mmol, 1.3 equivalents) and 6N NaOH (0.96 ml, 5.73 mmol, 6.0 equivalents). The reaction was stirred at 55° C. over night. The reaction was concentrated. The residue was partitioned between 1N NaOH and dichloromethane. The aqueous was extracted with dichloromethane. The organic extracts were dried with MgSO4, filtered and concentrated. The residue was purified by flash chromatography on silica gel eluted with 2.5% methanol/dichloromethane. The product was obtained as a white foam (115 mg, 0.27 mmol, 29% yield). Analysis $H^1$ NMR (400 MHz, CDCl₃): 7.19 (1H, d), 6.86 (3H, m), 6.46 (1H, m), 6.41 (1H, dd), 3.91 (3H, s), 3.89 (3H, s), 3.87 (3H, s), 3.44 (2H, m), 3.30 (2H, dd), 2.78 (4H, m), 2.50 (3H, m), 2.08 (1H, td). MS (LC-MS): Calculated for C23H27ClN2O4 430.17, found 431.15, (M+). Additional fragmentation products resulting from decomposition in mobile phase were observed.

To a solution of (6R,10S)2-(4-chloro-3-methoxy-phenyl)-6-(3,4-dimethoxy-phenyl)-octahydro-pyrido[1,2-a]pyrazin-8-one (38 mg, 0.09 mmol, 1.0 equivalents) was added p-toluene sulfonylhydrazide (21 mg, 1.3 equivalents). The reaction was stirred at room temperature for 18 hours. Sodium borohydride (34 mg, 0.89 mmol, 10.0 equivalents) was added. The reaction was stirred under reflux at 65° C. for 4 hours. The reaction was quenched with 10% ammonium chloride and partitioned between 1N NaOH and dichloromethane. The organic extract was washed with brine, dried with MgSO4, filtered and concentrated. The residue was purified on a 500 micron preparative TLC plate eluted with 1:1 ethyl acetate: hexane. (6R,10S)2-(4-Chloro-3-methoxy-phenyl)-6-(3,4-dimethoxy-phenyl)-octahydro-pyrido[1,2-a]pyrazine (compound 5) was obtained as an oil (25 mg, 0.06 mmol, 67% yield). Analysis H¹ NMR (400 MHz, CDCl₃): 7.19 (1H, d), 6.90 (2H, m), 6.45 (1H, m), 6.41 (1Hm dd), 3.91 (3H, s), 3.89 (3H, s), 3.87 (3H, s), 3.41 (2H, m), 2.97 (1H, dd), 2.75 (1H, m), 2.62 (1H, m), 2.37 (1H, m), 2.03 (1H, dt), 1.42–1.80 (6H, m). MS (LC-MS): Calculated for C23H29ClN2O3 416.19, 417.19 (M+).

VI. (6R,10S)[6-(3,4-Dimethoxy-phenyl)-octahydro-pyrido[1,2-a]pyrazin-2-yl]-(4-trifluoromethyl-phenyl)-methanone (via Scheme F)

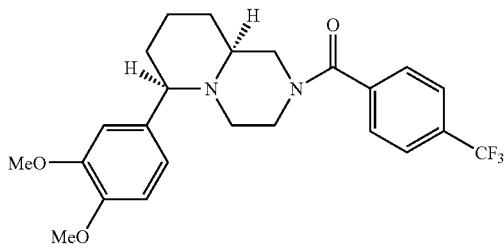

(S)2-(4-Benzyl-piperazin-2-yl)-ethanol (2.2 g, 10 mmol) was dissolved in anhydrous dichloromethane (100 mL) at room temperature. Di-tert-butyl dicarbonate (BOC anhydride) was added (2.20 g, 11 mmol) and the resulting solution was stirred at room temperature overnight. The reaction was quenched by diluting with brine. The organic phase was separated and the aqueous phase was washed with dichloromethane. The organic phases were combined and washed with brine (2×50 mL), dried (MgSO₄), and filtered. Solvent removal under reduced pressure afforded 4-benzyl-2-(2-hydroxy-ethyl)-piperazine-1-carboxylic acid tert-butyl ester as a clear oil (3.13 g, 98% yield). MS: 320 (M+). H-1 NMR (400 MHz, CDCl₃): 7.3 (5H, br), 4.28 (1H, br), 4.0 (1H, br), 3.8 (1H, br), 3.6 (1H, br), 3.5 (2H, br), 3.4 (1H, m), 3.0 (1H, t), 2.6–2.8 (2H, br), 2.22 (1H, dd, J=4; 11.4 Hz) 2.02 (1H, dt, J=3.5; 11.7 Hz), 1.46 (s,9H).

Under nitrogen atmosphere (balloon), (S)4-benzyl-2-(2-hydroxy-ethyl)-piperazine-1-carboxylic acid tert-butyl ester (3.1 g, 97 mmol) was dissolved in anhydrous dichloromethane (100 mL) containing previously activated 4 Å molecular sieves (1.0 g) and 4-methylmorpholine N-oxide (13 mmol, 1.5 g). The reaction started by addition of tetrapropylammonium perruthenate (150 mg, 0.15 mmol). After 1 hour, LC/MS analysis showed no remaining starting material. The black suspension was filtered through a silicagel plug and the desired product was eluted with 5% methanol in chloroform. Solvent evaporation under reduced pressure provided 4-benzyl-2-(2-oxo-ethyl)-piperazine-1-carboxylic acid tert-butyl ester as a clear oil (2.9 g, 94% yield). MS: 318 (M+). H-1 NMR significant signals (400 MHz, CDCl₃): 9.78 (1H, t, J=2.4 Hz), 7.25 (5H, s), 3.68 (2H, t, 3 Hz), 3.48 (1H, d, J=13.2), 3.36 (1H, d, J=13.2 Hz), 2.2 (1H, dd, J=4; 11 Hz), 2.08 (1H, dt, J=3.5, 11.7 Hz), 1.44 (9H, s).

(S)4-benzyl-2-(2-oxo-ethyl)-piperazine-1-carboxylic acid tert-butyl ester (2.9 g, 9.1 mmol) was dissolved in anhydrous tetrahydrofuran (100 mL) at 0° C. under an atmosphere of nitrogen (balloon). Methyl magnesium bromide (12 mmol, 3.0 M solution in THF, 4.0 mL) was added dropwise and the reaction was taken to room temperature. After 3 hours, the reaction was taken to 0° C. and quenched by dropwise addition of saturated aqueous ammonium chloride solution. The phases were separated, and the organic layer was washed with brine (2×100 mL), dried (MgSO₄) and filtered. Solvent evaporation under reduced pressure produced the crude 4-benzyl-2-(2-hydroxy-propyl)-piperazine-1-carboxylic acid tert-butyl ester as a mixture of diastereoisomers (2.8 g, 85% yield). MS: 334 (M). H-1 NMR significant signals (400 MHz, CDCl₃): 7.27 (5H, s), 1.44 (9H, s), 1.17 and 1.18 (d, 3H combined).

Under nitrogen atmosphere (balloon), (S)4-benzyl-2-(2-hydroxy-propyl)-piperazine-1-carboxylic acid tert-butyl ester (2.8 g, 97 mmol) was dissolved in anhydrous dichloromethane (90 mL) containing previously activated 4 Å molecular sieves (1.0 g) and 4-methylmorpholine N-oxide (13 mmol, 1.5 g). The reaction started by addition of tetrapropylammonium perruthenate (200 mg, 0.2 mmol). After 1 hour LC/MS analysis showed no remaining starting material. The black suspension was filtered through a silicagel plug. Solvent evaporation under reduced pressure provided the crude product as a brown oil (2.7 g). Purification was carried out by flash chromatography, which yielded 1.4 g (43% yield) of 4-benzyl-2-(2-oxo-propyl)-piperazine-1-carboxylic acid tert-butyl ester as an oil. MS: 318 (M+). H-1 NMR significant signals (400 MHz, CDCl₃): 7.25 (5H, s), 3.38 (1H, d, J=13.2), 3.36 (1H, d, J=13.2 Hz), 2.1 (3H, s), 1.42 (9H, s). C-13 NMR significant signals (100 MHz, CDCl₃): 206.8 ppm.

To an ice chilled solution containing (S)4-benzyl-2-(2-oxo-propyl)-piperazine-1-carboxylic acid tert-butyl ester (199 mg, 0.60 mmol, 1.0 equivalents) in dichloromethane (4 ml) was added trifluoroacetic acid (4 ml). The reaction was stirred at 0° C. for 30 minutes, concentrated and coevaporated with toluene. The residue was dissolved in methanol (5 ml). To this solution at room temperature was added 3,4-dimethoxybenzaldehyde (130 mg, 0.78 mmol, 1.3 equivalents) and 6N NaOH (0.6 ml, 3.6 mmol, 6.0 equivalents). The reaction was heated at 55° C. for 15 hours. The reaction partitioned between dichloromethane and 1N NaOH. The aqueous phase was extracted with dichloromethane. The dichloromethane extracts were washed with brine, dried with MgSO₄, filtered and concentrated. The residue was purified on two 1000 micron preparative TLC plates eluted with 4% MeOH/dichloromethane. Obtained 44 mg of the cis stereoisomer (0.12 mmol, 19% yield) and 16 mg of the trans stereoisomer (0.04 mmol, 7% yield.) Analysis H¹ NMR (400 MHz, CDCl₃)of cis product: 7.29 (5H, m), 6.86 (3H, m), 3.89 (3H, s), 3.87 (3H, 3H), 3.50 (2H, m). 3.25 (1H, dd), 2.67 (4H, m), 2.44 (2H, m), 2.28 (m, 1H), 2.08 (3H, m). MS (LC-MS): Calculated for C23H28N2O3 380.21, found 381.20 (M+).

A solution of 2-benzyl-6-(3,4-dimethoxy-phenyl)-octahydro-pyrido[1,2-a]pyrazin-8-one (43 mg, 0.11 mmol, 1.0 equivalents) and p-toluenesulfonylhydrazide (27 mg, 0.15 mmol, 1.3 equivalents) in methanol (1.0 ml) was stirred at room temperature for 15 hours. Sodium borohydride (43 mg, 1.1 mmol, 10.0 equivalents) was heated under reflux at 65° C. Since TLC indicated reaction was not complete after 5 hours, additional sodium borohydride (52 mg, 1.37 mmol, 12 equivalents) was added and the reaction was stirred at 65° C. for 18 hours. The reaction was partitioned between 1N NaOH and dichloromethane. The aqueous was extracted with dichloromethane. The dichloromethane was washed with brine, dried with MgSO4, filtered and concentrated. The residue was purified on a 500 micron preparative TLC eluted with (4% MeOH/dichloromethane), and 14 mg (6R, 10S)2-benzyl-6-(3,4-dimethoxy-phenyl)-octahydro-pyrido[1,2-a]pyrazine was obtained (0.04 mmol, 38% yield). Analysis H$^1$ NMR (400 MHz, CDCl$_3$): 7.29 (5H, m), 6.80 (3H, m), 3.88 (3H, s), 3.86 (3H, s), 3.48 (2H, m), 2.89 (1H, broad d), 2.65 (2H, m), 2.54 (1H, broad d), 2.22 (1H, m), 2.05 (1H, m), 1.96 (2H, m), 1.54 (6H, m). MS (LC-MS): Calculated for C23H30N2O2 366.23, found 367.26 (M+).

A solution of (6R,10S)2-benzyl-6-(3,4-dimethoxy-phenyl)-octahydro-pyrido[1,2-a]pyrazine (14 mg, 0.04 mmol), 10% Pd/C (3 mg), and ammonium formate (12 mg, 0.19 mmol) was heated under reflux for 6 hours. Additional ammonium formate (11 mg, 0.17 mmol) and the reaction was stirred under reflux for 15 hours. The reaction was filtered through Celite. The filtrate was concentrated. The residue was dissolved in dichloromethane (0.5 ml) and treated with triethylamine (42 microliters, 0.19 mmol, 5.0 equivalents) and trifluoromethylbenzoylchloride (4 microliters, 0.03 mmol, 1.5 equivalents). The reaction was stirred for 1 hour at room temperature. The reaction was transferred to a vial and shaken with ethyl acetate and 1N NaOH. The aqueous was extracted again with ethyl acetate. The ethyl acetate extracts were concentrated. The residue was purified 250 micron analytical TLC, yielding 3 mg of (6R,10S)[6-(3,4-Dimethoxy-phenyl)-octahydro-pyrido[1,2-a]pyrazin-2-yl]-(4-trifluoro-methyl-phenyl)-methanone (compound 6; 0.007 mmol, 18% yield). MS (LC-MS): Calculated for C24H27F3N2O3 448.20, found 449.15 (M+). Chiral HPLC showed product was 97% one enantiomer, 3% opposite enantiomer.

VII. (6R,10S)2-(4-Chloro-3-methoxy-phenyl)-6-(3,4-dimethoxy-phenyl)-octahydro-pyrido[1,2-a]pyrazin-8-ol

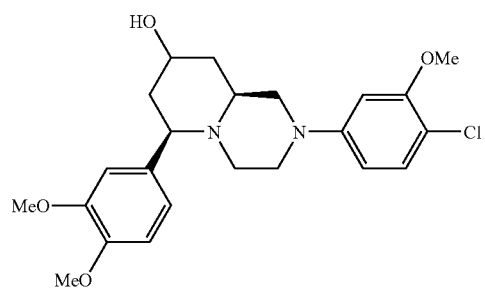

(6R,10S)2-(4-Chloro-3-methoxy-phenyl)-6-(3,4-dimethoxy-phenyl)-octahydro-pyrido[1,2-a]pyrazin-8-one (20 mg, 0.05 mmol, 1.0 equivalent) and sodium borohydride (9 mg, 0.24 mmol, 5.1 equivalents) in methanol (2 ml) were stirred at room temperature for 90 minutes. Reaction was quenched with 1N NaOH and extracted with dichloromethane twice. The dichloromethane extracts were washed with brine, dried (MgSO$_4$), filtered and concentrated to 15 mg film. Yield of 2-(4-Chloro-3-methoxy-phenyl)-6-(3,4-dimethoxy-phenyl)-octahydro-pyrid[1,2-a]pyrazin-8-ol (compound 7): 75%. Analysis H$^1$ NMR (400 MHz, CDCl$_3$): 7.19 (1H, d), 6.87 (3H, m), 6.44 (2H, m), 3.89 (3H, s), 3.85 (s, 3H), 3.81 (3H, s), 3.35 (2H, m), 2.90 (1H, dd), 2.71 (3H, m), 2.38 (1H, t), 2.04 (3H, m), 1.58 (m, 3H). MS (LC-MS): Calculated for C23H29ClN2O4 433.18, 433.4.

VIII. 8-(4-Chloro-3-methoxy-phenyl)-4-(3,4-dimethoxy-phenyl)-octahydro-pyrazino[2,1-c][1,4]thiazine via Scheme G

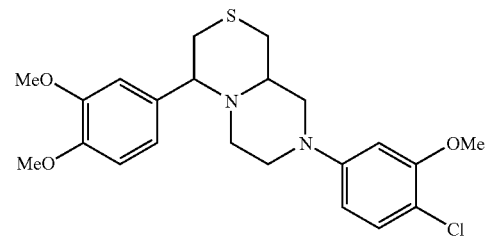

To an ice chilled solution of potassium hydroxide (655 mg, 11.68 mmol, 1.0 equivalents) in methanol (32 ml) was added L-2-tert-butoxycarbonylamino-3-mercapto-propionic acid methyl ester (2.64 ml, 12.85 mmol, 1.1 equivalents). The reaction was stirred on ice for 10 minutes. To the reaction solution was added a solution of 2-chloro-1-(3,4-dimethoxy-phenyl)-ethanone (2500 mg, 11.68 mmol, 1.0 equivalents) followed by additional THF (7 ml). The reaction was stirred on ice for 4 hours. Solution was concentrated. The residue was extracted with dichloromethane. The dichloromethane extracts were dried with MgSO$_4$, filtered and concentrated. The residue was purified by flash chromatography on silica gel eluted with 25% ethyl acetate: hexane. 2-tert-Butoxycarbonylamino-3-[2-(3,4-dimethoxy-phenyl)-2-oxo-ethylsulfanyl]-propionic acid methyl ester was obtained as an oil (4.72 g, 98% yield). Analysis H$^1$ NMR (400 MHz, CDCl$_3$): 7.55 (2H, m), 6.88 (1H, d), 5.43 (1H, broad d), 4.57 (1H, m), 3.95 (3H, s), 3.93 (3H, s), 3.85 (2H, s), 3.73 (3H, s), 3.00 (2H, dq), 1.41 (9H, s). MS (LC-MS): Calculated for C19H27NO7S 414.15, found 414.21.

To an ice chilled solution of 2-tert-butoxycarbonylamino-3-[2-(3,4-dimethoxy-phenyl)-2-oxo-ethylsulfanyl]-propionic acid methyl ester (2.00 g, 9.34 mmol, 1.0 equivalents) in dichloromethane (9 ml) was added trifluoroacetic acid (9 ml). The reaction solution was stirred on ice for 4 hours. The solution was concentrated, coevaporated with toluene. The residue was dissolved in dichloromethane (30 ml) and chilled on ice. To this was added sodium triacetoxyborohydride (2.97 g, 14.02 mmol, 1.5 equivalents) followed by dichloromethane (7 ml). The reaction was stirred 18 hours at room temperature. Saturated sodium bicarbonate was added, and the reaction mixture was extracted with dichloromethane. The dichloromethane extracts were dried with MgSO$_4$, filtered and concentrated. 5-(3,4-Dimethoxy-phenyl)-thiomorpholine-3-carboxylic acid methyl ester was obtained as an oil (1.63 g, 59% yield). Analysis H¹ NMR (400 MHz, CDCl₃): 6.92 (2H, m), 6.83 (1H, d), 3.95 (3H, s), 3.93 (3H, s), 3.87 (2H, m), 3.85 (3H, s), 2.77 (3H, m), 2.42 (1H, m). MS (LC-MC): Calculated for C14H19NO4S 297.10, found 298.17.

A 2.0M solution of trimethylaluminum (0.39 ml, 0.78 mmol, 3.5 equivalents) was added to a solution of 5-(3,4-dimethoxy-phenyl)-thiomorpholine-3-carboxylic acid methyl ester (67 mg, 0.22 mmol, 1.0 equivalents) and 4-chloro-3-methoxyaniline (106 mg, 0.68 mmol, 3.0 equivalents). The solution was stirred at 50° C. for 18 hours. The reaction was quenched with 1N NaOH and extracted with dichloromethane. The dichloromethane extracts were dried with MgSO₄, filtered and concentrated. The residue was purified on a 1000 micron preparative TLC. 5-(3,4-Dimethoxy-phenyl)-thiomorpholine-3-carboxylic acid (4-chloro-3-methoxy-phenyl)-amide was obtained as a peach solid (71 mg, 76% yield). Analysis H¹ NMR (400 MHz, CDCl₃): 8.61 (1H, s), 7.58 (1H, m), 7.26 (1H, m), 6.90 (2H, m), 6.78 (1H, d), 4.04 (1H, m), 3.91 (10H, m), 2.98 (1H, m), 2.78 (2H, m), 2.59 (1H, m). MS (LC-MS): Calculated for C20H23ClN2O4S 423.11, found 423.22.

To an ice chilled suspension containing 5-(3,4-dimethoxy-phenyl)-thiomorpholine-3-carboxylic acid (4-chloro-3-methoxy-phenyl)-amide n(71 mg, 0.17 mmol, 1.0 equivalents) in toluene (1.5 ml) was added a 0.5M solution of alane (1.6 ml, 0.8 mmol, 4.8 equivalents). The reaction was stirred at room temperature for 2 hours. The reaction was quenched with 1N NaOH and extracted 3 times with dichloromethane. The dichloromethane extracts were dried with MgSO4, filtered and concentrated to yield (4-chloro-3-methoxy-phenyl)-[5-(3,4-dimethoxy-phenyl)-thiomorpholine-3-ylmethyl]-amine as an oil (65 mg, 95% yield). H¹ NMR (400 MHz, CDCl₃): 7.11 (1H, d), 6.93 (2H, m), 6.80 (1H, m), 6.19 (m, 2H), 3.86 (10H, m), 3.19 (3H, m), 2.80 (2H, m), 2.50 (2H, m). (LC-MS): Calculated for C20H25ClN2O3S 409.13, found 409.23.

A solution of (4-chloro-3-methoxy-phenyl)-[5-(3,4-dimethoxy-phenyl)-thiomorpholin-3-ylmethyl]-amine (100 mg, 0.245 mmol, 1.0 equivalents), dibromoethane (0.31 ml, 3.55 mmol, 14.5 equivalents) and triethylamine (0.15 ml, 1.09 mmol, 4.5 equivalents) in dimethylacetamide (2 ml) was heated at 90° C. for 4 hours. Additional dibromoethane (0.16 ml, 1.84 mmol, 7.5 equivalents) and triethylamine (0.25 ml, 1.76 mmol, 7.2 equivalents) was added and reaction was stirred for 4 hours at 90° C. Additional dibromoethane (0.14 ml, 1.62 mmol, 6.6 equivalents) and triethylamine (0.10 ml, 0.71 mmol, 2.9 equivalents) were added and reaction was stirred 18 hours at 90° C. Reaction was cooled and filtered to remove triethylammonium hydrobromide. Filtrate was concentrated. Residue was purified on a 1000 micron preparative TLC. 34 mg of 8-(4-chloro-3-methoxy-phenyl)-4-(3,4-dimethoxy-phenyl)-octahydro-pyrazino[2,1-c][1,4]thiazine (Compound 8) was obtained, along with 36 mg recovered starting material. Yield of product: 32%. H¹ NMR (400 MHz, CDCl₃): 7.19 (1H, d), 6.86 (3H, m), 6.42 (2H, m), 3.89 (3H, s), 3.88 (3H, s), 3.86 (3H, s), 3.50 (1H, m), 3.19 (2H, dd), 2.92 (1H, m), 2.75 (5H, m), 2.48 (2H, t), 2.15 (1H, dt). MS LC-MS): Calculated for C22H27ClN2O3S 435.14, 435.24.

IX. 2-(4-Chloro-3-methoxy-phenyl)-6-(3,4-dimethoxy-phenyl)-octahydro-pyrido[1,2-a]pyrazine Via Scheme H

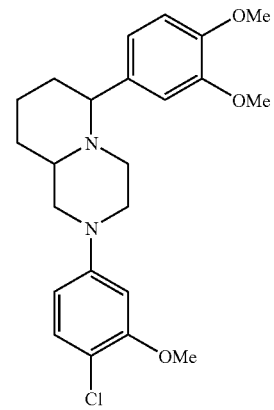

To a suspension of 2.2 g (0.011 moles, 1 eq) of 5-bromopiconilic acid in 5 mL of DCM, is added 4.0 mL of thionyl chloride. The mixture is refluxed for 2.5 hours, and then is concentrated and further co-evaporated with toluene. The residue is dissolved in 10 mL of DCM.

A quantity of 2.8 g (0.022 moles, 2.0 eq) of K₂CO₃ and 1 mL (0.01 moles, 1.5 eq) of hydroxyl ethylamine are dissolved in 23 mL of water and cooled in ice bath. The DCM solution prepared above is added slowly, and the reaction is warmed to room temperature and stirred for 2 hours. The reaction is diluted with DCM and separated. The organic layer is washed with brine, dried over Na₂SO₄ and concentrated to give 6-bromo-pyridine-2-carboxylic acid (2-hydroxy-ethyl)-amide as a yellow oil (2.3 g, 86%). Analysis: MS (LC-MS): Calculated for C₈H₉BrN₂O₂ 245.07, found 245.20 (M+) & 247.20 (m+2).

A quantity of 0.25 g (1.0 mmoles, 1 eq) of 6-bromo-pyridine-2-carboxylic acid (2-hydroxy-ethyl)-amide and 0.28 g (1.5 mmoles, 1.5 eq) of 3,4-dimethoxyphenyl boronic acid are added in 20 mL of ethylene glycol dimethyl ether with 2 ml of ethanol and 2 ml of 2 M Na₂CO₃. The mixture is purged with N₂ for 20 minutes, and then 57 mg (0.05 mmoles, 0.05 eq) of Tris (dibenzylideneacetone)-dipalladium (0) is added. The reaction is heated at 80° C. for 6 hours. At that time there is no starting material shown on TLC. The reaction is filtered through Celite and the solvent is removed. The residue is taken in ethyl acetate, washed with brine, dried over Na₂SO₄ and concentrated to afford 6-(3,4-dimethoxy-phenyl)-pyridine-2-carboxylic acid (2-hydroxy-ethyl)-amide as a yellowish oil (0.21 g, 69%), which is used in the next step without purification. Analysis: MS (LC-MS): Calculated for C₁₆H₁₈N₂O₄ 302.33, found 303.39 (M+1).

A quantity of 3.0 g (10 mmoles, 1 eq) of 6-(3,4-dimethoxy-phenyl)-pyridine-2-carboxylic acid (2-hydroxy-ethyl)-amide and 0.23 g (1.0 mmoles, 0.1 eq) of platinum dioxide are added into 35 mL of ethanol and 2.0 ml concentrated HCl. The suspension is hydrogenated under 50 psi of H₂ at room temperature overnight. After TLC shows no starting material existing, the reaction is filtered through Celite and solvent is removed. The residue is taken in ethyl acetate, washed with saturated Na₂CO₃ and brine, dried over Na₂SO₄ and concentrated to give 6-(3,4-dimethoxy-phenyl)-piperidine-2-carboxylic acid (2-hydroxy-ethyl)-amide as a yellowish oil. The oil is triturated with ethyl acetate and hexanes to afford a white solid (1.6 g, 52%). Analysis: NMR (300 MHz, CDCl₃): 7.18 (1H, t), 6.90 (2H, m), 6.82 (1H, m), 3.87 (6H, d), 3.66 (3H, m), 3.39 (3H, m), 2.00 (2H, m), 1.80 (1H, m) and 1.22 (2H, m). MS (LC-MS): Calculated for C$_{16}$H$_{24}$N$_2$O$_4$ 308.37, found 309.34 (M+1).

A solution of 1.5 g (5.0 mmoles, 1 eq) of 6-(3,4-Dimethoxy-phenyl)-piperidine-2-carboxylic acid (2-hydroxy-ethyl)-amide in 18 mL of THF is added slowly into 15 mL of 1 M LiAlH$_4$ solution in THF. The reaction is heated at 60° C. under N$_2$ for 6 hours. At that time there is no starting material shown on TLC. Cooled in ice bath, to the reaction are added 0.5 ml water, 0.5 mL 15% NaOH and 1.5 mL water slowly in order. Finally, some anhydrous MgSO$_4$ is added, and the reaction mixture is filtered through Celite. Upon the removal of the solvent, the residue is taken in ethyl acetate, washed with brine, dried over Na$_2$SO$_4$ and concentrated to afford 2-{[6-(3,4-dimethoxy-phenyl)-piperidin-2-ylmethyl]-amino}-ethanol as an oil (1.5 g, 68%), which is used in the next step without purification. Analysis: MS (LC-MS): Calculated for C$_{16}$H$_{26}$N$_2$O$_3$ 294.39, found 295.37 (M+1).

To the solution of 3.4 g (11.6 mmoles, 1 eq) of 2-{[6-(3,4-dimethoxy-phenyl)-piperidin-2-ylmethyl]-amino}-ethanol and 0.20 g (17.5 mmoles, 1.5 eq) of triphenyl phosphine in 120 mL of THF, is added 1.9 mL (12.7 mmoles, 1.1 eq) of diethyl azodicarboxylate, and the reaction is stirred at room temperature overnight. At that time there is no starting material shown on TLC. After removal of the solvent, the residue is taken in ethyl acetate and extracted with 1 N HCl solution. The acidic aqueous is basified with 1N NaOH to pH 10, and extracted with dichloromethane 3 times. The organic extracts are washed with brine, dried over Na$_2$SO$_4$ and concentrated to give oil product, which is purified by flash chromatography on silica gel eluted with 50:10:1 DCM: MeOH: NH$_4$OH, to afford 6-(3,4-dimethoxy-phenyl)-octahydropyrido[1,2-a]pyrazine as a brownish stick solid (0.85 g, 27%). Analysis: $^1$H NMR (300 MHz, CDCl₃): 6.80 (3H, m), 3.87 (3H, s), 3.84 (3H, s), 3.29 (1H, s), 2.92~2.68 (4H, m), 2.60 (2H, m), 2.13 (1H, m), 1.82~1.05 (8H, m). MS (LC-MS): Calculated for C$_{16}$H$_{18}$N$_2$O$_4$ 302.33, found 303.39 (M+1).

A quantity of 0.85 g (3.0 mmoles, 1 eq) of 6-(3,4-dimethoxy-phenyl)-octahydropyrido[1,2-a]pyrazine and 0.76 g (3.4 mmoles, 1.1 eq) of 5-bromo-2-chloro-anisole is dissolved in 25 mL of anhydrous toluene, and the solution is purged with N$_2$ for 20 min. To the solution is added 0.18 g (0.30 mmoles, 0.10 eq) of rac-2, 2'-Bis(diphenyl-phosphino)-1,1'-binapphtyl, 0.14 g (0.15 mmole, 0.05 eq) of Tris(dibenzylideneacetone)-dipalladium(0) and 0.52 g (4.6 mmoles, 1.5 eq) of Potassium tert-butoxide in order. The mixture is heated at 80° C. under N$_2$ overnight. After it is cooled down, the reaction is filtered through Celite. The organic solution is washed with 1N NaOH and brine, dried over Na$_2$SO$_4$ and concentrated. The residue is purified by flash chromatography on silica gel eluted with 50:1 dichloromethane: methanol to afford 2-(4-chloro-3-methoxy-phenyl)-6-(3,4-dimethoxy-phenyl)-octahydro-pyrido[1,2-a] pyrazine (compound 5) as a brownish stick solid (0.85 g, 68%). Analysis: $^1$H NMR (300 MHz, CDCl₃): 7.16 (1H, d), 6.80 (3H, m), 6.40 (2H, m). 3.88 (3H, s), 3.86 (3H, s), 3.85 (3H, s), 3.40 (2H, m), 2.95 (1H, m), 2.70 (3H, m), 2.30 (1H, m), 2.00 (1H, m), 1.82~1.40 (6H, m). MS (LC-MS): Calculated for C$_{23}$H$_{29}$ClN$_2$O$_3$ 416.94, found 417.23 (M+1).

X. (6R,9S) 2-(4-chloro-3-methoxy-phenyl)-6-(3,4-dimethoxy-phenyl)-octahydro-pyrrolo[1,2-a]pyrazine via Scheme J

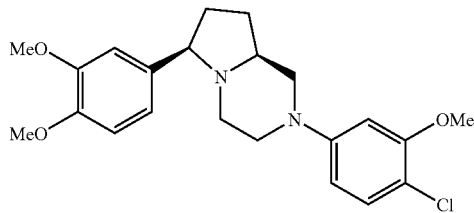

A suspension containing (2S)5-oxo-pyrrolidine-1,2-dicarboxylic acid 1-tert-butyl ester (10.00 g, 0.044 mol, 1.0 equivalent), benzyl bromide (7.88 g, 0.046 mol, 1.05 equivalents), and potassium carbonate (15.20 g, 0.11 mol, 2.5 equivalents) in DMF (200 ml) was allowed to stir at 65° C. overnight. The reaction was allowed to cool to room temperature and the mixture was filtered through Celite. The solid was rinsed with ethyl acetate (100 ml) and the resulting filtrate was partitioned between ethyl acetate and saturated brine solution. The organic layer was washed with saturated brine (3×100 ml), dried over anhydrous Na$_2$SO$_4$ and concentrated in vacuo. The crude, colorless oil was chromatographed on silica to afford 5-oxo-pyrrolidine-1,2-dicarboxylic acid 2-benzyl ester 1-tert-butyl ester as a colorless oil (8.20 g, 0.026 mol, 59% yield). Analysis H$^1$ NMR (400 MHz, CDCl₃): 7.36 (5H, broad s), 5.20 (2H, d), 4.64 (1H, dd), 2.44–1.96 (4H, m), 1.41 (9H, s). MS (LC-MS): Calculated for C17H21NO5 319.14, found 320.19 (M+H)$^+$.

A solution of (2S)5-oxo-pyrrolidine-1,2-dicarboxylic acid 2-benzyl ester 1-tert-butyl ester (8.20 g, 0.026 mol, 1.0 equivalent) in anhydrous THF was cooled to 0° C. in an ice bath under N$_2$. A chilled 0.5M solution of 3,4-dimethoxyphenylmagnesium bromide in THF (52.1 mL, 0.026 mol, 1.0 equivalent) was slowly added. The reaction mixture was allowed to stir for two hours. The reaction was quenched upon addition of saturated NH$_4$Cl solution (10 ml). The mixture was partitioned between ethyl acetate and brine. The organic extract was washed with brine (3×100 ml). The ethyl acetate layer was dried over anhydrous Na$_2$SO$_4$ and concentrated in vacuo. The resulting crude blue oil was filtered through a layer of silica. The filtrate was concentrated in vacuo to afford 2-tert-butoxycarbonylamino-5-(3,4-dimethoxy-phenyl)-5-oxo-pentanoic acid benzyl ester (10.46 g, 0.023 mol, 88% yield). Analysis H$^1$ NMR (400 MHz, CDCl₃): 7.5–7.3 (6H, m), 7.0–6.7 (2H, m), 5.2 (2H, m), 4.0–3.8 (6H, m), 3.0 (1H, m), 2.6–1.9 (4H, m), 1.4 (9H, s). MS (LC-MS): Calculated for C25H31NO7 457.21, found 458.19 (M+H)$^+$.

A solution of (2S)2-tert-butoxycarbonylamino-5-(3,4-dimethoxy-phenyl)-5-oxo-pentanoic acid benzyl ester (10.46 g, 0.023 mol) in dichloromethane (150 ml) was cooled to 0° C. in an ice bath. TFA (40 ml) was slowly added to the stirring mixture and the reaction was allowed to warm to room temperature over two hours. The reaction mixture was concentrated in vacuo. The resulting residue was dissolved in ethyl acetate and the pH was adjusted to 7 with 1N NaOH. The organic extract was washed with brine (100 ml). The ethyl acetate extract was dried over anhydrous Na$_2$SO$_4$ and concentrated in vacuo to afford (2S)5-(3,4-dimethoxy-phenyl)-3,4-dihydro-2H-pyrrole-2-carboxylic acid benzyl ester TFA salt (7.24 g, 0.021 mol, 91% yield). MS (LC-MS): Calculated for C20H21NO4 339.15, found 340.16 (M+H)$^+$.

(2S)5-(3,4-Dimethoxy-phenyl)-3,4-dihydro-2H-pyrrole-2-carboxylic acid benzyl ester (7.24 g, 0.021 mol) was dissolved in methanol (100 ml) and added to a hydrogenation bottle containing Pd/C catalyst (75 mg). The reaction was hydrogenated at room temperature at 50 psi overnight. The reaction mixture was filtered through Celite and rinsed with methanol/ethyl acetate (1:1, 100 ml). The filtrate was concentrated in vacuo. The resulting crude residue was triturated with ether and ethyl acetate, filtered and dried to afford (2S,5R)5-(3,4-dimethoxy-phenyl)-pyrrolidine-2-carboxylic acid TFA salt as a white solid (3.00 g, 0.012 mol, 57% yield). Analysis H$^1$ NMR (400 MHz, DMSO): 7.18 (1H, s), 6.98 (2H, s), 4.42 (1H, d), 4.64 (1H, dd), 3.76 (7H, broad s), 2.24–2.10 (3H, m), 1.74 (1H, m). MS (LC-MS): Calculated for C13H17NO4 251.12, found 252.08 (M+H)$^+$.

The (2S,5R)5-(3,4-dimethoxy-phenyl)-pyrrolidine-2-carboxylic acid (3.00 g, 0.012 mol, 1.0 equivalent) was suspended in dichloromethane (50 ml) and DIEA (2.50 ml, 0.014 mol, 1.2 equivalents) and cooled to 0° C. in an ice bath. A 1.0M solution of Boc anhydride in THF (12.0 ml, 0.012 mol, 1.0 equivalent) was added and the reaction was allowed to stir and warm to room temperature overnight. The reaction mixture was washed with brine solution (2×50 ml). The organic extract was dried over anhydrous Na$_2$SO$_4$ and concentrated in vacuo to afford (2S,5R)5-(3,4-dimethoxy-phenyl)-pyrrolidine-1,2-dicarboxylic acid 1-tert-butyl ester (4.22, 0.012 mol, 100% yield). Analysis H$^1$ NMR (400 MHz, CDCl$_3$): 6.95 (1H, s), 6.80 (2H, s), 4.67 (1H, m), 4.50 (1H, m), 3.86 (6H, s), 2.52–1.89 (4H, m), 1.19 (9H, broad s). MS (LC-MS): Calculated for C18H25NO6 351.17, found 352.22 (M+H)$^+$.

A solution of (2S,5R)5-(3,4-dimethoxy-phenyl)-pyrrolidine-1,2-dicarboxylic acid 1-tert-butyl ester (2.50 g, 7.11 mmol, 1.0 equivalent), 4-chloro-3-methoxyaniline (1.12 g, 7.11 mmol, 1.0 equivalent), PyBrop coupling reagent (3.98 g, 8.54 mmol, 1.2 equivalents), and DIEA (1.86 ml, 10.7 mmol, 1.5 equivalents) in dichloromethane (35 ml) was allowed to stir at room temperature overnight. The reaction mixture was concentrated in vacuo. The resulting residue was dissolved in ethyl acetate (100 ml) and washed with 1N NaOH (3×100 ml). The organic extract was dried over anhydrous Na$_2$SO$_4$ and concentrated in vacuo. The crude oil was filtered through a layer of silica and eluted with ethyl acetate:hexanes (1:1). The filtrate was concentrated in vacuo to afford (2S,5R)2-(4-chloro-3-methoxy-phenylcarbamoyl)-5-(3,4-dimethoxy-phenyl)-pyrrolidine-1-carboxylic acid tert-butyl ester (3.48 g, 7.09 mmol, 100% yield). Analysis H$^1$ NMR (400 MHz, CDCl$_3$): 7.59 (1H, broad s), 7.23 (1H, m), 6.85–6.60 (4H, m) 4.64 (2H, m), 3.00 (3H, s), 3.83 (3H, s), 3.56 (3H, broad s), 2.62 (1H, broad m), 2.36 (1H, m), 2.11–1.89 (2H, m), 1.22 (9H, broad s). MS (LC-MS): Calculated for C25H31ClN2O6 490.19, found 491.15 (M+H)$^+$.

(2S,5R)2-(4-Chloro-3-methoxy-phenylcarbamoyl)-5-(3,4-dimethoxy-phenyl)-pyrrolidine-1-carboxylic acid tert-butyl ester (3.48 g, 7.09 mmol) was dissolved in dichloromethane (100 ml) and cooled to 0° C. in an ice bath. TFA (30 ml) was then added slowly to the stirring solution. The reaction was allowed to stir and warm to room temperature overnight. The reaction mixture was concentrated in vacuo. The pH of the resulting residue was adjusted to 8 with 1N NaOH and the product extracted into ethyl acetate. The extract was then washed with brine solution (2×100 ml), dried over anhydrous Na$_2$SO$_4$ and concentrated in vacuo. The crude oil was chromatographed to afford (2S,5R)5-(3,4-dimethoxy-phneyl)-pyrrolidine-2-carboxylic acid (4-chloro-3-methoxy-phenyl)-amide (2.77 g, 7.09 mmol, 100% yield). Analysis H$^1$ NMR (400 MHz, CDCl$_3$): 10.02 (1H, broad s), 7.59 (1H, broad s), 7.21 (1H, d), 7.03–6.82 (4H, m) 4.52–4.30 (2H, m), 3.90 (9H, m), 2.70–1.88 (5H, m). MS (LC-MS): Calculated for C20H23ClN2O4 390.13, found 391.16 (M+H)$^+$.

(2S,5R)5-(3,4-Dimethoxy-phenyl)-pyrrolidine-2-carboxylic acid (4-chloro-3-methoxy-phenyl)-amide was dissolved in anhydrous THF and cooled to 0° C. in an ice bath. A 0.5M solution of alane complex in toluene (42.6 ml, 21.3 mmol, 3.0 equivalents) was added slowly and the reaction was allowed to stir and warm to room temperature overnight. The reaction was quenched upon addition of ethyl acetate:methanol (1:1, 5 ml). The resulting slurry was filtered through Celite and rinsed with ethyl acetate. The filtrate was concentrated in vacuo to afford (2S,5R)(4-chloro-3-methoxy-phenyl)-[5-(3,3-dimethoxy-phenyl)-pyrrolidin-2-ylmethyl]-amine (1.80 g, 4.78 mmol, 67% yield). Analysis H$^1$ NMR (400 MHz, CDCl$_3$): 7.12 (1H, d), 6.98–6.90 (3H, m), 6.23 (1H, s), 6.19 (1H, d) 4.39–4.15 (2H, m), 3.76–3.53 (1H, m), 3.30–2.97 (2H, m), 2.34–1.55 (6H, m). MS (LC-MS): Calculated for C20H25ClN2O3 376.16, found 377.21 (M+H)$^+$.

A solution containing (2S,5R)(4-chloro-3-methoxy-phenyl)-[5-(3,3-dimethoxy-phenyl)-pyrrolidin-2-ylmethyl]-amine (1.80 g, 4.78 mmol, 1.0 equivalent), ethylbromoacetate (0.80 g, 4.78 mmol, 1.0 equivalent), and DIEA (0.87 ml, 5.02 mmol, 1.05 equivalents) in acetonitrile (25 ml) was allowed to stir at room temperature overnight. The reaction mixture was concentrated in vacuo. The resulting residue was dissolved in ethyl acetate (50 ml) and washed with 1N NaOH (2×25 ml). The ethyl acetate extract was dried over anhydrous Na$_2$SO$_4$ and concentrated in vacuo to afford a 2:1 mixture of regioisomers, (2S,5R)[2-[(4-chloro-3-methoxyphenylamino)-methyl]-5-(3,4-dimethoxy-phenyl)-pyrrolidin-1-yl]-acetic acid ethyl ester and {4-chloro-3-methoxyphenyl)-[5-(3,4-dimethoxy-phenyl)-pyrrolidin-2-ylmethyl]-amino}-acetic acid ethyl ester (2.21 g, 4.78 mmol, 100% yield). Analysis H$^1$ NMR (400 MHz, CDCl$_3$): 7.12 (1H, d), 6.98 (1H, s), 6.90 (1H, d), 6.82 (1H, dd), 6.74 (1H, m), 6.25–6.16 (2H, m), 4.64–4.50 (1H, m), 4.37, 3.60 (1H, split m), 4.27–3.90 (2H, m), 3.87 (9H, m), 3.46–3.00 (4H, m), 2.40–2.06 (2H, m), 1.92–1.66 (2H, m), 1.34–1.14 (3H, m). MS (LC-MS): Calculated for C24H31ClN2O5 462.19, found 463.21 (M+H)$^+$.

A solution of (2R,5S)[2-[(4-chloro-3-methoxy-phenylamino)-methyl]-5-(3,4-dimethoxy-phenyl)-pyrrolidin-1-yl]-acetic acid ethyl ester (125 mg, 0.27 mmol, 1.0 equivalent) in THF (5 ml) was cooled to 0° C. in an ice bath. NaH (16 mg, 0.40 mmol, 1.5 equivalents) was slowly added to the stirring solution. The reaction was allowed to stir and warm to room temperature overnight. The reaction mixture was cooled to room temperature and partitioned between ethyl acetate and 1N NaOH. The organic extract was dried over anhydrous Na$_2$SO$_4$ and concentrated in vacuo. The crude oil was loaded onto silica and rinsed with hexanes to remove impurities. The product was eluted with ethyl acetate and reconcentrated to afford (6R,9S)2-(4-chloro-3-methoxyphenyl)-6-(3,4-dimethoxy-phenyl)-hexahydro-pyrrolo[1,2-a]pyrazin-3-one (80 mg, 0.19 mmol, 70% yield). Analysis H$^1$ NMR (400 MHz, CDCl$_3$): 7.39 (1H, d), 6.95 (1H, s), 6.91 (2H, m), 6.83 (2H, d), 3.90 (9H, m), 3.71 (2H, m), 3.58 (1H, d), 3.25 (1H, t), 2.96 (1H, d), 2.84 (1H, m), 2.29 (1H, m), 2.08 (1H, m), 1.88 (1H, m), 1.71 (1H, m). MS (LC-MS): Calculated for C22H25ClN2O4 416.15, found 417.23 (M+H)$^+$. Upon scale-up, heating (50° C.) is required for ring closure. Epimerization is observed. Cis and trans isomers are separable by flash chromatography.

A solution of 2-(4-chloro-3-methoxy-phenyl)-6-(3,4-dimethoxy-phenyl)-hexahydro-pyrrolo[1,2-a]pyrazin-3-one (80 mg, 0.19 mmol, 1.0 equivalents) in THF (2 ml) was cooled to 0° C. in an ice bath. A 0.5M solution of alane complex in toluene (1.14 ml, 0.57 mmol, 3.0 equivalents) was slowly added and the reaction was allowed to stir for one hour. The reaction was quenched upon addition of ethyl acetate:methanol (1:1, 1 ml). The resulting slurry was filtered through a layer of silica and concentrated in vacuo to afford (6R,9S)2-(4-chloro-3-methoxy-phenyl)-6-(3,4-dimethoxy-phenyl)-octahydro-pyrrolo[1,2-a]pyrazine (compound 9; 49 mg, 0.12 mmol, 63% yield). Analysis $H^1$ NMR (400 MHz, $CDCl_3$): 7.20 (1H, d), 6.93 (1H, s), 6.90 (1H, d), 6.82 (1H, d), 6.52 (1H,s), 6.49 (1H, d), 3.90 (9H, m), 3.73 (1H, d), 3.51 (1H, d), 3.21 (1H, t), 2.93 (2H, m), 2.68 (1H, t), 2.44 (1H, m), 2.20 (2H, broad t), 1.92 (1H, m), 1.65 (2H, m). MS (LC-MS): Calculated for C22H27ClN2O3 402.17, found 403.23 (M+H)+. Chiral HPLC analysis revealed>98% enantiomeric purity.

XI. (4-Trifluoromethyl-phenyl)-{4-[1-(4-Methoxy2,3-Dimethyl-phenyl)-ethyl]-piperazin-1-yl}-methanone via Scheme K

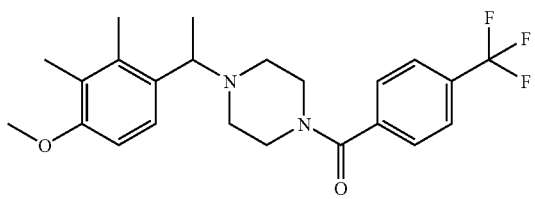

A mixture of 2,3-dimethyl 4-methoxy benzaldehyde (1 g, 3.05 mmol), 1 equivalent of piperazine-1-carboxylic acid tert-butyl ester (0.57 g, 3.05 mmol), 1 equivalent of benzotriazole in ethanol was stirred at room temperature for 30 minutes. The solvent was removed and the reaction was dried under vacuum. The reaction mixture was then dissolved in anhydrous THF(20 ml) under $N_2$ at −78° C. Then 3 equivalents (3.05 ml) of methyl magnesium bromide (3M in THF) was added to the solution slowly. The reaction mixture was kept at this temperature for 2 hours and warmed up to room temperature for overnight. The mixture was washed with 2N NaOH and water and extracted with ethyl acetate (2×30 ml). The combined organic layers were dried over $MgSO_4$. After removal of organic solvent, the residue was purified by a flash column on silica gel eluted with 1:1 EtOAC:Hexane first, then with 10% MeOH(NH3) in dichloromethane. 4-[1-(4-methoxy-2,3-dimethyl-phenyl)-ethyl]-piperazine-1-carboxylic acid tert-butyl ester was obtained as a yellow oil (0.59 g, 56%). Analysis $H^1$ NMR (400 MHz, $CDCl_3$): 7.21 (1H, d), 6.68 (1H, d), 3.8 (3H, s), 3.58 (1H, q), 3.38 (3H, m), 2.45 (2H, m), 2.37 (2H, m), 2.24 (3H, s), 2.18 (3H, s), 1.43 (9H, s), 1.24 (3H, d). MS (LC-MC): Calculated for C20H32N2O3 348.48, found 349.29 (M+).

To an ice chilled solution containing 4-[1-(4-methoxy-2,3-dimethyl-phenyl)-ethyl]-piperazine-1-carboxylic acid tert-butyl ester (0.4 g 1.38 mmol) and 10 ml dichloromethane, was added trifluoroacetic acid (2 ml) dropwise. The reaction was stirred at room temperature for 2 hours. The reaction was concentrated. The residue was purified by flash chromatography on silica gel eluted with 10% MeOH (NH3)/dichloromethane. 1-[1-(4-Methoxy-2,3-dimethyl-phenyl)-ethyl]-piperazine was obtained as a yellow oil (0.16 g 47%). Analysis $H^1$ NMR (400 MHz, $CDCl_3$): 7.23 (1H, d), 6.69 (1H, d), 3.8 (3H, s), 3.55 (1H, q), 3.484 (2H, s), 2.838 (4H, m), 2.47 (2H, m), 2.38 (2H, m), 2.271 (3H, s), 2.167 (3H, s), 1.26 (3H, d). MS (LC-MS): Calculated for C15H24N2O 248.36, found 249.25 (M+).

1-[1-(4-Methoxy-2,3-dimethyl-phenyl)-ethyl]-piperazine (0.02 g, 0.081 mmole) was dissolved in anhydrous toluene and 1N NaOH (1:1) at room temperature. The 4-trifluoromtheyl benzoyl chloride (0.013 ml, 0.081 mmole) was added into the reaction mixture. The reaction mixture was stirred at room temperature for 30 minutes. The mixture was washed with 1N NaOH, extracted with EtOAC. The combined organic layers were dried over $MgSO_4$. After removal organic solvent, the residue was purified by SCX column eluted with MeOH and 10% MeOH (NH3) in dichloromethane. (4-Trifluoromethyl-phenyl)-{4-[1-(4-Methoxy2,3-Dimethyl-phenyl)-ethyl]-piperazin-1-yl}-methanone (compound 10) was obtained as a pale yellow oil (0.010 g 30%). Analysis $H^1$ NMR (400 MHz, $CDCl_3$): 7.65 (2H, d), 7.495 (2H, d), 7.19 (1H, d), 6.689 (1H, d), 3.764 (3H, s), 3.682 (1H, q), 3.317 (2H, m), 2.506 (6H, m), 2.266 (3H, s), 2.164 (3H, s) 1.286 (3H, d). MS (LC-MS): Calculated for C23H27F3N2O2 420.47, found 421.26 (M+).

XII. {5-[1-4-Methoxy-2,3-dimethyl-phenyl)-ethyl]-(1S,4S)-2,5-diaza-bicyclo[2.2.1]hept-2yl}-(4-trifluoromethyl-phenyl)-methanone (compound 11)

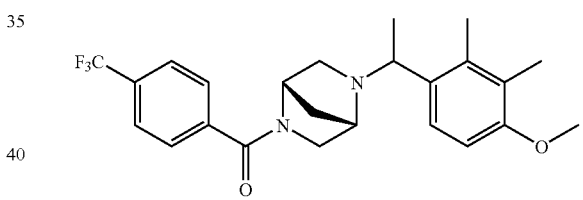

(1S,4S)-(−)-2,5-Diaza-bicyclo[2.2.1]heptane-2-carboxylic acid tert-butyl ester (0.2 M 5% NMM/toluene, 0.100 mL, 0.020 mmol) was added to a ½ dram vial followed by 4-methoxy-2,3-dimethyl-benzaldehyde (0.2 M toluene, 0.110 mL, 0.022 mmol) and benzotriazole (0.2 M EtOH, 0.110 mL, 0.022 mmol). The vial was concentrated under reduced pressure at 40° C. (IR-Dancer). The resulting residue was dissolved in THF (0.20 mL, anhydrous), and the vial was capped under $N_2$ flow then treated with MeMgBr (1.0 M THF, 0.050 mL, 0.050 mmol). The vial was shaken at room temperature for 0.5 hours, then treated with HCl (4.0 M dioxane, 0.10 mL). The vial was kept at 50° C. overnight, then basified with NaOH (10% aqueous (w/w), 0.50 mL) and treated with 4-trifluoromethyl benzoyl chloride (0.2 M toluene, 0.15 mL, 0.03 mmol). The vial was shaken briefly, then let stand at room temperature 0.5 hours, and was then diluted with 1% $Et_2NH$ in toluene (v/v, 0.50 mL). The vial was shaken vigorously, then let stand until the phases fully separated. The upper organic phase was removed and deposited on a SCX SPE cartridge (0.5 g SCX, 3 mL cartridge). The cartridge was eluted to waste with 25% MeOH in EtOAc (v/v, 3 mL) and eluted to collect with EtOAc/MeOH/

Et₃N (10:1:1 v/v/v, 3 mL). The eluted solution was concentrated under N₂ flow, then under reduced pressure. The product (compound 11) was obtained as a thick yellow oil (0.0057 g, 66%). Analysis: ¹HMR (400 MHz, CDCl₃): mixture of diastereomers/rotomers, diagnostic resonances: 3.821, 3.816, 3.791, 3.782 (3H (combined), S (OCH₃)) MS (LCMS): Calculated for C24H27F3N2O2 432.20, found 433.17 [M+H]⁺.

XIII. (±)-trans-and (±)-cis-2-(4-Chloro-3-methoxy-phenyl)-6-(3,4-dimethoxy-phenyl)-hexahydro-pyrrolo[1,2-a]pyrazine (compound 12)

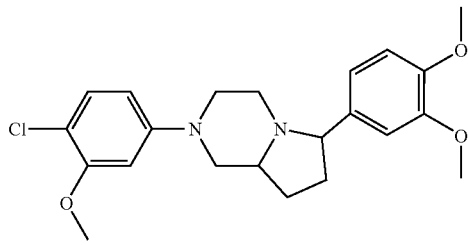

(4-Chloro-3-methoxy-phenyl)-[5-(3,4-dimethoxy-phenyl)-pyrrolidin-2-ylmethyl]-amine (104 mg, 0.276 mmol; prepared as described above) was dissolved in a solution of CH₂Cl₂ (10 mL) and DMAP (74.1 mg, 0.667 mmol). The solution was cooled to 0° C. and oxalyl chloride (0.029 mL, 0.331 mmol) was added dropwise. After 30 minutes, the reaction was quenched with the addition of ice water (10 mL). The organic phase was extracted with 1N HCl (20 mL), 1N NaOH (20 mL), and brine (20 mL). The organic phase was dried over Na₂SO₄ and the solvent removed under reduced pressure. The crude product ((±)-cis-2-(4-chloro-3-methoxy-phenyl)-6-(3,4-dimethoxy-phenyl)-hexahydro-pyrrolo[1,2-a]pyrazine-3,4-dione) was purified by preparatory TLC eluting with hexanes/acetone (2:1) as a glassy colorless solid (49.7 mg, 41.8%). ¹H NMR (CDCl₃) δ7.39 (d, J=8.7 Hz, 1H, ArH), 7.08 (d, J=2.1 Hz, 1H, ArH), 6.85–6.81 (m, 3H, ArH), 6.75 (dd, J=8.7, 2.1 Hz, 1H, ArH), 5.20 (d, J=9.0 Hz, 1H), 4.35–4.32 (m, 1H), 4.16–3.95 (m, 2H), 3.90 (s, 3H, OCH₃), 3.89 (s, 3H, OCH₃), 3.86 (s, 3H, OCH₃), 2.46–2.40 (m, 1H), 2.17–1.87 (m, 2H). LCMS m/z 331 (M⁺+1, 100, 2.07 min).

(±)-cis-2-(4-Chloro-3-methoxy-phenyl)-6-(3,4-dimethoxy-phenyl)-hexahydro-pyrrolo[1,2-a]pyrazine-3,4-dione (49.7 mg, 0.115 mmol) was dissolved in dry THF (10 mL) and BH₃.THF (1 mL, 1 mmol) was added dropwise to the mixture, which was then heated at reflux overnight. The solution was cooled to 0° C. and MeOH (2 mL) was added dropwise. The solvent was removed by evaporation and the crude product was dissolved in MeOH (10 mL) and 12N HCl (2 mL). The solution was refluxed for 4 hours. The reaction mixture was concentrated (~2 mL) followed by basification with 1N NaOH. The aqueous solution was extracted with CH₂Cl₂ (3×25 mL). The combined organic extracts were washed with brine, dried over Na₂SO₄, and concentrated under reduced pressure. The crude products were purified by preparatory TLC eluting with CH₂Cl₂/MeOH (97:3) to yield the (±)-cis-(20.3 mg, 43.8%) and (±)-trans-2-(4-chloro-3-methoxy-phenyl)-6-(3,4-dimethoxy-phenyl)-hexahydro-pyrrolo[1,2-a]pyrazine (14.3 mg, 30.9%) with (±)-cis-2-(4-chloro-3-methoxy-phenyl)-6-(3,4-dimethoxy-phenyl)-hexahydro-pyrrolo[1,2-a]pyrazine eluting further up the plate. (±)-trans-2-(4-Chloro-3-methoxy-phenyl)-6-(3,4-dimethoxy-phenyl)-hexahydro-pyrrolo[1,2-a]pyrazine ¹H NMR (CDCl₃) δ 7.20 (d, J=8.7 Hz, 1H, ArH), 6.89–6.83 (m, 3H, ArH), 6.47–6.40 (m, 2H, ArH), 4.16 (m, 1H), 3.95–3.84 (m, 1H), 3.90 (s, 3H, OCH₃), 3.88 (s, 6H, OCH₃), 3.58–3.46 (m, 1H), 3.41–3.36 (m, 1H), 3.26–3.22 (m, 1H), 2.99–2.71 (m, 3H), 2.34–2.20 (m, 2H), 1.95–1.83 (m, 1H), 1.64–1.54 (m, 1H). LCMS m/z 403 (M⁺+1, 100, 1.90 min).

XIV. Compounds 13–143

The compounds shown in TABLE I as compounds 13–143 were prepared via methods A–M described above.

TABLE I

| EX # | STRUCTURE | NAME | 1H NMR (400 MHz, CDCl3) | MS | Method |
|---|---|---|---|---|---|
| 13 | 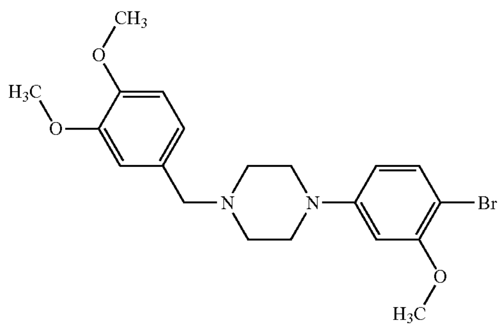 | 1-(4-bromo-3-methoxyphenyl)-4-(3,4-dimethoxybenzyl)piperazine | 7.32(1H, d), 6.89(3H, m), 6.42 2H, m), 3.85(9H, m), 3.51(2H, s), 3.18(4H, t), 2.59(4H, t). | 422.21(M+) | A |
| 14 | 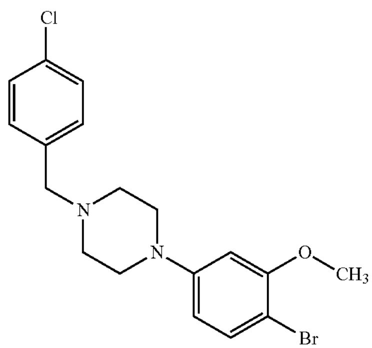 | 1-(4-bromo-3-methoxyphenyl)-4-(4-chlorobenzyl)piperazine | 7.38–7.25(5H, m), 6.44(1H, d), 6.40(1H, dd), 3.84(3H, s), 3.47 (2H, s), 3.2(4H, m), 2.60(4H, m) | 397.0(M+) | A |

TABLE I-continued

| EX # | STRUCTURE | NAME | 1H NMR (400 MHz, CDCl3) | MS | Method |
|---|---|---|---|---|---|
| 15 | 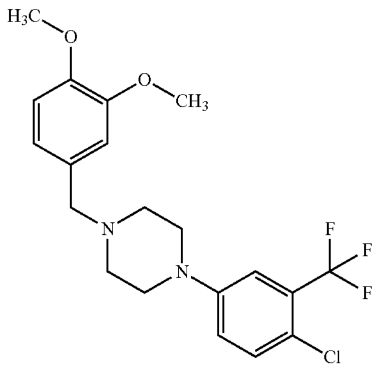 | 1-[4-chloro-3-trifluoromethyl)phenyl]-4-(3,4-dimethoxybenzyl)piperazine | | 415.2(M+) | A |
| 16 | 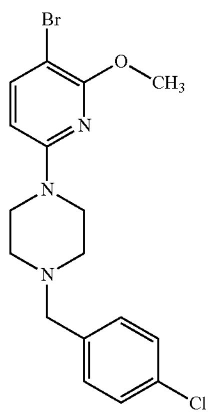 | 1-(5-bromo-6-methoxypyridin-2-yl)-4-(4-chlorobenzyl)piperazine | 7.45(1H, d), 7.30(5H, m), 6.04 (1H, d), 3.90(3H, s), 3.45(6H, m), 2.47(4H, m) | 398.0(M+) | A |

TABLE I-continued

| EX # | STRUCTURE | NAME | 1H NMR (400 MHz, CDCl3) | MS | Method |
|---|---|---|---|---|---|
| 17 | 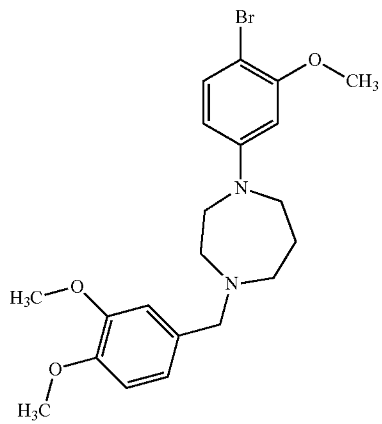 | 1-(4-bromo-3-methoxyphenyl)-4-(3,4-dimethoxybenzyl)-1,4-diazepane | 7.24(1H, d), 6.90–6.80(3H, m), (4H, m), 2.77(2H, m), 2.62(2H, m), 1.95(2H, m) | 435.4(M+) | A |
| 18 | 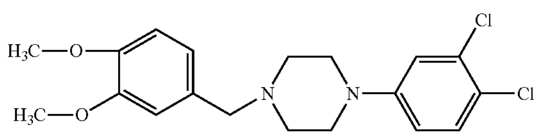 | 1-(3,4-dichlorophenyl)-4-(3,4-dimethoxybenzyl)piperazine | 7.27(1H, d), 6.94(1H, d), 6.91(1H, s), 6.83–6.85(m, 2H), 6.72(1H, dd), 3.90(d, 6H), 3.17(2H, t), 2.57(2H, t) | 382(M+) | A |
| 19 | 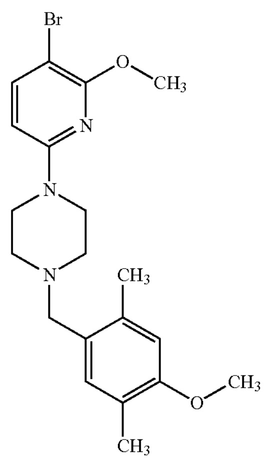 | 1-(5-bromo-6-methoxypyridin-2-yl)-4-(4-methoxy-2,5-dimethylbenzyl)piperazine | 7.55(1H, d), 7.03(1H, d), 6.64 (1H, d), 6.03(1H, d), 3.92(6H, d), 3.44(6H, d), 2.52(4H, d), 2.24 (6H, dd). | 420.22(M+) | A |

TABLE I-continued
| EX # | STRUCTURE | NAME | 1H NMR (400 MHz, CDCl3) | MS | Method |
|---|---|---|---|---|---|
| 20 | 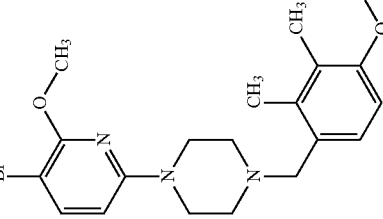 | 1-(5-bromo-6-methoxypyridin-2-yl)-4-(4-methoxy-2,3-dimethylbenzyl)piperazine | 7.55(1H, d), 7.01(1H, d), 6.68(1H, d), 6.08(1H, d), 3.85(6H, d), 3.44(6H, m), 2.56(4H, m), 2.23(6H, d). | | A |
| 21 | 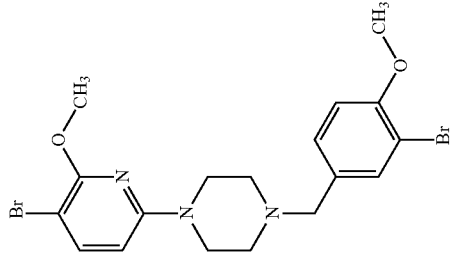 | 1-(3-bromo-4-methoxybenzyl)-4-(5-bromo-6-methoxypyridin-2-yl)piperazine | 7.56(2H, t), 7.21(1H, m), 6.83(1H, d), 6.06(1H, d), 3.88(6H, d), 3.47(6H, m), 2.55(4H, m). | 472.14 M+ | A |

TABLE I-continued

| EX # | STRUCTURE | NAME | 1H NMR (400 MHz, CDCl3) | MS | Method |
|---|---|---|---|---|---|
| 22 | 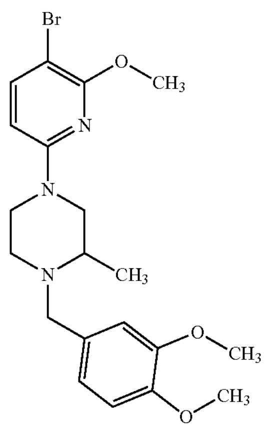 | 4-(5-bromo-6-methoxypyridin-2-yl)-1-(3,4-dimethoxybenzyl)-2-methylpiperazine | 7.51(1H, d), 6.85(3H, m), 6.06 (1H, d), 4.05(1H, m), 3.923(2H, s), 3.905(9H, dd), 2.9 (6H, m), 1.22(3H, d) | 436.25 M+ | A |
| 23 | 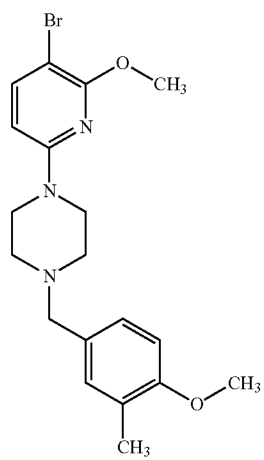 | 1-(5-bromo-6-methoxypyridin-2-yl)-4-(4-methoxy-3-methylbenzyl)piperazine | 7.49(1H, d), 7.08(2H, m), 6.79 (1H, d), 6.06(1H, d), 3.88(6H, d), 3.47(6H, m), 2.58(4H, m), 2.2(3H, s). | 406.21 M+ | A |

TABLE I-continued
| EX # | STRUCTURE | NAME | 1H NMR (400 MHz, CDCl3) | MS | Method |
|---|---|---|---|---|---|
| 24 | 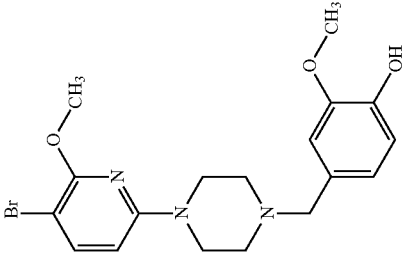 | 4-{[4-(5-bromo-6-methoxypyridin-2-yl)piperazin-1-yl]methyl}-2-methoxyphenol | 7.45(1H, d), 6.83(3H, m), 6.43 (1H, s), 6.08(1H, d), 3.87(6H, d), 3.47(6H, m), 2.55(4H, m). | 410.16(M + 2) | A |
| 25 | 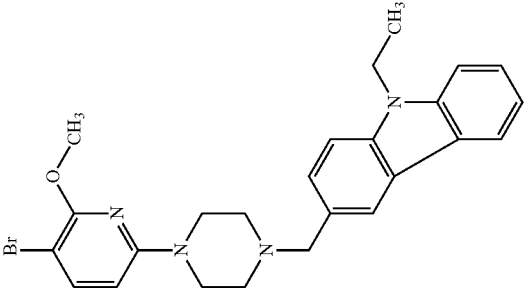 | 3-{[4-(5-bromo-6-methoxypyridin-2-yl)piperazin-1-yl]methyl}-9-ethyl-9H-carbazole | 8.07(2H, m), 7.43(5H, m), 7.21 (1H, m), 6.08(1H, m), 4.37(2H, q), 3.92(3H, s), 3.75(2H, s), 3.5(4H, m), 2.59(4H, m), 1.43(3H, t). | 479.24 M+ | A |

TABLE I-continued

| EX # | STRUCTURE | NAME | 1H NMR (400 MHz, CDCl3) | MS | Method |
|---|---|---|---|---|---|
| 26 | 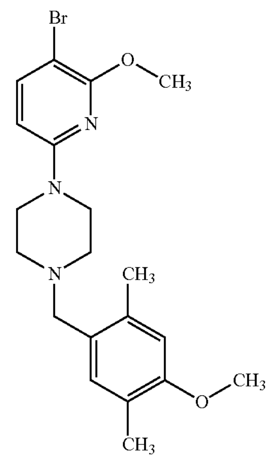 | 1-(4-bromo-3-methoxyphenyl)-4-(4-methoxy-2,5-dimethylbenzyl)piperazine | 7.37(1H, d), 6.98(1H, s), 6.63 (1H, s), 6.43(1H, s), 6.38(1H, d), 3.83(6H, d), 3.44(2H, s), 3.17(4H, m), 2.59(4H, m), 2.2(3H, s). | 419.23 M+ | A |
| 27 | 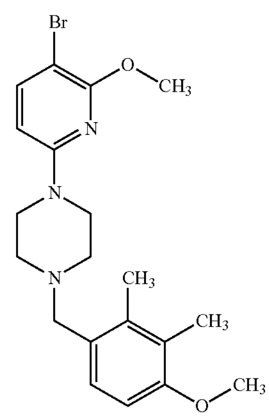 | 1-(4-bromo-3-methoxyphenyl)-4-(4-methoxy-2,3-dimethylbenzyl)piperazine | 7.37(1H, d), 7.01(1H, d), 6.62 (1H, s), 6.43(1H, s), 6.38(1H, d), 3.82(6H, d), 3.44(2H, s), 3.17(4H, m), 2.59(4H, m), 2.24(3H, s), 2.16 (3H, s). | 419.21 M+ | A |

TABLE I-continued

| EX # | STRUCTURE | NAME | 1H NMR (400 MHz, CDCl3) | MS | Method |
|---|---|---|---|---|---|
| 28 | 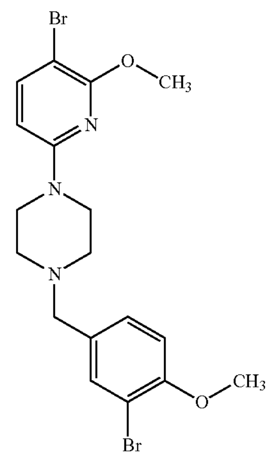 | 1-(3-bromo-4-methoxybenzyl)-4-(4-bromo-3-methoxyphenyl)piperazine | 7.57(1H, s), 7.36(1H, d), 7.24(1H, d), 6.84(1H, d), 6.43(1H, d), 6.38(1H, d), 3.85(6H, d), 3.44(2H, s), 3.17(4H, m), 2.59(4H, m). | 471.07 M+ | A |
| 29 | 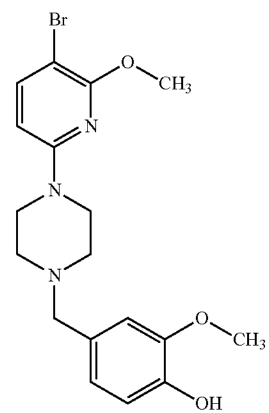 | 4-[[4-(4-bromo-3-methoxyphenyl)piperazin-1-yl]methyl]-2-methoxyphenol | 7.39(1H, d), 6.83(3H, m), 6.43(1H, s), 6.38(1H, d), 3.83(6H, d), 3.44(2H, s), 3.17(4H, m), 2.59(4H, m), 2.1(3H, s). | 409.18(M + 2) | A |

TABLE I-continued

| EX # | STRUCTURE | NAME | 1H NMR (400 MHz, CDCl3) | MS | Method |
|---|---|---|---|---|---|
| 30 | 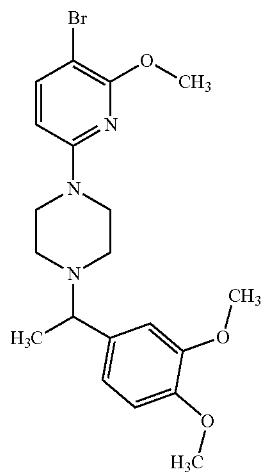 | 1-(4-bromo-3-methoxyphenyl)-4-[1-(3,4-dimethoxyphenyl)-ethyl]piperazine | 7.39(1H, d), 6.84(3H, m), 6.24 (2H, m), 3.82(9H, m), 3.49(1H, q), 3.18(4H, m), 2.60(4H, m), 1.29 (3H, t). | 436.3 M+ | B |
| 31 | 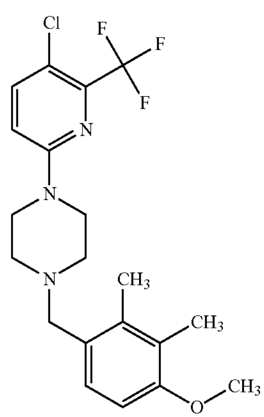 | 1-[4-chloro-3-(trifluoromethyl)phenyl]-4-(4-methoxy-2,3-dimethylbenzyl)piperazine | 7.34(1H, d), 7.0(3H, m), 6.67 (1H, d), 3.85(3H, s), 3.44(2H, s), 3.19(4H, m), 2.59(4H, m). | 413.3 M+ | A |

TABLE I-continued

| EX # | STRUCTURE | NAME | 1H NMR (400 MHz, CDCl3) | MS | Method |
|---|---|---|---|---|---|
| 32 | 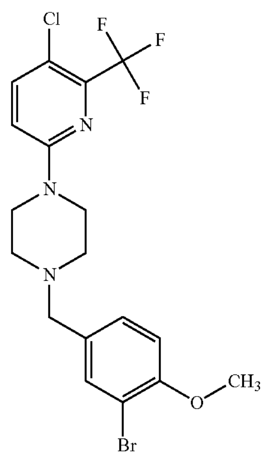 | 1-(3-bromo-4-methoxybenzyl)-4-[4-chloro-3-(trifluoromethyl)-phenyl]piperazine | 7.55(1H, s), 7.23(3H, m), 6.90 (1H, d), 6.83(1H, d), 3.85(6H, s), 3.44(2H, s), 3.19(4H, m), 2.59 (4H, m). | 463.23 M+ | A |
| 33 | 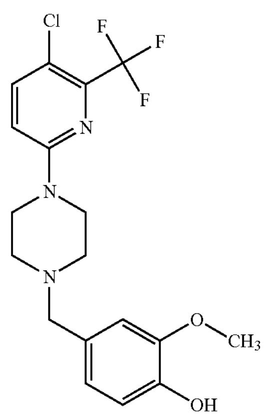 | 4-({4-[4-chloro-3-(trifluoromethyl)phenyl]piperazin-1-yl}methyl)-2-methoxyphenol | 7.35(1H, d), 7.14(1H, d), 6.93 (4H, m), 3.85(3H, s), 3.44(2H, s), 3.19(4H, m), 2.59(4H, m). | | A |

TABLE I-continued

| EX # | STRUCTURE | NAME | 1H NMR (400 MHz, CDCl3) | MS | Method |
|---|---|---|---|---|---|
| 34 | 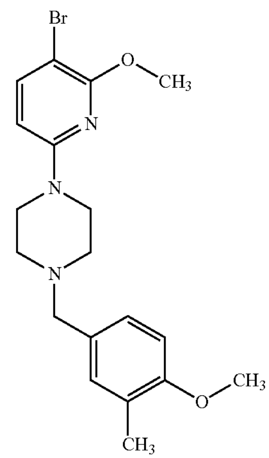 | 1-(4-bromo-3-methoxyphenyl)-4-(4-methoxy-3-methylbenzyl)piperazine | 7.37(1H, d), 7.11(2H,d), 6.78 (1H, d), 6.43(1H, s), 6.38(1H, d), 3.85(6H, d), 3.44(2H, s), 3.17(4H, m), 2.59(4H, m), 2.20(3H, s). | 407.1(M + 2) | A |
| 35 | 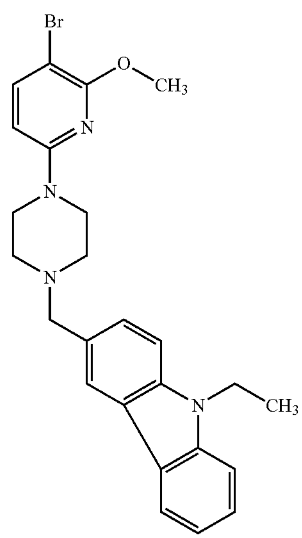 | 3-[[4-(4-bromo-3-methoxyphenyl)piperazin-1-yl]methyl]-9-ethyl-9H-carbazole | 8.07(3H, m), 7.38(6H, m), 6.42 (1H, m), 4.84(3H, s), 4.37(2H, q), 3.85(2H, s), 3.21(4H, m), 2.64 (4H, m), 1.43(3H, t). | 480.1(M + 2) | A |

TABLE I-continued

| EX # | STRUCTURE | NAME | 1H NMR (400 MHz, CDCl3) | MS | Method |
|---|---|---|---|---|---|
| 36 | (structure) | 1-[4-chloro-3-(trifluoromethyl)-phenyl]-4-(4-methoxy-3-methylbenzyl)piperazine | 7.31(1H, m), 7.08(3H, m), 6.93 (1H, m), 6.76(1H, m), 4.54(1H, s), 3.82(3H, s), 3.47(1H, s),3.2(4H, m), 2.58(4H, m), 2.21(3H, s). | 399.3 M+ | A |
| 37 | (structure) | 5-bromo-4-methoxy-2-[4-(4-methoxy-2,3-dimethylbenzyl)piperazin-1-yl]pyrimidine | 8.11(1H, d), 7.08(1H, d), 6.67 (1H, d), 4.64(2H, s), 3.98(4H, m), 3.82(10H, m), 2.31(3H, s), 2.2 (3H, s). | 421.24 M+ | A |

TABLE I-continued

| EX # | STRUCTURE | NAME | 1H NMR (400 MHz, CDCl3) | MS | Method |
|---|---|---|---|---|---|
| 38 | 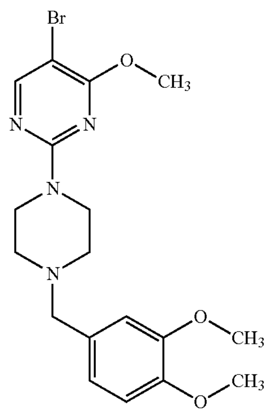 | 5-bromo-2-[4-(3,4-dimethoxybenzyl)piperazin-1-yl]-4-methoxypyrimidine | | | A |
| 39 | 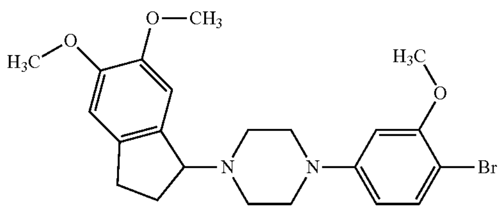 | 1-(4-bromo-3-methoxyphenyl)-4-(5,6-dimethoxy-2,3-dihydro-1H-indan-1-yl)piperazine | 7.38(1H, d), 6.88(1H, s), 6.77(1H, s), 6.38–6.47(2H, m) | 447,449(M+, M + 2) | B |
| 40 | 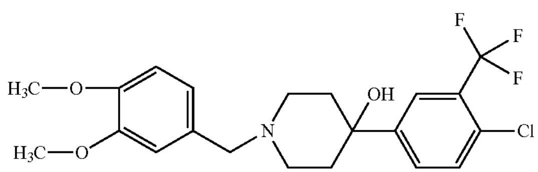 | 4-[4-chloro-3-(trifluoromethyl)phenyl]-1-(3,4-dimethoxybenzyl)piperidin-4-ol | 7.85(1H, d), 7.61(1H, m), 7.46 (1H, d), 6.80–6.90(3H, m), 3.90 (6H, d), 3.41(1H, m), 3.03(1H, m), 2.77(1H, m), 2.21–2.42(2H, m), 1.96–2.19(2H, m), 1.60–1.80(2H, m), 1.40(3H, d) | 444 M+ | A |

TABLE I-continued
| EX # | NAME | MS | Method |
|---|---|---|---|
| 41 | 1-(5-bromo-6-methoxypyridin-2-yl)-4-[1-(3,4-dimethoxyphenyl)ethyl]piperazine | | B |
| 42 | 2-(4-chloro-3-methoxy-phenyl)-6-(3,4-dimethoxy-phenyl)-octahydro-pyrido[1,2-a]pyrazin-8-one (racemic and R,S) | 431.15 M+ | B |
1H NMR (400 MHz, CDCl3):
Ex 41: 7.49(1H, d), 6.82(3H, m), 6.03 (1H, d), 3.89(9H, m), 3.45(4H, m), 3.37(1H, q), 2.51(4H, m), 1.41 (3H, d)
Ex 42: 7.19(1H, d), 6.86(3H, m), 6.46 (1H, m), 6.41(1H, dd), 3.91(3H, s), 3.89(3H, s), 3.87(3H, s), 3.44(2H, m), 3.30(2H, dd), 2.78(4H, m), 2.50(3H, m), 2.08(1H, td)
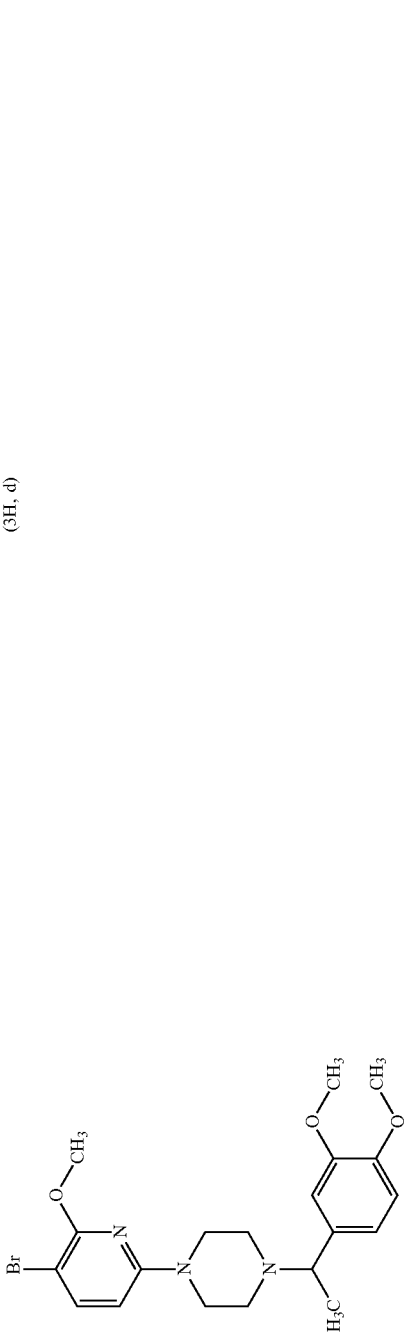

TABLE I-continued

| EX # | NAME | STRUCTURE | 1H NMR (400 MHz, CDCl3) | MS | Method |
|---|---|---|---|---|---|
| 43 | (2S)-4-(5-bromo-6-methoxypyridin-2-yl)-1-(3,4-dimethoxybenzyl)-2-methylpiperazine | 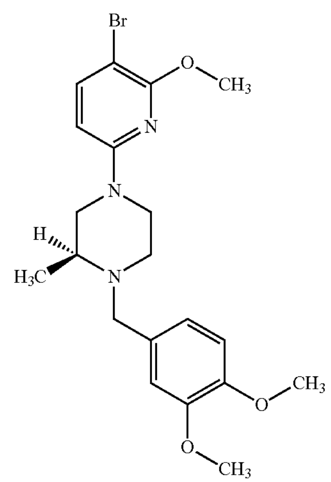 | 7.51(1H, d), 6.85(3H, m), 6.04 (1H, d), 4.15(1H, q), 3.91(9H, m), 3.23(4H, m), 2.56(4H, m), 1.25 (3H, d). | 436.25 M+ | A |
| 44 | 1-(5-bromo-6-methoxypyridin-2-yl)-4-(5,6-dimethoxy-2,3-dihydro-1H-indan-1-yl)piperazine | 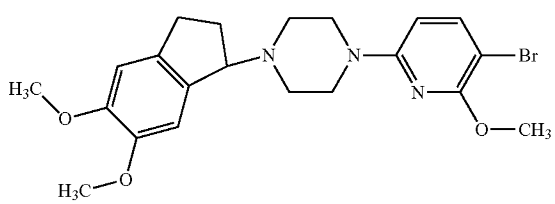 | 7.51(1H, d), 6.90(1H, s), 6.75(1H, s), 6.05(1H, d), 4.38(1H, t), 3.88 (9H, t), 3.50(4H, m), 2.78–2.90 (2H, m), 2.56(4H, m), 2.10(2H, m) | | B |

TABLE I-continued

| EX # | STRUCTURE | NAME | 1H NMR (400 MHz, CDCl3) | MS | Method |
|---|---|---|---|---|---|
| 45 | 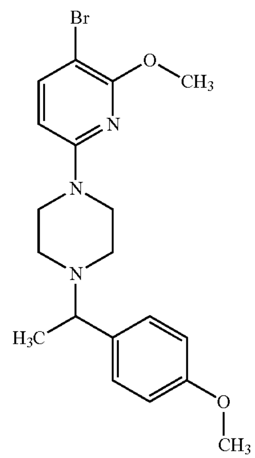 | 1-(4-bromo-3-methoxyphenyl)-4-[1-(4-methoxyphenyl)ethyl]piperazine | 7.34(1H, d), 7.23(2H, d), 6.86(2H, d), 6.44(1H, d), 6.36(1H, d), 3.85 (3H, s), 3.80(3H, s), 3.42(1H, m), 3.16(4H, m), 2.61(4H, m), 1.41 (3H, d). | 405.24 M+ | B |
| 46 | 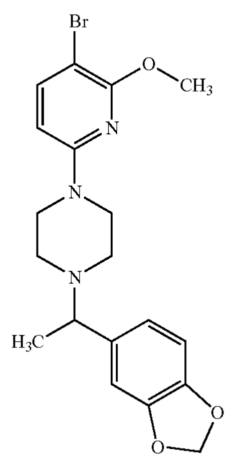 | 1-(1-benzo[1,3]dioxol-5-yl-ethyl)-4-(4-bromo-3-methoxyphenyl)piperazine | 7.33(2H, m), 7.04(2H, m), 6.64 (1H, d), 6.43(1H, m), 6.05(2H, s), 4.43(1H, m), 3.89(3H, s), 3.14 (4H, m), 2.49(4H, m), 1.69(3H, d). | 421.23 M+ | B |

TABLE I-continued

| EX # | STRUCTURE | NAME | 1H NMR (400 MHz, CDCl3) | MS | Method |
|---|---|---|---|---|---|
| 47 | 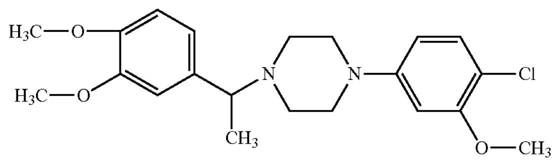 | 1-(4-chloro-3-methoxyphenyl)-4-[1-(3,4-dimethoxyphenyl)ethyl]piperazine (racemic and R) | 7.18(1H, d), 6.83–6.91(3H, m), 6.41–6.44(2H, m), 3.87(9H, t), 3.23(1H, q), 3.15(4H, t)2.51–2.65(4H, m), 1.38(3H, d) | 391 M+ | B |
| 48 | 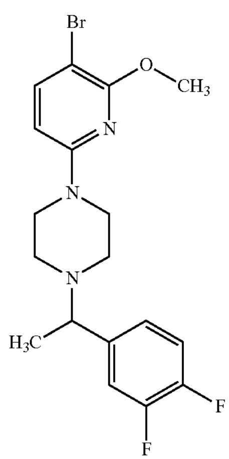 | 1-(4-bromo-3-methoxyphenyl)-4-[1-(3,4-difluorophenyl)ethyl]piperazine | 7.36(2H, m), 6.97(2H, m), 6.64(1H, s), 6.42(1H, d), 4.37(1H, m), 3.98(3H, s), 4.46(4H, m), 3.89(4H, m), 1.83(3H, d). | 410.28 M+ | B |

TABLE I-continued

| EX # | STRUCTURE | NAME | 1H NMR (400 MHz, CDCl3) | MS | Method |
|---|---|---|---|---|---|
| 49 | 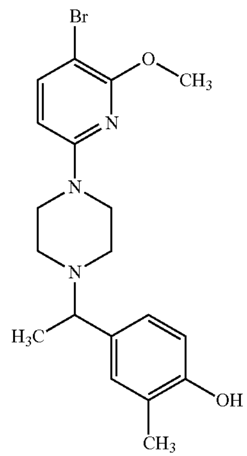 | 4-[1-[4-(4-bromo-3-methoxyphenyl)piperazin-1-yl]ethyl]-2-methylphenol | 7.78(2H, m), 7.32(1H, d), 7.07 (2H, m), 6.73(2H, m), 3.84(3H, s), 3.17(1H, m), 3.16(4H, m), 2.54 (4H, m), 1.41(3H, d) | 405.36 M+ | B |
| 50 | 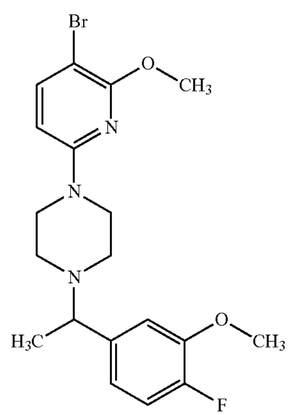 | 1-(4-bromo-3-methoxyphenyl)-4-[1-(4-fluoro-3-methoxyphenyl)ethyl]piperazine | 7.33(1H, d), 7.00(2H, m), 6.84 (1H, m), 6.44(1H, d), 6.38(1H, dd), 3.90(3H, s), 3.86(3H, s), 3.33 (1H, q), 3.17(4H, t), 2.65(2H, m), 2.53(2H, m), 1.37(3H, d) | 432.34 M+ | C |

TABLE I-continued

| EX # | STRUCTURE | NAME | 1H NMR (400 MHz, CDCl3) | MS | Method |
|---|---|---|---|---|---|
| 51 | 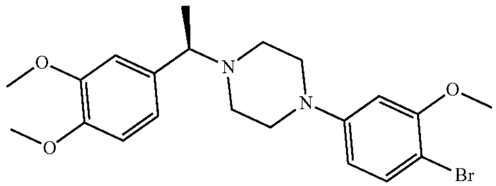 | 1-(4-bromo-3-methoxyphenyl)-4-[1-(3,4-dimethoxyphenyl)-ethyl]piperazine (racemic and R) | 7.18(1H, d), 6.83–6.91(3H, m), 6.41–6.44(2H, m), 3.87(9H, t), 3.23(1H, q), 3.15(4H, t)2.51–2.65(4H, m), 1.38(3H, d) | 391 M+ | D |
| 52 | 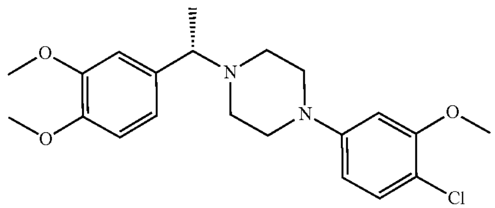 | S-1-(4-chloro-3-methoxyphenyl)-4-[1-(3,4-dimethoxyphenyl)ethyl]piperazine | 7.18(1H, d), 6.83–6.91(3H, m), 6.41–6.44(2H, m), 3.87(9H, t), 3.23(1H, q), 3.15(4H, t)2.51–2.65(4H, m), 1.38(3H, d) | 391 M+ | D |
| 53 | 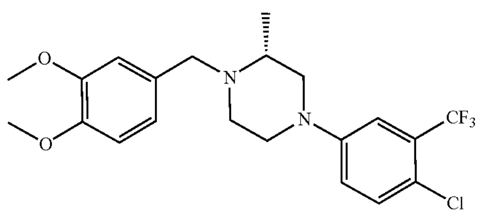 | (3S)-1-(4-chloro-3-trifluoromethoxyphenyl)-4-[1-(3,4-dimethoxy-benzyl)]-2-methyl-piperazine | 7.5(1H, d), 7.363(3H, m), 6.985(2H, m), 4.63(1H, d), 3.94(2H, m) 3.75(6H, d), 3.6 1(1H, d), 3.18(2H, m), 2.98(2H, s), 2.23(1H, s), 1.537(3H, d). | 429.2 M+ | B |
| 54 | 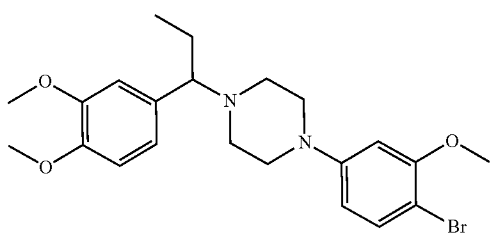 | 1-(4-Bromo-3-methoxy-phenyl)-4-[1-(3,4-dimethoxy-phenyl)-propyl]-piperazine | 7.36(1H, d), 6.81(3H, m), 6.42(1H, d), 6.39(1H, dd), 3.91(3H, s), 3.88(3H, s), 3.83(3H, s), 3.50(1H, m), 3.18(4H, m), 2.62(4H, m), 0.78(3H, t) | 449.28 M+ | B,C |

TABLE I-continued

| EX # | STRUCTURE | NAME | 1H NMR (400 MHz, CDCl3) | MS | Method |
|---|---|---|---|---|---|
| 55 | 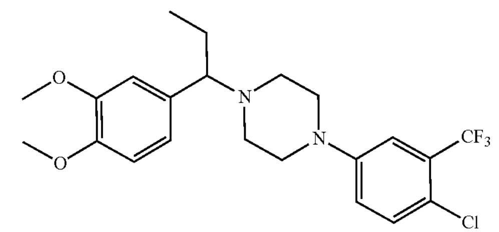 | 1-(4-Chloro-3-trifluoromethyl-phenyl)-4-[1-(3,4-dimethoxy-phenyl)-propyl]-piperazine | 7.29(1H, d), 7.17(1H, d), 6.76-6.85 (4H, m), 3.83(6H, d), 3.18(4H, m), 2.57(m, 4H0, 1.97(1H, m), 1.62 (2H, m), 0.78(3H, t) | 443 M+ | B |
| 56 | 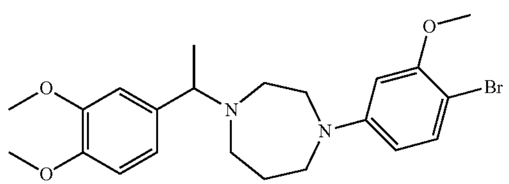 | 1-(4-Bromo-3-methoxy-phenyl)-4-[1-(3,4-dimethoxy-phenyl)-ethyl]-[1,4]diazepine | 7.43(2H, m), 6.89(1H, m), 6.76 (2H, m), 3.89(9H, t), 2.68(10H, m), 1.21(3H, d). | 450.36 M+ | B |
| 57 | 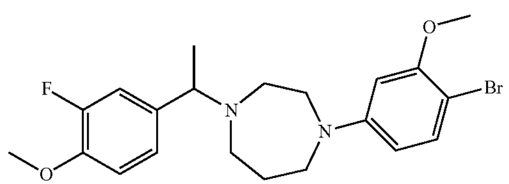 | 1-(4-Bromo-3-methoxy-phenyl)-4-[1-(3-fluoro-4-methoxy-phenyl)-ethyl]-[1,4]diazepine | 7.63(2H, m), 7.21(2H, m), 6.86 (2H, m), 4.46(1H, m), 3.89(6H, d), 2.68(10H, m), 1.41(3H, d). | 438.33 M+) | B |
| 58 | 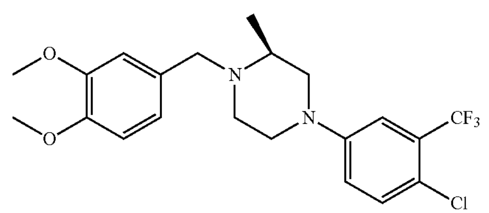 | (2S)-4-(4-chloro-3-trifluoromethyl-phenyl)-1-(3,4-dimethoxy-benzyl)-2-methyl-piperazine | 7.24(1H, d), 7.18(1H, d), 6.87(4H, m), 4.02(1H, m), 3.82(6H, d), 3.36 (2H, m), 3.08(1H, d), 2.82(3H, m), 2.59(1H, m), 2.22(1H, m) 1.21 (3H, d). | 429.26 M+ | A |
| 59 | 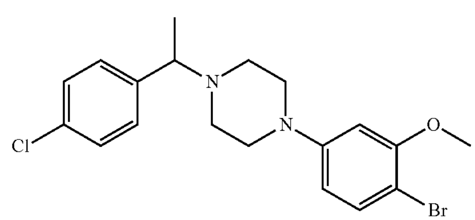 | 1-(4-bromo-3-methoxy-phenyl)-4-[1-(4-chloro-phenyl)-ethyl]-piperazine | 7.30(5H, m), 6.43(1H, d), 6.38(1h, dd), 3.83(3H, s), 3.38(1H, q), 3.17 (4H, t), 2.62(2H, m), 2.52(2H, m), 1.39(3H, d) | | B |

TABLE I-continued

| EX # | STRUCTURE | NAME | 1H NMR (400 MHz, CDCl3) | MS | Method |
|---|---|---|---|---|---|
| 60 | 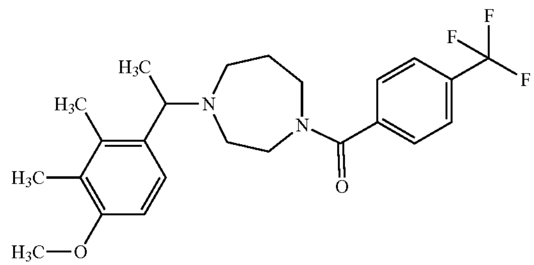 | {4-[1-(4-methoxy-2,3-dimethyl-phenyl)-[1,4]diazepin-1-yl]-(4-trifluoromethyl-phenyl)-methanone | 1.30(3H, dd), 1.60(1H, dm), 1.88(1H, dm), 2.17(3H, d), 2.31(3H, d), 2.45–2.94(4H, m), 3.22(1H, dm), 3.36(1H, t, J=8), 3.60(1H, dm), 3.81(3H, d), 3.84(1H, m), 3.99(1H, t, J=8), 6.67(1H, dd, J=11.2), 7.12(1H, dd, J=11.2), 7.38(1H, d, J=10.4), 7.50(1H, d, J=10.8), 7.58(1H, d, J=11.2), 7.66(1H, d, J=11.2). | 435.20 M+ | K |
| 61 | 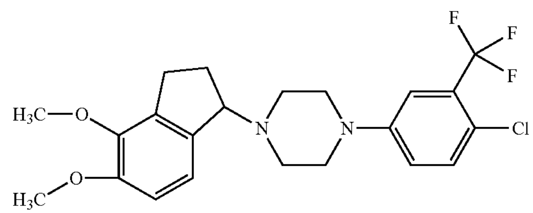 | 1-(4-chloro-3-trifluoromethyl-phenyl)-4-(4,5-dimethoxy-indan-1-yl)-piperazine | 7.31(1H, d), 7.15(1H, d), 7.03(1H, d), 6.93(1H, dd), 6.80(1H, d), 3.86(3H, s), 3.19(4H, m), 2.97(2H, m), 2.85(2H, m), 2.65(2H, m)2.12(2H, q) | 441.35 M+ | B |
| 62 | 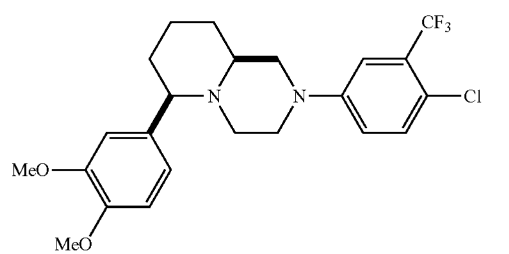 | 2-(4-chloro-3-trifluoromethyl-phenyl)-6-(3,4-dimethoxy-phenyl)-octahydro-pyrido[1,2-a]pyrazine | | 455.26 M+ | H |
| 63 | 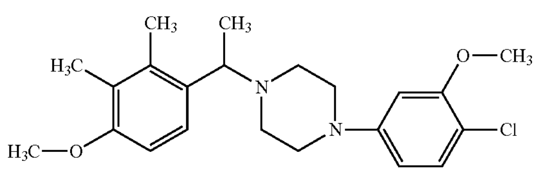 | 1-(4-chloro-3-methoxy-phenyl)-4-[1-(4-methoxy-2,3-dimethyl-phenyl)-ethyl]-piperazine | 7.27(1H, t), 7.18(1H, d), 6.72(1H, d), 6.48(1H, d), 6.44(1H, dd), 3.86(3H, s), 3.82(3H, s), 3.64(1H, q), 3.14(4H, m), 2.65(2H, m), 2.56(2H, m), 2.29(3H, s), 2.18(3H, s), 1.32(3H, d) | 389.2 M+ | C |

TABLE I-continued

| EX # | STRUCTURE | NAME | 1H NMR (400 MHz, CDCl3) | MS | Method |
|---|---|---|---|---|---|
| 64 | 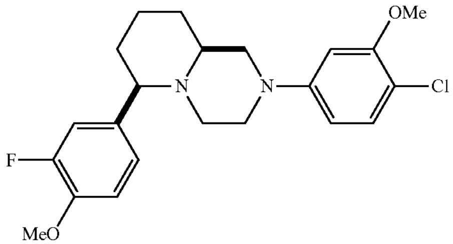 | (6R,10S)-2-(4-chloro-3-methoxy-phenyl)-6-(3-fluoro-4-methoxy-phenyl)-octahydro-pyrido[1,2-a]pyrazine | 7.30–7.00(3H, m), 6.89(1H, t), 6.42 (2H, m), 3.88(3H, s), 3.86(3H, s), 3.34(2H, m), 2.94(1H, d), 2.74 (2H, m), 2.62(1H, m), 2.31(1H, t), 2.03(1H, m), 1.88–1.66(7H, m) | 405.12 M+ | E |
| 65 | 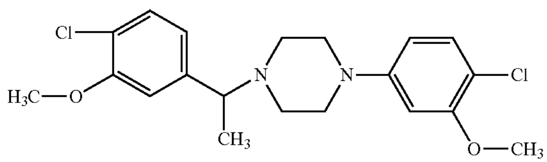 | 1-(4-chloro-3-methoxy-phenyl)-4-[1-(4-chloro-3-methoxy-phenyl)-ethyl]-piperazine | 7.29(1H, d), 7.18(1H, d), 6.97(1H, m), 6.86(1H, dd), 6.47(1H, d), 6.42 1H, dd), 3.54(1H, q), 3.15(1H, t), 2.64(2H, m), 2.53(2H, m), 1.37 (3H, d) | 395.35 M+ | B |
| 66 | 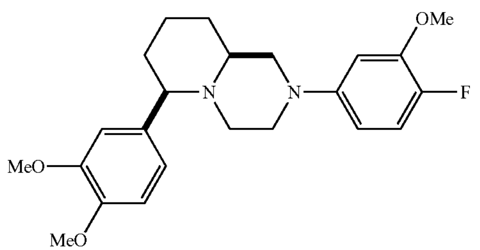 | 2-(4-fluoro-3-methoxy-phenyl)-6-(3,4-dimethoxy-phenyl)-octahydro-pyrido[1,2-a]pyrazine | 7.00–6.80(4H, m), 6.55(1H, dd), 6.40(1H, dm), 3.89(3H, s), 3.87 (3H, s) 3.86(3H, s), 3.40–3.20(2H, m), 2.95(1H, d), 2.784–2.52(3H, m), 2.30(1H, t), 2.8(1H,t), 1.90–1.40(6H, m) | 401.45 M+ | H |
| 67 | 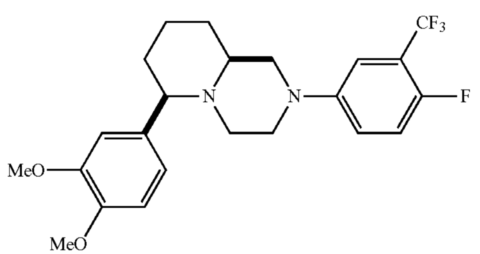 | 2-(4-fluoro-3-trifluoromethyl-phenyl)-6-(3,4-dimethoxy-phenyl)-octahydro-pyrido[1,2-a]pyrazine | 7.10–6.80(6H, m), 3.92(3H, s), 3.86(3H, s), 3.44–3.30(2H, m), 2.94(1H, m), 2.80–2.58(3H, m), 2.32(1H, m), 2.02(1H, m), 1.90–1.40(6H, m) | 439.48 M+ | H |

TABLE I-continued

| EX # | STRUCTURE | NAME | 1H NMR (400 MHz, CDCl3) | MS | Method |
|---|---|---|---|---|---|
| 68 | 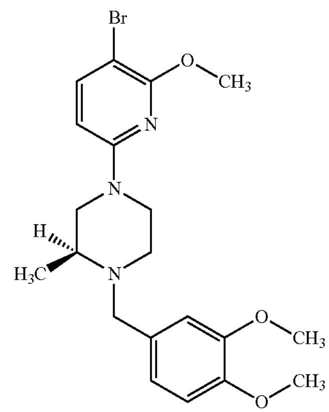 | (2S)-4-(4-chloro-3-methoxy-phenyl)-1-(3,4-dimethoxy-benzyl)-2-methyl-piperazine | 1.179(1H, s), 6.823(3H, m), 3.872(9H, t), 3.36(2H, m) 3.18(1H, d), 2.83(2H, m), 2.71(2H, m), 2.53(2H, m), 2.23(3H, s), 1.240(3H, m). | 391.43 M+ | A |
| 69 | 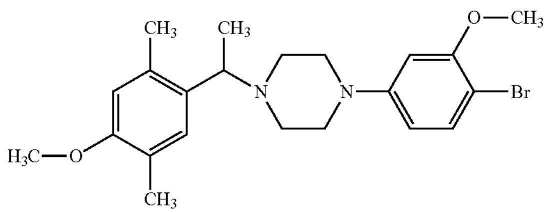 | 1-(4-bromo-3-methoxy-phenyl)-4-[1-(4-methoxy-2,5-dimethyl-phenyl)-ethyl]-piperazine | 7.32(1H, d), 7.20(1H, s), 6.91(1H, s), 6.45(1H, d), 6.37(1H, dd), 3.85 (3H, s), 3.53(1H, q), 3.12(4H, m), 2.66(2H, m), 2.54(2H, m), 2.30 (3H, s), 2.23(3H, s), 2.21(3H, s), 1.32(3H, d) | 435.10 M+ | C |
| 70 | 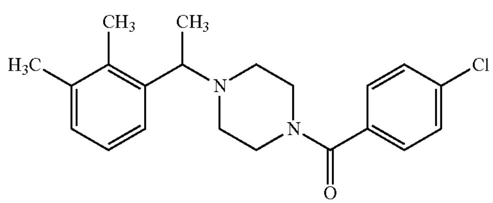 | 4-chloro-phenyl)-{4-[1-(2,3-dimethyl-phenyl)-ethyl]-piperazin-1-yl]}-methanone | 7.36(4H, m), 7.26(1H, m), 7.05 (2H, m), 3.67(3H, m), 3.32(2H, m), 2.45(4H, m), 2.28(3H, s), 2.25(3H, s), 1.30(3H, d). | 357.18 M+ | K |
| 71 | 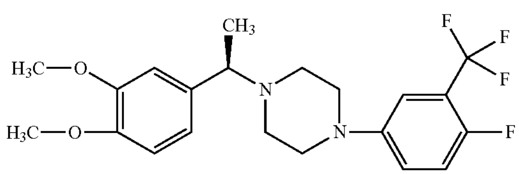 | R-1-(4-fluoro-3-trifluoromethyl-phenyl)-4-[1-(3,4-dimethoxy-phenyl)-ethyl]-piperazine | 7.04(3H, m), 6.91(1H, s), 6.83 (2H, m), 3.90(3H, s), 3.88 (3H, s), 3.34(1H, q), 3.13(4H, t), 2.64(2H, m), 2.54(2H, m), 1.39(3H, d) | 413.23 M+ | B |

TABLE I-continued

| EX # | STRUCTURE | NAME | 1H NMR (400 MHz, CDCl3) | MS | Method |
|---|---|---|---|---|---|
| 72 | 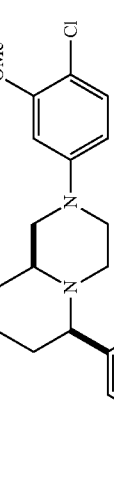 | 2-(4-chloro-3-methoxy-phenyl)-6-methoxy-naphthalen-2-yl)-octahydro-pyrido[1,2-a]pyrazine | 7.70(2H, m), 7.51(1H, m), 7.15 (3H, m), 6.42(2H, m), 3.92(3H, s), 3.86(3H, s), 3.74(1H, t), 3.32(1H, d), 3.14(1H, d), 2.74(3H, m), 2.39 (1H, m), 2.20–1.41(4H) | 437.13 M+ | E |
| 73 | 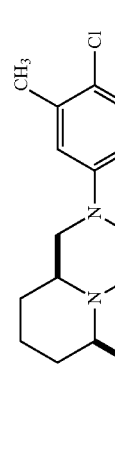 | 2-(4-chloro-3-methyl-phenyl)-6-(3,4-dimethoxy-phenyl)-octahydro-pyrido[1,2-a]pyrazine | | 401.28 M+ | H |
| 74 | 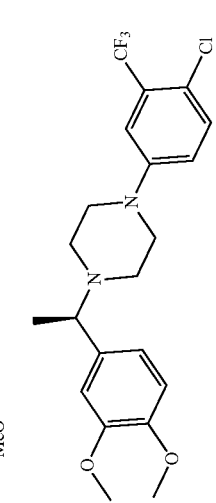 | R-1-(4-chloro-3-trifluoromethyl-phenyl)-4-[1-(3,4-dimethoxy-phenyl)-ethyl]-piperazine | 7.32(1H, d), 7.14(1H, d), 6.93(2H, m), 6.83(2H, m), 3.89(3H, s), 3.88 (3H, s), 3.34(1H, q), 3.17(4H, t), 2.64(2H, m), 2.53(2H, m), 1.38 (3H, d) | 429.23,431.18 M+,M + 2 | B |
| 75 | 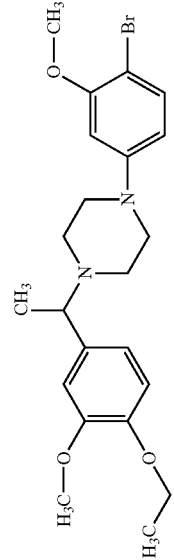 | 1-(4-bromo-3-methoxy-phenyl)-4-[1-(4-ethoxy-3-methoxy-phenyl)-ethyl]-piperazine | 7.33(1H, d), 6.92(3H, m), 6.44 (1H, d), 6.36(1H, dd), 4.09(2H, q), 3.88(3H, s), 3.85(3H, s), 3.33(1H, q), 3.16(4H, t), 2.65(2H, m), 2.54 (2H, m), 1.46(3H, t), 1.39(3H, d) | 449.38 M+ | C |

TABLE I-continued

| EX # | STRUCTURE | NAME | 1H NMR (400 MHz, CDCl3) | MS | Method |
|---|---|---|---|---|---|
| 76 | 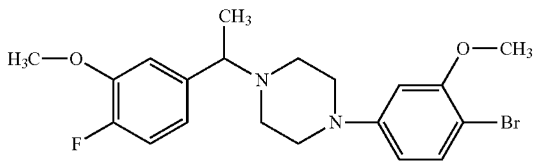 | 1-(4-bromo-3-methoxy-phenyl)-4-[1-(4-fluoro-3-methoxy-phenyl)-ethyl]-piperazine | 7.09(1H, d), 6.92(3H, m), 6.18 (1H, d), 6.13(1H, dd), 3.88(3H, s), 3.85(3H, s), 3.83(3H, s), 3.77(1H, q), 3.15(2H, m), 2.77(2H, m), 1.38 (3H, d) | 365.39 M+ | B |
| 77 | 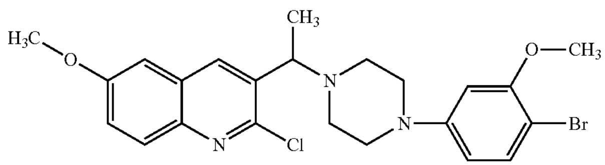 | 3-[1-[4-(4-bromo-3-methoxy-phenyl)-piperazin-1-yl]-ethyl]-2-chloro-6-methoxy-quinoline | 8.28(1H, s), 7.90(1H, d), 7.36(1H, d), 7.33(1H, d), 7.08(1H, d), 6.46 (1H, d), 6.39(1H, d), 4.03(1H, q), 3.92(3H, s), 3.86(3H, s), 3.20(4H, m), 2.79(2H, m), 2.64(2H, m), 1.42(3H, d) | 490.32,492.32 M+,M + 2 | C |
| 78 | 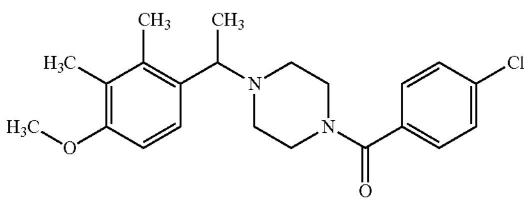 | (4-chloro-phenyl)-{4-[1-(4-methoxy-2,3-dimethyl-phenyl)-ethyl]-piperazin-1-yl}-methanone | | 423.34 426.32 M+,M + 2 | K |
| 79 | 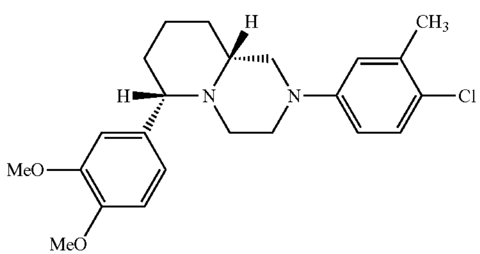 | (6S,10R)-2-(4-chloro-3-methoxy-phenyl)-6-(3,4-dimethoxy-phenyl)-octahydro-pyrido[1,2-a]pyrazine | 7.19(1H, d), 6.90(2H, m), 6.45 (1H, m), 6.41(1Hm dd), 3.91(3H, s), 3.89(3H, s), 3.87(3H, s), 3.41 (2H, m), 2.97(1H, dd), 2.75(1H, m), 2.62(1H, m), 2.37(1H, m), 2.03(1H, dt), 1.42–1.80(6H, m). | 417.23 M+ | E |
| 80 | 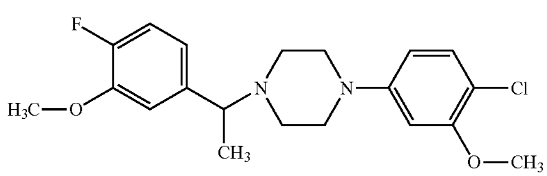 | 1-(4-chloro-3-methoxy-phenyl)-4-[1-(4-fluoro-3-methoxy-phenyl)-ethyl]-piperazine | 7.18(1H, d), 7.14(1H, dd), 7.03 (1H, m), 6.90(1H, m), 6.47(1H, d), 6.40(1H, dd), 3.88(3H, s), 3.86 (3H, s), 3.35(1H, q), 3.13(4H, t), 2.63(2H, m), 2.57(2H, m), 1.35 (3H, d) | 379.25 M+ | C |

TABLE I-continued

| EX # | STRUCTURE | NAME | 1H NMR (400 MHz, CDCl3) | MS | Method |
|---|---|---|---|---|---|
| 81 | 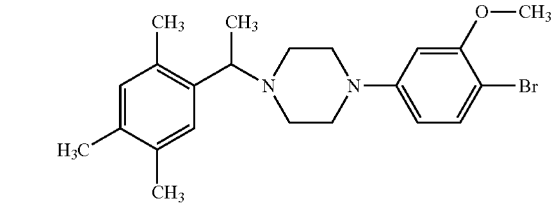 | 1-(4-bromo-3-methoxy-phenyl)-4-[1-(2,4,5-trimethyl-phenyl)-ethyl]-piperazine | 7.33(1H, d), 7.18(1H, s), 6.59(1H, s), 6.45(1H, d), 6.38(1H, dd), 3.85 (3H, s), 3.81(3H, s), 3.52(1H, q), 3.14(4H, m), 2.67(2H, m), 2.57 (2H, m), 2.34(3H, s), 2.18(3H, s), 1.31(3H, d) | 417.12,419.12 M+,M + 2 | C |
| 82 | 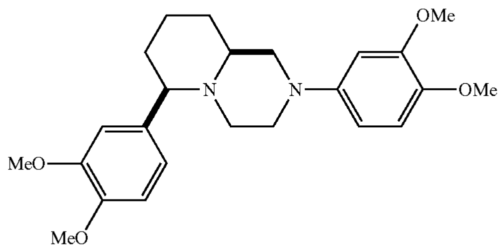 | 2-(4-methoxy-3-methyl-phenyl)-6-(3,4-dimethoxy-phenyl)-octahydro-pyrido[1,2-a]pyrazine | | 397.32 M+ | C |
| 83 | 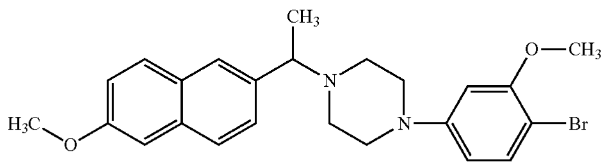 | 1-(4-bromo-3-methoxy-phenyl)-4-[1-(6-methoxy-naphthalen-2-yl)-ethyl]-piperazine | 7.70(3H, m), 7.50(1H, dd), 7.33 (1H, d), 7.14(2H, m), 6.44(1H, d), 6.36(1H, dd), 3.92(3H, s), 3.85 (3H, s), 3.53(1H, q), 3.16(4H, t), 2.69(2H, m), 2.58(2H, m), 1.47 (3H, d) | 455.16,457.15 M+,M + 2 | C |
| 84 | 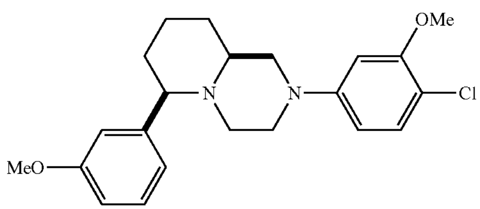 | 2-(4-chloro-3-methoxy-phenyl)-6-(3-methoxy-phenyl)-octahydro-pyrido[1,2-a]pyrazine | 7.21(2H, m), 6.93(2H, m), 6.77 (1H, dd), 6.46(1H, d), 6.41(1H, dd), 3.86(3H, s), 3.81(3H, s), 3.44 (1H, d), 3.40(1H, d), 3.00(1H, d), 2.80(2H, m), 2.60(1H, t), 2.29(1H, t), 2.95(1H, dt), 1.86–1.46(6H, m) | 387.23 M+ | H |
| 85 | 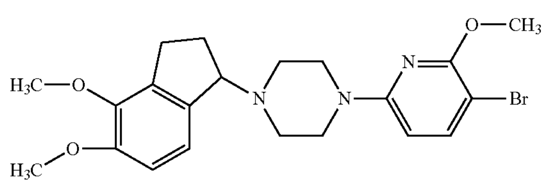 | 1-(4-bromo-3-methoxy-phenyl)-4-(4,5-dimethoxy-indan-1-yl)-piperazine | 7.46(1H, d), 7.02(1H, d), 6.81(1H, d), 6.04(1H, d), 4.37(1H, t), 3.88 (3H, s), 3.85(3H, s), 3.47(4H, m), 2.93(2H, m), 2.83(2H, m), 2.59 (4H, m), 2.10(2H, q) | 448.37 M+ | B |

TABLE I-continued

| EX # | NAME | 1H NMR (400 MHz, CDCl3) | MS | Method |
|---|---|---|---|---|
| 86 | 1-(4-bromo-3-methoxy-phenyl)-4-[1-3-fluoro-4-methoxy-phenyl)-ethyl]-piperazine | | | B |
| 87 | 2-(2,4-dibromo-5-methoxy-phenyl)-6-(3,4-dimethoxy-phenyl)-octahydro-pyrido[1,2-a]pyrazine | | | H |
| 88 | 7-(4-chloro-3-methoxy-phenyl)-4-(3,4-dimethoxy-phenyl)-decahydro-naphthalen-2-ol | 7.20(1H, dd), 6.96–6.82(3H, m), 6.47(1H, d), 6.42(1H, dd), 4.32 (1.5H, m), 4.00(1H, d), 3.88(3H, s), 3.87(6H, s), 3.65(0.5H, m), 3.27–2.84(5H, m), 2.68(1H, td), 2.09–1.94(3H, m), 1.62(2H, m) | 433.4 M+ | E |

TABLE I-continued
| EX # | STRUCTURE | NAME | 1H NMR (400 MHz, CDCl3) | MS | Method |
|---|---|---|---|---|---|
| 89 | 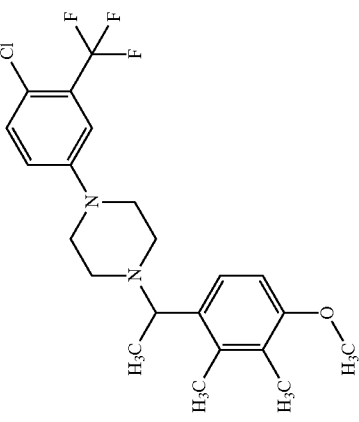 | 1-(4-chloro-3-trifluoromethyl-phenyl)-4-[1-(4-methoxy-2,3-dimethyl-phenyl)-ethyl]-piperazine | | 427.24 M+ | C |
| 90 | 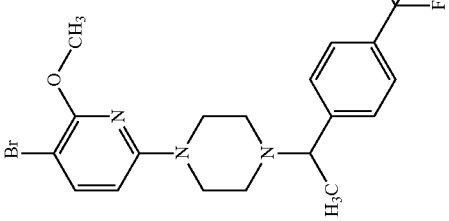 | 1-(5-bromo-6-methoxy-pyridin-2-yl)-4-[1-(4-trifluoromethyl-phenyl)-ethyl]-piperazine | 7.567(2H, d), 4.49(3H, m), 6.04 (1H, d), 3.90(3H, s), 3.47(5H, m), 2.62–2.44(4H, m), 1.39(3H, d). | 444.23 M+ | B |

TABLE I-continued

| EX # | STRUCTURE | NAME | 1H NMR (400 MHz, CDCl3) | MS | Method |
|---|---|---|---|---|---|
| 91 | 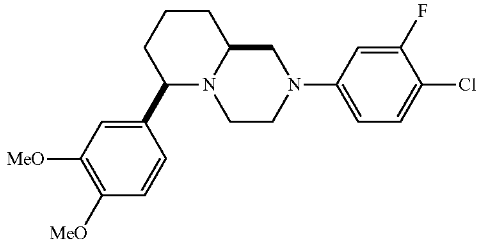 | 2-(4-chloro-3-fluoro-phenyl)-6-(3,4-dimethoxy-phenyl)-octahydro-pyrido[1,2-a]pyrazine | | 405.26 M+ | H |
| 92 | 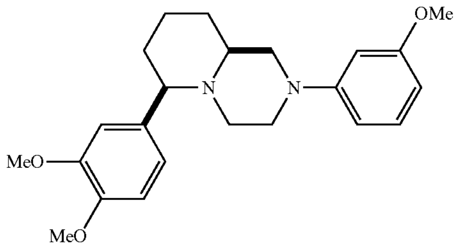 | 2-(3-methoxy-phenyl)-6-(3,4-dimethoxy-phenyl)-octahydro-pyrido[1,2-a]pyrazine | | | H |
| 93 | 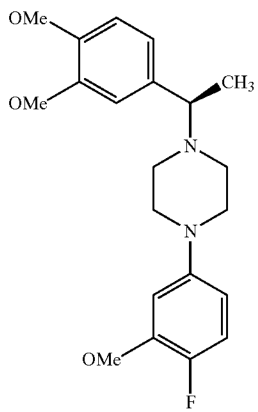 | R-1-(4-fluoro-3-methoxy-phenyl)-4-[1-(3,4-dimethoxy-phenyl)-ethyl]-piperazine | 7.00–6.80(4H, m), 6.58(1H, m), 6.40(1H, m), 3.88(3H, s), 3.86 (3H, s), 3.85(3H,s), 3.35(1H, q), 3.10(4H, m), 2.64(2H, m), 2.54 (2H, m), 1.38(3H, d) | 375.17 M+ | D |

TABLE I-continued

| EX # | STRUCTURE | NAME | 1H NMR (400 MHz, CDCl3) | MS | Method |
|---|---|---|---|---|---|
| 94 | 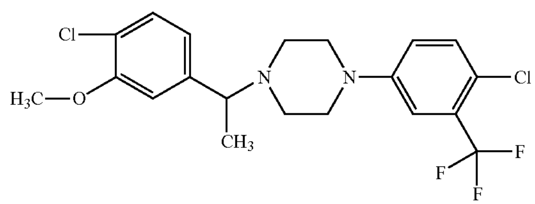 | 1-(4-chloro-3-trifluoromethyl-phenyl)-4-[1-(4-chloro-3-methoxy-phenyl)-ethyl]-piperazine | 7.31(2H, m), 7.14(1H, d), 6.94 (2H, m), 6.84(1H, dd), 3.91(3H, s), 3.35(1H, q), 3.18(4H, t), 2.64(2H, m), 2.54(2H, m), 1.37(3H, d) | 433.34, 435.33 M+,M + 2 | B |
| 95 | 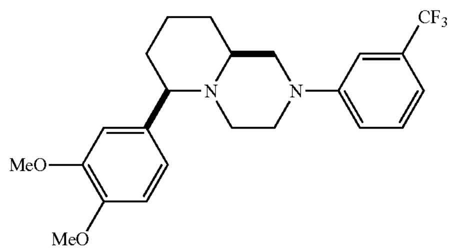 | 2-(3-trifluoromethyl-phenyl)-6-(3,4-dimethoxy-phenyl)-octahydro-pyrido[1,2-a]pyrazine | | 421.28 M+ | H |
| 96 | 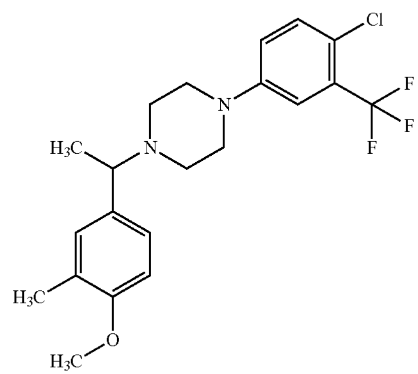 | 1-(4-chloro-3-trifluoromethyl-phenyl)-4-[1-(4-methoxy-3-methyl-phenyl)-ethyl]-piperazine | | 413.25 M+ | C |

TABLE I-continued

| EX # | STRUCTURE | NAME | 1H NMR (400 MHz, CDCl3) | MS | Method |
|---|---|---|---|---|---|
| 97 | 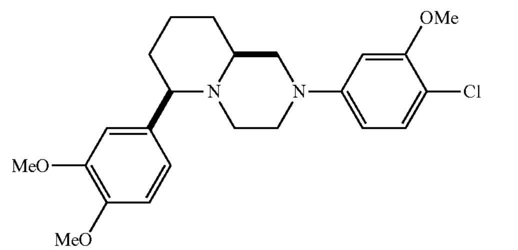 | 2-(4-chloro-3-methoxy-phenyl)-6-(3,4-dimethoxy-phenyl)-1,3,4,6,9,9a-hexahydro-2H-pyrido[1,2-a]pyrazine | 7.17(1H, d), 6.82(3H, m), 6.43 (1H, d), 6.38(1H, dd), 5.95(1H, m), 5.84(1H, dd), 4.33(1H, s), 3.88 (3H, s), 3.70(3H, s), 3.85(3H, s), 3.43(1H, d), 3.40(1H, m), 3.05(2H, m), 2.86(1H, m), 2.24(3H, m) | 415.18 M+ | L |
| 98 | 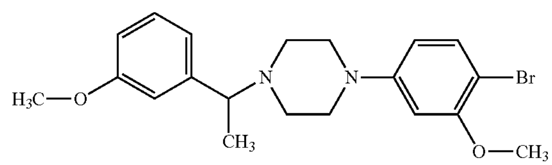 | 1-(4-bromo-3-methoxy-phenyl)-4-[1-(3-methoxy-phenyl)-ethyl]-piperazine | 7.33(1H, d), 7.24(1H, m), 6.92 (2H, m), 6.80(1H, dd), 6.44(1H, d), 6.39(1H, dd), 3.84(3H, s), 3.81 (3H, s), 3.36(1H, q), 3.14(4H, t), 2.65(2H, m), 2.55(2H, m), 1.39 (3H, d) | 405.20, 407.20 M+, M + 2 | C |
| 99 | 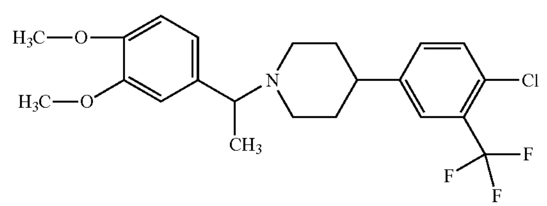 | 4-(4-chloro-3-trifluoromethyl-phenyl)-1-[1-(3,4-dimethoxy-phenyl)-ethyl]-piperadine | 7.53(1H, s), 7.40(1H, d), 7.31(1H, d), 6.89(1H, s), 6.83(2H, s), 3.91 (3H, s), 3.88(3H, s), 3.40(1H, q), 3.19(1H, d), 2.94(1H, d), 2.47(1H, m), 2.08(1H, m), 1.94(1H, m), 1.84–1.72(4H, m), 1.39(3H, d) | 428.27 M+ | B |

TABLE I-continued

| EX # | STRUCTURE | NAME | 1H NMR (400 MHz, CDCl3) | MS | Method |
|---|---|---|---|---|---|
| 100 | 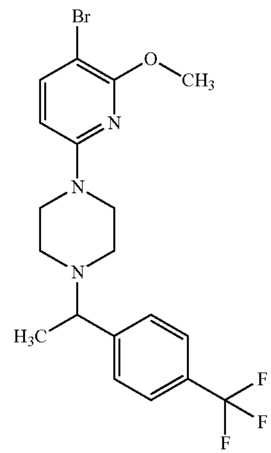 | 1-(4-bromo-3-methoxy-phenyl)-4-[1-(4-trifluoromethyl-phenyl)-ethyl]-piperazine | 7.59(2H, d), 7.46(2H, d), 7.33(1H, d), 6.44(1H, d), 6.38(1H, dd), 3.85 (3H, d), 3.43(1H, q), 3.15(4H, m), 2.63–2.46(4H, m), 1.39(3H, d). | 445.21 M+ | B |
| 101 | 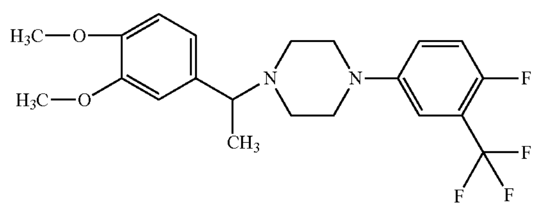 | 4-(4-fluoro-3-trifluoromethyl-phenyl)-1-[1-(3,4-dimethoxy-phenyl)-ethyl]-piperazine | 7.04(3H, m), 6.85(3H, m), 3.87 (3H, s), 3.80(3H, s), 3.37(1H, q), 3.11(4H, t), 2.63(2H, m), 2.57(2H, m), 1.40(3H, d) | 413.3 M+ | C |
| 102 | 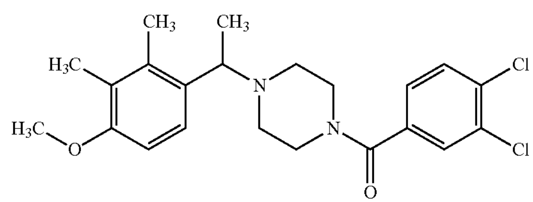 | (3,4-dichloro-phenyl)-{4-[1-(4-methoxy-2,3-dimethyl-phenyl)-ethyl]-piperazin-1-yl}-methanone | 7.45(2H, d), 7.26(2H, m), 6.64 (1H, d), 3.80(3H, s), 3.76(3H, m), 3.36(2H, m), 2.43(4H, m), 2.26 (3H, s), 2.16(3H, s), 1.30(3H, d). | 421.12 M+ | K |

TABLE I-continued
| EX # | STRUCTURE | NAME | 1H NMR (400 MHz, CDCl3) | MS | Method |
|---|---|---|---|---|---|
| 103 | 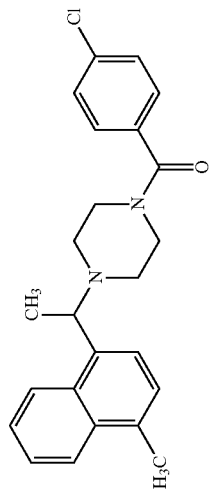 | (4-chloro-phenyl)-[4-[1-(4-methyl-naphthalen-1-yl)-ethyl]-piperazin-1-yl]-methanone | 8.21(1H, d), 8.01(1H, dd), 7.51 (2H, m), 7.43(1H, d), 7.33(3H, m), 7.26(2H, m), 4.07(1H, q), 3.68 (2H, m), 3.28(2H, m), 2.68(3H, s), 2.45(4H, m), 1.48(3H, d). | 393.16 M + 1 | K |
| 104 | 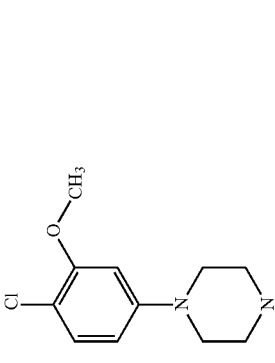 | 1-(4-chloro-3-methoxy-phenyl)-4-[1-(3-fluoro-4-methoxy-phenyl)-ethyl]-piperazine | 7.17(1H, d), 7.12(1H, dd), 7.03 (1H, d), 6.89(1H, m), 6.47(1H, d), 6.43(1H, dd), 3.88(3H, s), 3.86 (3H, s), 3.35(1H, q), 3.13(4H, t), 2.63(2H, m), 2.52(2H, m), 1.35 (3H, d) | 379.25 M+ | C |
| 105 | 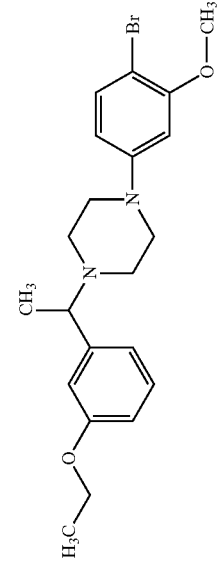 | 1-(4-bromo-3-methoxy-phenyl)-4-[1-(3-ethoxy-phenyl)-ethyl]-piperazine | 7.32(1H, d), 6.51(2H, d), 6.44(1H, d), 6.35(2H, m), 3.85(3H, s), 3.79 (6H, s), 3.31(1H, q), 3.17(4H, t), 2.66(2H, m), 2.55(2H, m), 1.37 (3H, d) | 435.31,437.29 M+,M + 2 | C |

TABLE I-continued

| EX # | NAME | STRUCTURE | 1H NMR (400 MHz, CDCl3) | MS | Method |
|---|---|---|---|---|---|
| 106 | 1-(5-{1-[4-(4-bromo-3-methoxy-phenyl)-piperazin-1-yl]-ethyl]-2-fluoro-phenyl)-ethanone | 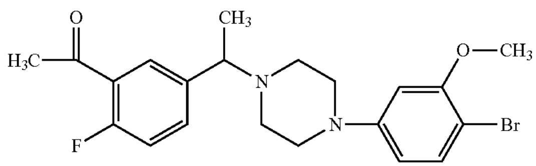 | 7.82(1H, dd), 7.57(1H, m), 7.37 (1H, d), 7.10(1H, m), 6.43(1H, d), 6.39(1H, dd), 3.84(3H, s), 3.45 (1H, q), 3.18(4H, t), 2.63(5H, m), 2.53(2H, m), 1.39(3H, d) | 435.33, 437.33 M+,M + 2 | C |
| 107 | 8-bromo-3-(3,4-dimethoxy-benzyl)-9-methoxy-2,3,4,4a-tetrahydro-1H,6H-pyrazino[1,2-a]quinoxalin-5-one | 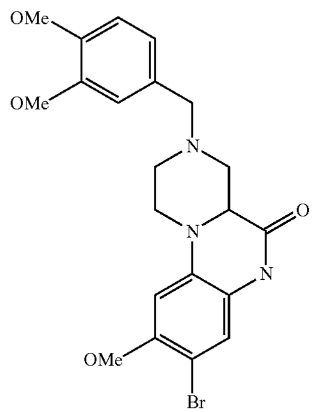 | 9.16(1H, s), 6.98–6.80(5H, m), 6.31(1H, s), 3.88(3H, s), 3.86(3H, s), 3.84(3H, s), 3.70–3.58(2H, m), 3.54–3.44(3H, m), 3.00–2.82(2H, m), 2.34–2.16(2H, m) | 462.18 M+ | M |

TABLE I-continued

| EX # | STRUCTURE | NAME | 1H NMR (400 MHz, CDCl3) | MS | Method |
|---|---|---|---|---|---|
| 108 | 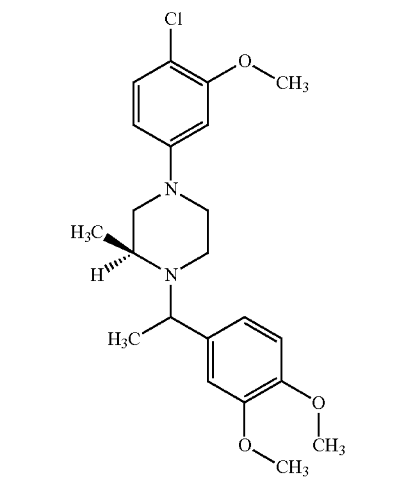 | (2S)-4-(4-chloro-3-methoxy-phenyl)-[1-(3,4-dimethoxy-benzyl)-ethyl]-2-methyl-piperazine | 7.19(1H, d), 6.97(3H, m), 4.83 (1H, q), 4.43(1H, q), 3.89(9H, t), 3.27(1H, d), 3.08(2H, m), 2.92 (2H, m), 2.64(1H, m), 2.42(2H, m), 1.42(3H, d), 1.23(3H, d). | 405.21(M + 1). | A |
| 109 | 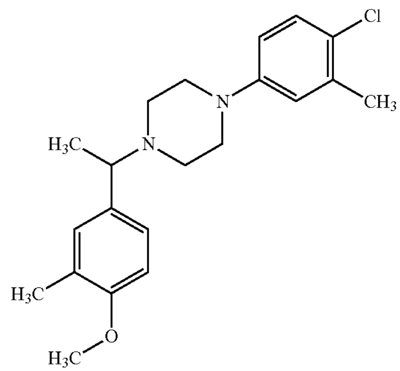 | 1-(4-chloro-3-methyl-phenyl)-4-[1-(4-methoxy-3-methyl-phenyl)-ethyl]-piperazine | | 359.26 M+ | C |

TABLE I-continued

| EX # | STRUCTURE | NAME | 1H NMR (400 MHz, CDCl3) | MS | Method |
|---|---|---|---|---|---|
| 110 | 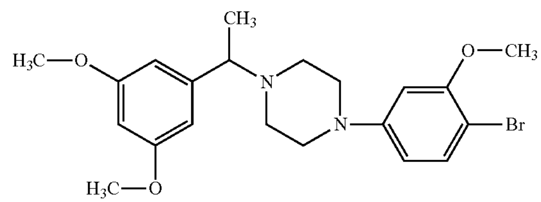 | 1-(4-bromo-3-methoxy-phenyl)-4-[1-(3,5-dimethoxy-phenyl)-ethyl]-piperazine | 7.32(1H, d), 6.52(2H, d), 6.44(1H, d), 6.38(2H, m), 3.85(3H, s), 3.79 (6H, s), 3.32(1H, q), 3.16(4H, t), 2.65(2H, m), 2.56(2H, m), 1.37 (3H, d) | 435.29, 437.31 M+,M + 2 | C |
| 111 | 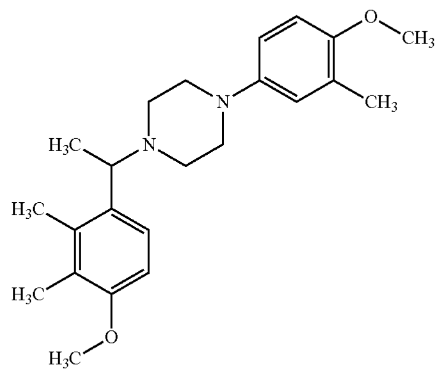 | 1-(4-methoxy-3-methyl-pheny)-4-[1-(4-methoxy-2,3-dimethyl-phenyl)-ethyl]-piperazine | | 369.30 M+ | C |
| 112 | 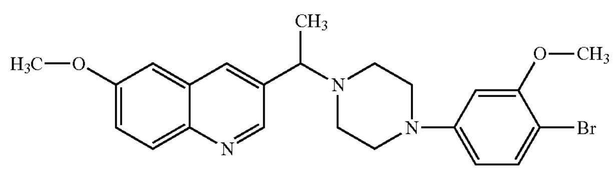 | 3-[1-[4-(4-bromo-3-methoxy-phenyl)-piperazin-1-yl]-ethyl]-6-methoxy-quinoline | 8.79(1H, s),7.98(2H, m), 7.35(2H, m), 7.08(1H, d), 6.44(1H, d), 6.36 (1H, dd), 3.93(3H, s), 3.85(s, 3), 3.64(1H, q), 3.18(4H, m), 2.71 (2H, m), 2.59(2H, m), 1.50(3H, d) | 456.45,458.15 (M+) | C |
| 113 | 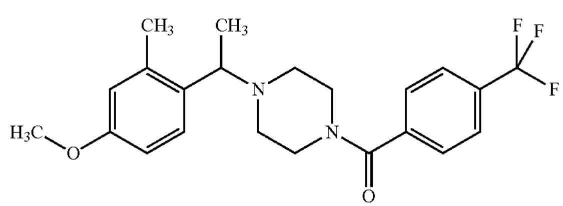 | 4-trifluoromethyl-phenyl)-{4-[1-(4-methoxy-2-methyl-phenyl)-ethyl]-piperazin-1-yl]-methanone | 7.67(2H, d), 7.51(2H, d), 7.27(1H, d), 6.68(2H, m), 3.78(5H, m), 3.58 (1H, q), 3.32(2H, m), 2.61–2.44 (3H, m), 2.33(3H, s), 1.29(3H, d). | 407.20 M + 1 | K |

TABLE I-continued

| EX # | STRUCTURE | NAME | 1H NMR (400 MHz, CDCl3) | MS | Method |
|---|---|---|---|---|---|
| 114 | 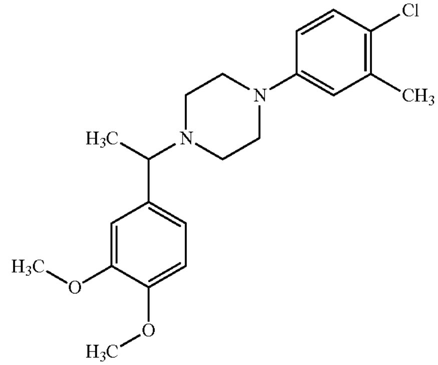 | 1-(4-chloro-3-methyl-phenyl)-4-[1-(3,4-dimethoxy-phenyl-ethyl]-piperazine | | 375.23 M+ | C |
| 115 | 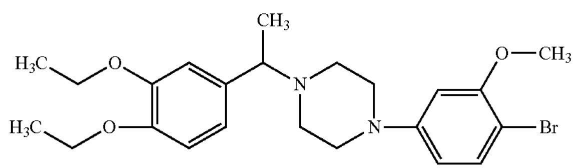 | 1-(4-bromo-3-methoxy-phenyl)-4-[1-(3,4-diethoxy-phenyl)-ethyl]-piperazine | 7.35(1H, d), 6.91(1H, s), 6.81(2H, s), 6.40(1H, d), 6.36(1H, dd), 4.12 (4H, m), 3.85(3H, s), 3.31(1H, q), 3.15(4H, t), 2.62(2H, m), 2.52(2H, m), 1.44(6H, m), 1.37(3H, d) | 463.37, 465.37 M+, M + 2 | C |
| 116 | 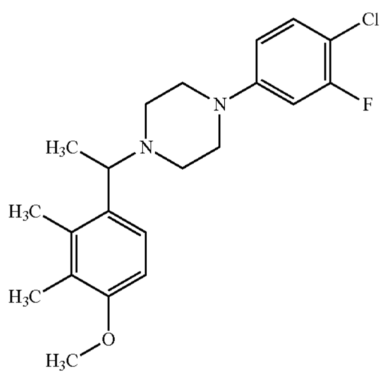 | 1-(4-chloro-3-fluoro-phenyl)-4-[1-(4-methoxy-2,3-dimethyl-phenyl)-ethyl]-piperazine | | 377.24 M+ | C |

TABLE I-continued

| EX # | STRUCTURE | NAME | 1H NMR (400 MHz, CDCl3) | MS | Method |
|---|---|---|---|---|---|
| 117 | 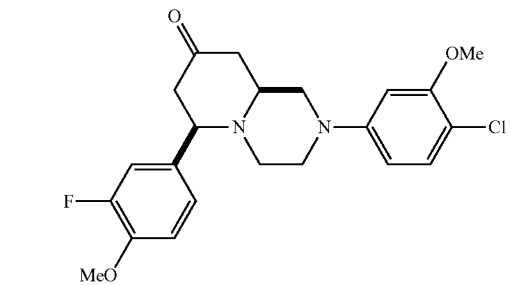 | 2-(4-chloro-3-methoxy-phenyl)-6-(3-fluoro-4-methoxy-phenyl)-octahydro-pyrido[1,2-a]pyrazin-8-one | 7.19(2H, m), 7.02(2H, d), 6.93 (2H, t), 6.46(1H, d), 6.40(1H, dd), 3.90(3H, s), 3.87(3H, s), 3.34(5H, m), 2.43–2.82(6H, m), 2.09(1H, td) | 419.2 M+ | E |
| 118 | 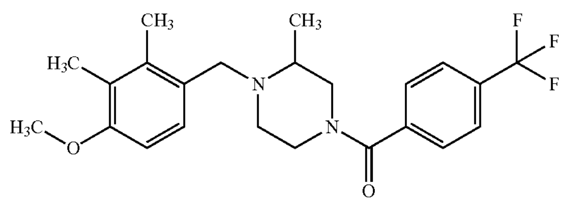 | 4-trifluoromethyl-phenyl)-{4-[1-(4-methoxy-2,3-dimethyl-phenyl)-ethyl]-piperazin-1-yl]-methanone | 7.63(2H, d), 7.51(2H, d), 7.01(1H, m), 6.63(1H, m), 4.08(2H, m), 3.81(6H, d), 3.38–3.06(4H, m), 2.67–2.43(2H, m), 2.93(3H, d). | 421.19 M + 1. | K |
| 119 | 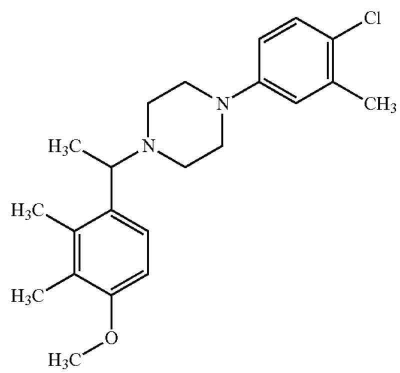 | 1-(4-chloro-3-methyl-phenyl)-4-[1-(4-methoxy-2,3-dimethyl-phenyl)-ethyl]-piperazine | | 373.26 M+ | C |

TABLE I-continued

| EX # | STRUCTURE | NAME | 1H NMR (400 MHz, CDCl3) | MS | Method |
|---|---|---|---|---|---|
| 120 | 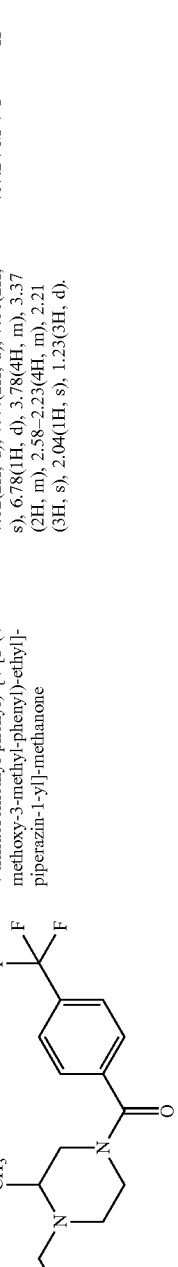 | 4-trifluoromethyl-phenyl)-{4-[1-(4-methoxy-3-methyl-phenyl)-ethyl]-piperazin-1-yl}-methanone | 7.62(2H, d), 7.44(2H, d), 7.06(2H, s), 6.78(1H, d), 3.78(4H, m), 3.37(2H, m), 2.58–2.23(4H, m), 2.21(3H, s), 2.04(1H, s), 1.23(3H, d). | 407.24 M + 1 | K |
| 121 | 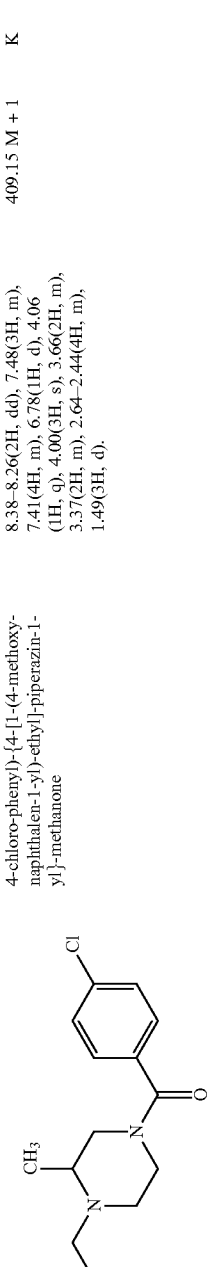 | 4-chloro-phenyl)-{4-[1-(4-methoxy-naphthalen-1-yl)-ethyl]-piperazin-1-yl}-methanone | 8.38–8.26(2H, dd), 7.48(3H, m), 7.41(4H, m), 6.78(1H, d), 4.06(1H, q), 4.00(3H, s), 3.66(2H, m), 3.37(2H, m), 2.64–2.44(4H, m), 1.49(3H, d). | 409.15 M + 1 | K |
| 122 | 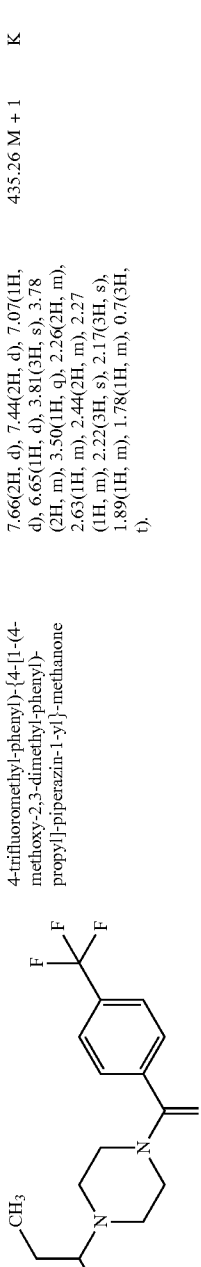 | 4-trifluoromethyl-phenyl)-{4-[1-(4-methoxy-2,3-dimethyl-phenyl)-propyl]-piperazin-1-yl}-methanone | 7.66(2H, d), 7.44(2H, d), 7.07(1H, d), 6.65(1H, d), 3.81(3H, s), 3.78(2H, m), 3.50(1H, q), 2.26(2H, m), 2.63(1H, m), 2.44(2H, m), 2.27(1H, m), 2.22(3H, s), 2.17(3H, s), 1.89(1H, m), 0.7(3H, t). | 435.26 M + 1 | K |
| 123 | 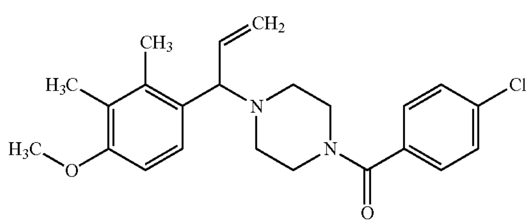 | (4-chloro-phenyl)-{4-[1-(4-methoxy-2,3-dimethyl-phenyl)-allyl]-piperazin-1-yl}-methanone | 7.35(3H, m), 7.26(1H, s), 6.72(1H, d), 5.84(1H, q), 5.21–5.08(2H, m), 3.94(1H, d), 3.80(3H, s), 3.78(1H, m), 2.45(3H, m), 2.25(3H, s), 2.17(3H, s), 0.98(3H, m). | 399.13 M + 1 | K |

TABLE I-continued

| EX # | STRUCTURE | NAME | 1H NMR (400 MHz, CDCl3) | MS | Method |
|---|---|---|---|---|---|
| 124 | 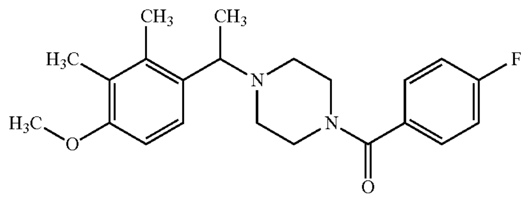 | 4-fluoro-phenyl)-{4-[1-(4-methoxy-2,3-dimethyl-phenyl)-ethyl]-piperazin-1-yl}-methanone | 7.38(2H, m), 7.17(1H, d), 7.05 (2H, m), 6.67(1H, d), 3.78(3H, s), 3.62(1H, q), 3.5(2H, m), 2.58–2.34 (4H, m), 2.25(3, s), 2.18(3H, s), 1.23(3H, d). | 371.28 M + 1 | K |
| 125 | 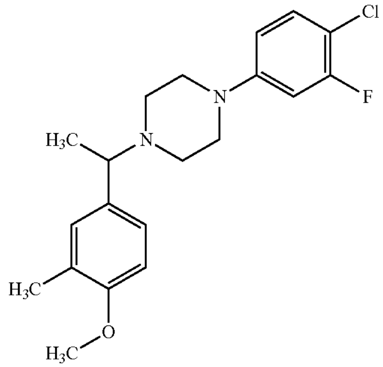 | 1-(4-chloro-3-fluoro-phenyl)-4-[1-(3,4-dimethoxy-phenyl)-ethyl]-piperazine | | 379.22 M+ | C |
| 126 | 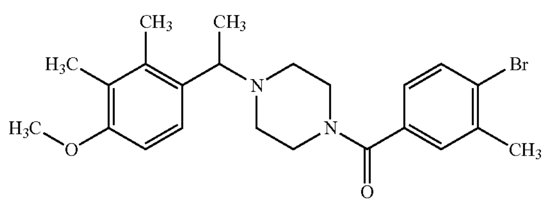 | 4-bromo-3-methyl-phenyl)-{4-[1-(4-methoxy-2,3-dimethyl-phenyl)-ethyl]-piperazin-1-yl}-methanone | 7.54(1H, d), 7.25(1H, s), 7.19(1H, d), 7.05(1H, d), 6.68(1H, d), 3.79 (3H, s), 3.66(3H, m), 3.48(2H, s), 3.38(2H, m), 2.29(2H, m), 2.39 (3H, s), 2.62(3H, s), 2.16(3H, s), 1.27(3H, d). | 447.15 M + 2 | K |
| 127 | 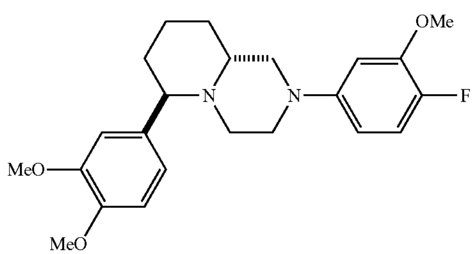 | 1-(4-fluoro-3-methoxy-phenyl)-6-(3,4-dimethoxy-phenyl)-octahydro-pyrido[1,2-a]pyrazine | 7.00–6.80(4H, m), 6.55(1H, dd), 6.40(1H, dm), 3.98–3.80(1H, m), 3.88(3H, s), 3.86(3H, s), 3.85 (3H, s), 3.42(1H, m), 3.14–2.78(6H, m), 2.00–1.80(2H, m), 1.78–1.38 (4H, m) | 401.26 M+ | H |

TABLE I-continued

| EX # | STRUCTURE | NAME | 1H NMR (400 MHz, CDCl3) | MS | Method |
|---|---|---|---|---|---|
| 128 | 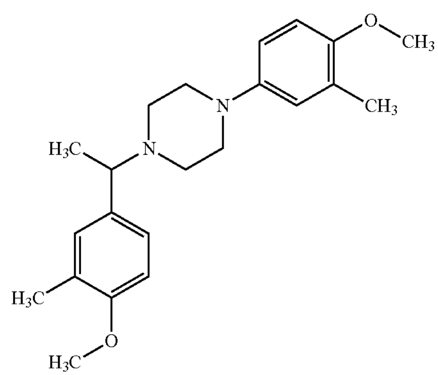 | 1-(4-methoxy-3-methyl-phenyl)-4-[1-(3-methyl-4-methoxy-phenyl)-ethyl]-piperazine | | 355.30 M+ | C |
| 129 | 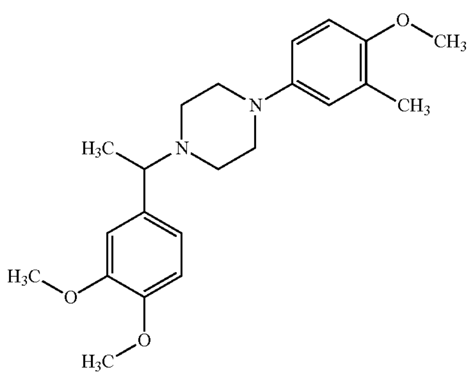 | 1-(4-methoxy-3-methyl-phenyl)-4-[1-(3,4-dimethoxy-phenyl)-ethyl]-piperazine | | 371.28 M+ | C |

TABLE I-continued

| EX # | STRUCTURE | NAME | 1H NMR (400 MHz, CDCl3) | MS | Method |
|---|---|---|---|---|---|
| 130 | 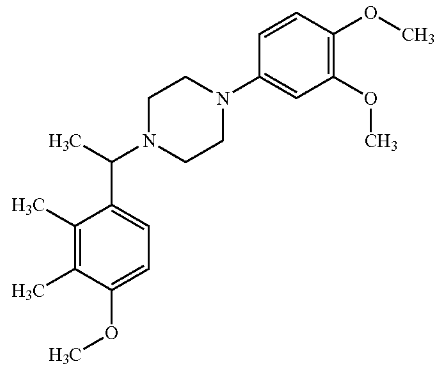 | 1-(3,4-dimethoxy-phenyl)-4-[1-(4-methoxy-2,3-dimethyl-phenyl)-ethyl]-piperazine | | 385.30 M+ | C |
| 131 | 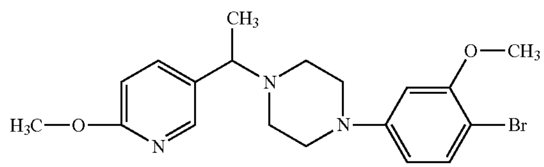 | 1-(4-bromo-3-methoxy-phenyl)-4-[1-(6-methoxy-pyridin-3-yl)-ethyl]-piperazine | 7.34(1H, d), 7.13(1H, s), 6.81(1H, s), 6.43(1H, d), 6.38(1H, dd), 3.90 (1H, m), 3.87(3H, s), 3.18(4H, t), 2.67(4H, m), 1.43(3H, d) | 459.19,461.19, 463.19 M+ | C |
| 132 | 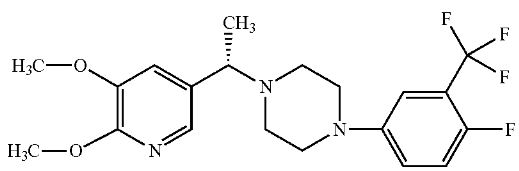 | R-1-(4-fluoro-3-trifluoromethyl-phenyl)-4-[1-(3,4-dimethoxy-phenyl)-ethyl]-piperazine | 7.04(3H, m), 6.91(1H, s), 6.83 (2H, m), 3.90(3H, s), 3.88(3H, s), 3.34(1H, q), 3.13(4H, t), 2.64(2H, m), 2.54(2H, m), 1.39(3H, d) | 413.20 M+ | B |
| 133 | 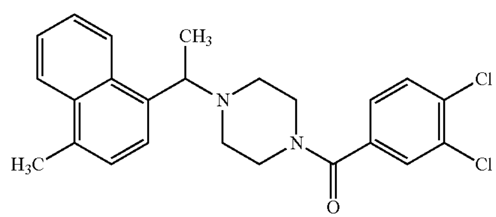 | (3,4-dichloro-phenyl)-{4-[1-(4-methyl-naphthalen-1-yl)-ethyl]-piperazin-1-yl}-methanone | 8.38–8.26(2H, dd), 7.48(3H, m), 7.41(3H, m), 6.78(1H, d), 4.06 (1H, q), 4.00(3H, s), 3.66(2H, m), 3.37(2H, m), 2.64–2.44(4H, m), 1.49(3H, d). | 428.13 M + 1 | K |

TABLE I-continued

| EX # | STRUCTURE | NAME | 1H NMR (400 MHz, CDCl3) | MS | Method |
|---|---|---|---|---|---|
| 134 | 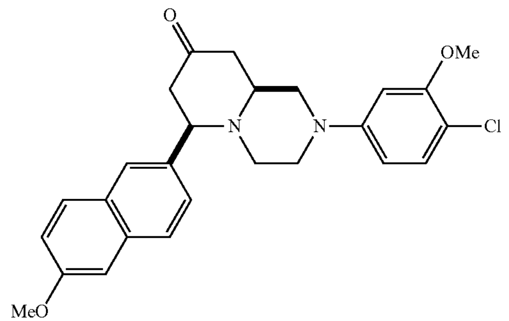 | 2-(4-chloro-3-methoxy-phenyl)-6-(6-methoxy-naphthalen-2-yl)-octahydro-pyrido[1,2-a]pyrazin-8-one | 7.77(3H, m), 7.72(1H, d), 7.19 (3H, m), 6.46(1H, d), 6.41(1H, d), 3.93(3H, 3H), 3.87(3H, s), 3.50(2H, m), 3.36(1H, d), 2.80 (5H, m), 2.48(3H, m), 2.43(1H, td) | 451.2 M+ | E |
| 135 | 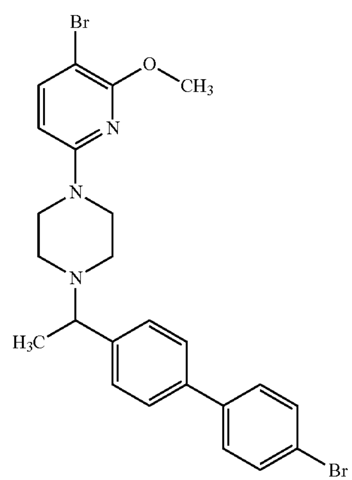 | 1-(4-bromo-3-methoxy-phenyl)-4-{1-[4-(4-bromo-phenyl)-phenyl]-ethyl}-piperazine | 7.57–7.40(9H, m), 7.33(1H, d), 6.82(1H, d), 6.42(d, 1H0< 6.37 (1H, dd), 3.83(3H, s), 3.52(1H, m), 3.22(m, 4H), 2.72(2H, m), 2.65 (2H, m), 1.43(3H, d) | | B |

TABLE I-continued

| EX # | STRUCTURE | NAME | 1H NMR (400 MHz, CDCl3) | MS | Method |
|---|---|---|---|---|---|
| 136 | 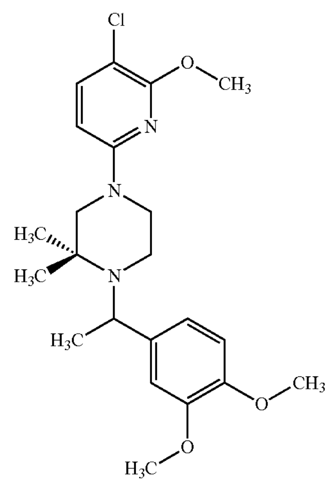 | (2R)-4-(4-chloro-3-methoxy-phenyl)-[1-(3,4-dimethoxy-benzyl)-ethyl]-2-methyl-piperazine | 7.19(1H, d), 6.97(3H, d), 4.83 (1H, q), 4.43(1H, q), 3.89(9H, t), 3.27(1H, d), 3.08(2H, m), 2.92 (2H, m), 2.64(1H, m), 2.42(2H, m), 1.42(3H, d), 1.23(3H, d). | 405.21 M + 1 | A |
| 137 | 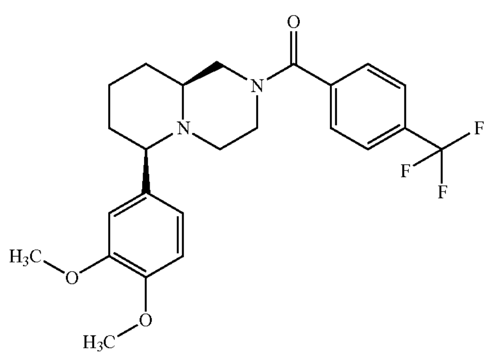 | [6-(3,4-dimethoxy-phenyl)-octahydro-pyrido[1,2-a]pyrazin-2-yl]-(4-trifluoro-phenyl)-methanone (mixture of rotamers) | 7.6–7.7(m, 2H); 7.4–7.5(m, 2H); 6.8(m, 3H); 4.4–4.6(m, 1H); 3.9(s, 6H); 1.0–3.4(m) F-19 NMR: −63.27, −63.34 ppm(1:1 ratio). | 449(M + 1) | G |

TABLE I-continued

| EX # | STRUCTURE | NAME | 1H NMR (400 MHz, CDCl3) | MS | Method |
|---|---|---|---|---|---|
| 138 | 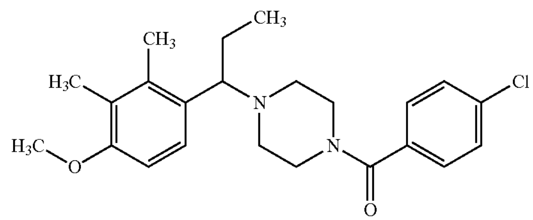 | 4-chloro-phenyl)-{4-[1-(4-methoxy-2,3-dimethyl-phenyl)-propyl]-piperazin-1-yl]-methanone | 7.38(4H, m), 7.12(1H, m), 6.63 (1H, d), 3.78(3H, s), 3.71(2H, m), 3.38(2H, m), 2.6–2.43(3H, m), 2.24(3H, s), 2.18(3H, s), 1.88(1H, m), 0.83(3H, t). | 401.20 M + 1 | K |
| 139 | 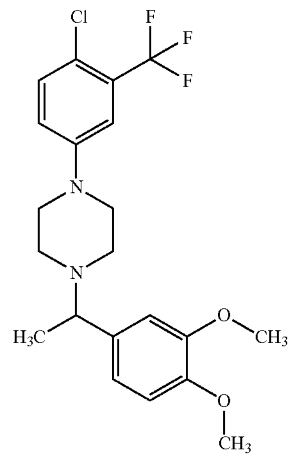 | S-4-(4-chloro-3-trifluoromethyl-phenyl)-[1-(3,4-dimethoxy-benzyl)-ethyl]-piperazine | | | B |
| 140 | 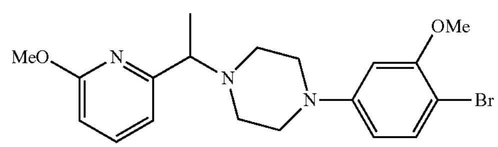 | 1-(4-Bromo-3-methoxy-phenyl)-4-[1-(6-methoxy-pyridin-2-yl)-ethyl]-piperazine | H-1 NMR: 7.54(1H, t), 7.33(1H, d), 6.93(1H, d), 6.59(1H, d), 6.45 (1H, d), 6.38(1H, dd), 3.93(3H, s), 3.85(3H, s), 3.64(1H, q), 3.17(4H, t), 2.70(4H, m), 1.44(3H, d) | 406.14,408.15 (M+) | C |
| 141 | 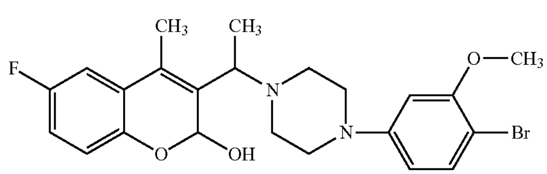 | 3-[1-[4-Bromo-3-methoxy-phenyl)-piperazin-1-yl]ethyl]-6-fluoro-4-methyl-2H-chromen-2-ol | 7.36(1H, m), 7.07–6.83(3H, m), 6.46–6.37(2H, m), 6.36(0.5H, s), 6.13(0.5H, s), 3.86, 3.85(3H, s), 3.62(0.5H, q), 3.43(0.5H, m), 3.14 (4H, m), 2.88(1H, m), 2.67(3H, m), 2.13(3H, s), 2.08(3H, s), 1.39 (3H, m) | 477.22,479.20 M+,M + 2 | B |

TABLE I-continued

| EX # | STRUCTURE | NAME | 1H NMR (400 MHz, CDCl3) | MS | Method |
|---|---|---|---|---|---|
| 142 | 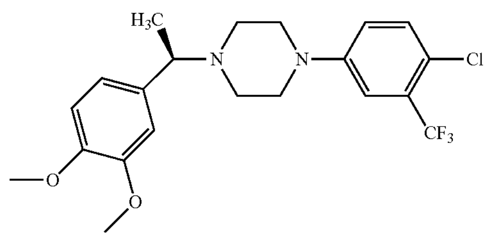 | R-4-(4-chloro-3-trifluoromethyl-phenyl)-[1-(3,4-dimethoxy-benzyl)-ethyl]-piperazine | | | B |
| 143 | 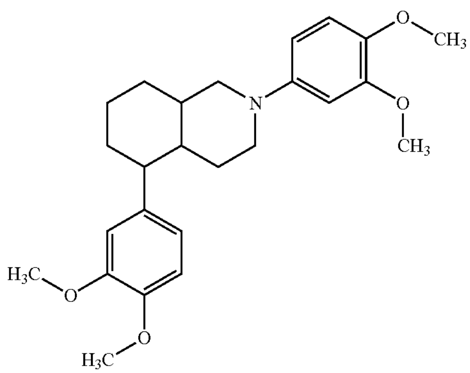 | 2-(3,4-dimethoxy-phenyl)-6-(3,4-dimethoxy-phenyl)-octahydro-pyrido[1,2-a]pyrazine | | 413.32 M+ | C |

Example 2

Melanin Concentrating Hormone Receptor Binding Assay

This Example illustrates a standard assay of melanin concentrating hormone receptor binding that may be used to determine the binding affinity of compounds for the MCH receptor.

Total RNA was prepared from Cynomolgus macaque hypothalamus. Monkey hypothalamic cDNA was prepared using random primers and reverse transcriptase according to standard methods. A cDNA encoding the monkey MCH1 receptor was obtained via PCR amplification using the forward (5') Primer of SEQ ID NO:3 and the reverse (3') Primer of SEQ ID NO:4. The full length PCR product was initially cloned into the vector pCR 2.1 (Invitrogen, Carlsbad, Calif.). The cDNA was reamplified using a forward primer engineered to include an optimal translation initiation site (Kozak sequence). A cDNA expression cassette fragment encoding the monkey MCH1 receptor was blunt end ligated into the PCR-SCRIPT vector (STRATAGENE, La Jolla, Calif.). The receptor sequence was excised from this vector using EcoRI and Not I and subcloned into the EcoRI/Not site of PCDNA3.1 (INVITROGEN Corp., Carlsbad, Calif.). The MCH1 receptor DNA sequence is provided in SEQ ID NO:1, with the encoded amino acid sequence provided in SEQ ID NO:2.

HEK 293 cells (American Type Culture Collection, Manassas, Va.) were stably transfected with the MCH receptor expression vector via standard calcium phosphate precipitation, and were grown to confluency (approximately 48–72 hours) in DMEM high glucose culture medium (catalog #10-017-CV, MEDIATECH, Herndon, Va.) supplemented with 10% fetal bovine serum and 25 mM HEPES, and 500 µg/ml G418, for 48–72 hours at 37° C., 5% $CO_2$. The cells were pelleted by gentle centrifugation. Cell pellets were washed twice with cold PBS, harvested in cold PBS containing 5 mM EDTA, and stored at −80° C.

At the time of assay, pellets were thawed by addition of wash buffer (25 mM Hepes with 1.0 mM $CaCl_2$, 5.0 mM $MgCl_2$, 120 mM NaCl, PH7.4) and homogenized for 30 seconds using a BRINKMAN POLYTRON, setting 5. Cells were centrifuged for 10 minutes at 48,000× g. The supernatant was discarded and the pellet was resuspended in fresh wash buffer, and homogenized again. An aliquot of this membrane homogenate was used to determine protein concentration via the Bradford method (BIO-RAD Protein Assay Kit, #500–0001, BIO-RAD, Hercules, Calif.). By this measure, a 1-liter culture of cells typically yields 50–75 mg of total membrane protein. The homogenate was centrifuged as before and resuspended to a protein concentration of 333 µg/ml in binding buffer (Wash buffer+0.1% BSA and 1.0 µM final phosphoramidon) for an assay volume of 50 µg membrane protein/150 ul binding buffer. Phosphoramidon was from SIGMA BIOCHEMICALS, St. Louis, Mo. (cat# R-7385).

Competition binding assays were performed at room temperature in Falcon 96 well round bottom polypropylene plates. Each assay well contained 150 µl of MCH receptor containing membranes prepared as described above, 50 µl $^{125}$I-Tyr MCH, 50 µl binding buffer, and 2 µl test compound in DMSO. $^{125}$I-Tyr MCH (specific activity=2200 Ci/mMol) is purchased from NEN, Boston, Mass. (Cat # NEX 373) and was diluted in binding buffer to provide a final assay concentration of 30 pM.

Non-specific binding was defined as the binding measured in the presence of 1 µM unlabeled MCH. MCH is purchased from BACHEM U.S.A., King of Prussia, Pa. (cat # H-1482). Assay wells used to determine MCH binding contained 150 µl of MCH receptor containing membranes, 50,µl $^{125}$I-Tyr MCH, 25 µl binding buffer, and 25 µl binding buffer.

Assay plates were incubated for 1 hour at room temperature. Membranes were harvested onto WALLAC™ glass fiber filters (PERKIN-ELMER, Gaithersburg, Md.) which were pre-soaked with 1.0% PEI (polyethyleneimine) for 2 hours prior to use. Filters were allowed to dry overnight, and then counted in a WALLAC 1205 BETA PLATE counter after addition of WALLAC BETA SCINT™ scintillation fluid.

For saturation binding, the concentration of $^{125}$I-Tyr MCH was varied from 7 to 1,000 pM. Typically, 11 concentration points were collected per saturation binding curve. Equilibrium binding parameters were determined by fitting the allosteric Hill equation to the measured values with the aid of the computer program FitP™ (BIOSOFT, Ferguson, Mo.). For the compounds described herein, $K_i$ values were below 1 micromolar, preferably below 500 nanomolar, more preferably below 100 nanomolar.

Example 3

Calcium Mobilization Assay

This Example illustrates a representative functional assay for monitoring the response of cells expressing melanin concentrating hormone receptors to melanin concentrating hormone. This assay can also be used to determine if test compounds act as agonists or antagonists of melanin concentrating hormone receptors.

Chinese Hamster Ovary (CHO) cells (American Type Culture Collection; Manassas, Va.) were stably transfected with the MCH expression vector described in Example 2 via calcium phosphate precipitation, and were grown to a density of 15,000 cells/well in FALCON™ black-walled, clear-bottomed 96-well plates (#3904, BECTON-DICKINSON, Franklin Lakes, N.J.) in Ham's F12 culture medium (MEDIATECH, Herndon, Va.) supplemented with 10% fetal bovine serum, 25 mM HEPES and 500 µg/mL (active) G418. Prior to running the assay, the culture medium was emptied from the 96 well plates. Fluo-3 calcium sensitive dye (Molecular Probes, Eugene, Oreg.) was added to each well (dye solution: 1 mg FLUO-3 AM, 440 µL DMSO and 440 µl 20% pluronic acid in DMSO, diluted 1:4, 50 µl diluted solution per well). Plates were covered with aluminum foil and incubated at 37° C. for 1–2 hours. After the incubation, the dye was emptied from the plates, cells were washed once in 100 µl KRH buffer (0.05 mM KCl, 0.115 M NaCl, 9.6 mM $NaH_2PO_4$, 0.01 mM $MgSO_4$, 25 mM HEPES, pH 7.4) to remove excess dye; after washing, 80 µl KRH buffer was added to each well.

Fluorescence response was monitored upon the addition of either human MCH receptor or test compound by a FLIPR™ plate reader (Molecular Devices, Sunnyvale, Calif.) by excitation at 480 nM and emission at 530 nM.

In order to measure the ability of a test compound to antagonize the response of cells expressing MCH receptors to MCH, the $EC_{50}$ of MCH was first determined. An additional 20 µl of KRH buffer and 1 µl DMSO was added to each well of cells, prepared as described above. 100 µl human MCH in KRH buffer was automatically transferred by the FLIPR instrument to each well. An 8-point concentration response curve, with final MCH concentrations of 1 nM to 3 µM, was used to determine MCH $EC_{50}$.

Test compounds were dissolved in DMSO, diluted in 20 µl KRH buffer, and added to cells prepared as described above. The 96 well plates containing prepared cells and test compounds were incubated in the dark, at room temperature for 0.5–6 hours. It is important that the incubation not continue beyond 6 hours. Just prior to determining the fluorescence response, 100 µl human MCH diluted in KRH buffer to $2 \times EC_{50}$ was automatically added by the FLIPR instrument to each well of the 96 well plate for a final sample volume of 200 µl and a final MCH concentration of $EC_{50}$. The final concentration of test compounds in the assay wells was between 1 µM and 5 µM. Typically, cells exposed to one $EC_{50}$ of MCH exhibit a fluorescence response of about 10,000 Relative Fluorescence Units. Antagonists of the MCH receptor exhibit a response that is significantly less than that of the control cells to the $p \leq 0.05$ level, as measured using a parametric test of statistical significance. Typically, antagonists of the MCH receptor decreased the fluorescence response by about 20%, preferably by about 50%, and most preferably by at least 80% as compared to matched controls.

The ability of a compound to act as an agonist of the MCH receptor was determined by measuring the fluorescence response of cells expressing MCH receptors, using the methods described above, in the absence of MCH. Compounds that cause cells to exhibit fluorescence above background are MCH receptor agonists.

Example 4

Determination of Dopamine $D_2$ and $D_4$ Receptor Binding Activity

This Example illustrates a representative standard assay for determining the binding affinity of compounds to dopamine $D_4$ and $D_2$ receptors.

Pellets of Chinese hamster ovary (CHO) cells containing recombinantly expressing primate $D_2$, human D4 dopamine receptors were used for the assays. The sample was homogenized in 100 volumes (w/vol) of 0.05 M Tris HCl buffer containing 120 mM NaCl, 5 mM $MgCl_2$ and 1 mM EDTA at 4° C. and pH 7.4. The sample was then centrifuged at 30,000× g and resuspended and rehomogenized. The sample was then centrifuged as described and the final tissue sample was frozen until use. The tissue was resuspended 1:20 (wt/vol) in 0.05 M Tris HCl buffer containing 120 mM NaCl.

Incubations for dopaminergic binding are carried out at 25° C. and contain 0.4 ml of tissue sample, 0.1 nM $^3$H-YM 09151-2 (Nemonapride, cis-5-Chloro-2-methoxy-4-(methylamino)-N-(2-methyl-2-(phenylmethyl)-3-pyrrolidinyl)benzamide) and the compound of interest in a total incubation of 1.0 ml. Nonspecific binding was defined as that binding found in the presence of 1 micromolar spiperone; without further additions, nonspecific binding was less than 20% of total binding.

Example 5

MDCK Cytotoxicity Assay

This Example illustrates the evaluation of compound toxicity using a Madin Darby canine kidney (MDCK) cell cytoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of $0.1 \times 10^6$ cells/ml with warm (37° C.) medium (VITACELL Minimum Essential Medium Eagle, ATCC catalog # 30-2003). 100 µL of diluted cells is added to each well, except for five standard curve control wells that contain 100 µL of warm medium without cells. The plate is then incubated at 37° C. under 95% $O_2$, 5% $CO_2$ for 2 hours with constant shaking. After incubation, 50 µL of mammalian cell lysis solution is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD, (Meriden, Conn.) ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOPCOUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 µM of a preferred test compound exhibit ATP levels that are at least 80%, preferably at least 90%, of the untreated cells. When a 100 µM concentration of the test compound is used, cells treated with preferred test compounds exhibit ATP levels that are at least 50%, preferably at least 80%, of the ATP levels detected in untreated cells.

From the foregoing it will be appreciated that, although specific embodiments of the invention have been described herein for purposes of illustration, various modifications may be made without deviating from the spirit and scope of the invention.

Description of the Sequence Listing

| | |
|---|---|
| SEQ ID NO: 1 | Cynomolgus macaque MCH1R DNA sequence |
| SEQ ID NO: 2 | Cynomolgus macaque MCH1R amino acid sequence |
| SEQ ID NO: 3 | 5' Cynomolgus macaque MCH1R primer |
| SEQ ID NO: 4 | 3' Cynomolgus macaque MCH1R primer |

What is claimed is:

1. A compound of the formula

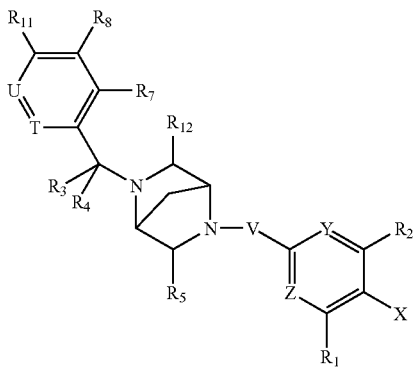

or a pharmaceutically acceptable salt thereof, wherein:
V is —(C=O)—;
X is selected from halogen, hydroxy, nitro, cyano, and groups of the formula L–M;
Y and Z are each independently: (i) CH; or (ii) nitrogen; with the proviso that Y and Z are not both nitrogen;
$R_1$ and $R_2$ are each independently selected from hydrogen, halogen, hydroxy, nitro, cyano, and groups of the formula L–M;
$R_3$ is: (i) selected from hydrogen, $(C_1-C_6)$alkyl, $(C_2-C_6)$alkenyl and halo$(C_1-C_6)$alkyl; or
  (ii) joined with $R_{10}$ to form a carbocyclic ring having from 5 to 8 ring members;
$R_4$ is hydrogen, $(C_1-C_6)$alkyl or halo$(C_1-C_6)$alkyl;
$R_5$ is selected from hydrogen, halogen, hydroxy, nitro, cyano, amino, oxo, $(C_1-C_6)$alkyl, $(C_2-C_6)$alkenyl, $(C_2-C_6)$alkynyl, $(C_1-C_6)$alkoxy, halo$(C_1-C_6)$alkyl, halo$(C_1-C_6)$alkoxy, mono- and di$(C_1-C_6)$alkylamino, and amino$(C_1-C_6)$alkyl;
$R_7$ is selected from hydrogen, halogen, hydroxy, nitro, cyano, —COOH, and groups of the formula L–M;
$R_8$ is selected from hydrogen, halogen, hydroxy, nitro, cyano, —COOH, and groups of the formula L–M;
U is N $CR_9$;
T is N or $CR_{10}$;
$R_9$ is selected from hydrogen, halogen, hydroxy, nitro, cyano, —COOH, and groups of the formula L–M;
$R_{10}$ is: (i) selected from hydrogen, halogen, hydroxy, nitro, cyano, —COOH, and groups of the formula L–M; or
  (ii) joined with $R_3$ to form a carbocyclic ring having from 5 to 8 ring members;
$R_{11}$ is selected from halogen, hydroxy, nitro, —COOH, and groups of the formula L–M;
$R_{12}$ is independently selected at each occurrence from hydrogen, halogen, hydroxy, nitro, cyano, amino, oxo, $(C_1-C_6)$alkyl, $(C_2-C_6)$alkenyl, $(C_2-C_6)$alkynyl, $(C_1-C_6)$alkoxy, halo$(C_1-C_6)$alkyl, halo$(C_1-C_6)$alkoxy, mono- and di$(C_1-C_6)$alkylamino, and amino$(C_1-C_6)$alkyl;
L is a bond, —$NR_{14}$—, —O—, —$SO_2$—, —$SO_2NH$—, —C(=O)$NR_{14}$—, or —$NR_{14}$C(=O)—, wherein $R_{14}$ is independently selected at each occurrence from hydrogen, $(C_1-C_6)$alkyl, $(C_2-C_6)$alkenyl, $(C_2-C_6)$alkynyl, and halo$(C_1-C_6)$alkyl; and
M is $(C_1-C_6)$alkyl, $(C_2-C_6)$alkenyl, $(C_2-C_6)$alkynyl, halo$(C_1-C_6)$alkyl, or amino$(C_1-C_6$ alkyl).

2. A compound or salt according to claim 1, wherein $R_3$ is hydrogen, $(C_1-C_3)$alkyl or halo$(C_1-C_3)$alkyl, and wherein $R_4$ is hydrogen.

3. A compound or salt according to claim 2, wherein $R_3$ is methyl, ethyl or trifluoromethyl.

4. A compound or salt according to claim 1, wherein $R_3$ and $R_{10}$ are joined to form a carbocyclic ring.

5. A compound or salt according to claim 1, wherein Y is nitrogen and Z is CH.

6. A compound or salt according to claim 1, wherein Y and Z are each CH.

7. A compound or salt according to claim 1, wherein X is a halogen, $(C_1-C_3)$alkyl, halo $(C_1-C_3)$alkyl, $(C_1-C_3)$alkoxy, halo$(C_1-C_3)$alkoxy or phenyl.

8. A compound or salt according to claim 7, wherein $R_1$ is hydrogen.

9. A compound or salt according to claim 7, wherein $R_{11}$ is methoxy or hydroxy.

10. compound or salt according to claim 7, wherein $R_{11}$ is halogen.

11. A compound or salt according to claim 1, wherein U is $CR_9$ and $R_7$, $R_8$, and $R_9$ are each independently selected from hydrogen, $C_1-C_6$ alkyl, $C_1-C_6$ alkoxy and halogen.

12. A compound or salt according to claim 1, wherein $R_{11}$ is halogen and $R_8$ is $(C_1-C_6)$alkoxy.

13. A compound or salt according to claim 1, wherein $R_5$ is hydrogen or methyl.

14. A compound or salt according to claim 1, of the formula:

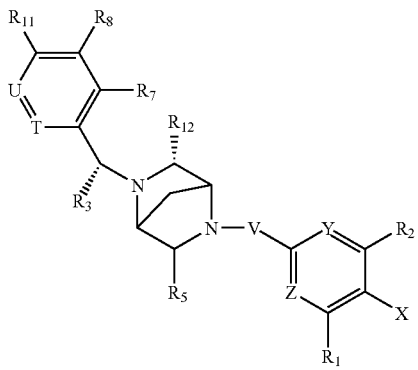

wherein at least one of $R_3$ and $R_{12}$ is not hydrogen.

15. A compound or salt according to claim 1, wherein the compound is {5-[1-4-Methoxy-2,3-dimethyl-phenyl)-ethyl]-(1S,4S)-2,5-diaza-bicyclo[2.2.1]hept-2-yl}-(4-trifluoromethyl-phenyl)-methanone.

16. A compound or salt according to claim 1, wherein:
$R_4$, $R_5$ and $R_{12}$ are hydrogen; and
$R_7$, $R_8$, and $R_9$ are each independently selected from hydrogen, $C_1-C_6$alkyl, $C_1-C_6$alkoxy and halogen; and
$R_{11}$ is selected from $C_1-C_6$alkoxy and halogen.

17. A compound or salt according to claim 16, wherein:
Y and Z are each CH;
X is halogen, methoxy or trifluoromethyl; and
$R_1$ and $R_2$ are independently chosen from hydrogen, halogen, methyl, methoxy and di- and tri-fluoromethyl.

18. A compound or salt according to claim 17, wherein:
$R_7$ is hydrogen or methyl;
$R_9$ is hydrogen, $C_1-C_6$alkyl, $C_1-C_6$alkoxy or halogen; and $R_8$ and $R_{11}$ are independently selected from $C_1$–$C_6$alkyl, $C_1$–$C_6$alkoxy and halogen.

19. A compound or salt according to claim 18, wherein $R_1$ is hydrogen; and
$R_2$ is halogen, methyl, methoxy or di- or tri-fluoromethyl.

20. A compound or salt according to claim 1, wherein $R_7$ is hydrogen or methyl, $R_8$ is methyl, $R_9$ is hydrogen, $R_{10}$ is hydrogen and $R_{11}$ is methoxy.

21. A pharmaceutical composition, comprising a compound or salt according to claim 1, in combination with a physiologically acceptable carrier or excipient.

22. A pharmaceutical composition according to claim 21, wherein the composition is formulated as an injectible fluid, an aerosol, a cream, a gel, a pill, a capsule, a syrup or a transdermal patch.

23. A method for treating a disease or disorder associated with pathogenic MCH receptor activation, comprising administering to a patient in need of such treatment an effective amount of a compound or salt according to claim 1 wherein the disease or disorder is an eating disorder or diabetes.

24. A method according to claim 23, wherein the compound or modulator is administered orally.

25. A method according to claim 23, wherein the compound or modulator is administered intranasally, intravenously or topically.

26. A method according to claim 23, wherein the patient is a human.

27. A method according to claim 23, wherein the patient is a dog or a cat.

28. A method for treating obesity in a patient, comprising administering to a patient in need of such treatment an effective amount of a compound or salt according to claim 1.

29. A method according to claim 28, wherein the compound or salt is administered orally.

30. A method according to claim 28, wherein the patient is a human.

31. A method according to claim 28, wherein the patient is a dog or a cat.

* * * * *